US010226455B2

(12) United States Patent
Sacchettini et al.

(10) Patent No.: US 10,226,455 B2
(45) Date of Patent: Mar. 12, 2019

(54) COMPOSITIONS AND METHODS FOR DRUG SENSITIZATION OF PARASITES

(71) Applicants: James C. Sacchettini, College Station, TX (US); Matthew W. Miller, College Station, TX (US); Deeann Wallis, College Station, TX (US); Nian E. Zhou, College Station, TX (US); Theresa W. Fossum, College Station, TX (US)

(72) Inventors: James C. Sacchettini, College Station, TX (US); Matthew W. Miller, College Station, TX (US); Deeann Wallis, College Station, TX (US); Nian E. Zhou, College Station, TX (US); Theresa W. Fossum, College Station, TX (US)

(73) Assignee: The Texas A&M University System, College Station, TX (US)

( * ) Notice: Subject to any disclaimer, the term of this patent is extended or adjusted under 35 U.S.C. 154(b) by 51 days.

(21) Appl. No.: 15/240,270

(22) Filed: Aug. 18, 2016

(65) Prior Publication Data

US 2016/0354358 A1 Dec. 8, 2016

Related U.S. Application Data

(63) Continuation of application No. PCT/US2015/016631, filed on Feb. 19, 2015.

(60) Provisional application No. 61/941,879, filed on Feb. 19, 2014.

(51) Int. Cl.
| | | |
|---|---|---|
| A61K 31/454 | (2006.01) | |
| A61K 31/7048 | (2006.01) | |
| A61K 31/427 | (2006.01) | |
| A61K 31/435 | (2006.01) | |
| A61K 31/5377 | (2006.01) | |
| A61K 47/54 | (2017.01) | |
| A61K 45/06 | (2006.01) | |

(52) U.S. Cl.
CPC .......... *A61K 31/454* (2013.01); *A61K 31/427* (2013.01); *A61K 31/435* (2013.01); *A61K 31/5377* (2013.01); *A61K 31/7048* (2013.01); *A61K 45/06* (2013.01); *A61K 47/542* (2017.08); *A61K 47/545* (2017.08); *Y02A 50/411* (2018.01); *Y02A 50/414* (2018.01); *Y02A 50/419* (2018.01); *Y02A 50/421* (2018.01); *Y02A 50/423* (2018.01); *Y02A 50/491* (2018.01)

(58) Field of Classification Search
CPC .............. A61K 31/454; A61K 31/7048; A61K 31/427; A61K 31/435; A61K 31/5377; A61K 47/545; A61K 47/542
See application file for complete search history.

(56) References Cited

U.S. PATENT DOCUMENTS 5,529,994 A * 6/1996 Remington .......... A61K 31/435
514/183
2005/0203076 A1 9/2005 Li et al.

FOREIGN PATENT DOCUMENTS

WO 96/16652 6/1996

OTHER PUBLICATIONS

Definition of prevent, Oxford English Dictionary Online, http://dictionary.oed.com/, accessed online Mar. 27, 2010, especially definition 9a. at p. 2. (Year: 2010).*
Bilgin et al., Balkan Med. J., 2013, 30, p. 19-22. (Year: 2013).*
Extended European Search Report received for European Patent Application No. 15752397.8, dated Aug. 30, 2017; 8 pages.
Ullman, Buddy. "Multidrug resistance and P-glycoproteins in parasitic protozoa." Journal of bioenergetics and biomembranes 27.1 (1995): 77-84; 8 pages.
Alger, Nelda E., Dan T. Spira, and Paul H. Silverman. "Inhibition of rodent malaria in mice by rifampicin." Nature 227.5256 (1970): 381-382; 2 pages.
Geary, Timothy G., and James B. Jensen. "Effects of antibiotics on Plasmodium falciparum in vitro." The American journal of tropical medicine and hygiene 32.2 (1983): 221-225; 5 pages.
Strath, Malcolm, et al. "Antimalarial activity of rifampicin in vitro and in rodent models." Transactions of the Royal Society of Tropical Medicine and Hygiene 87.2 (1993): 211-216; 6 pages.
Pukrittayakamee, S., et al. "Antimalarial effects of rifampin in Plasmodium vivax malaria." Antimicrobial agents and chemotherapy 38.3 (1994): 511-514; 4 pages.
Duffy, Sandra, and Vicky M. Avery. "Development and optimization of a novel 384-well anti-malarial imaging assay validated for high-throughput screening." The American journal of tropical medicine and hygiene 86.1 (2012): 84-92; 9 pages.

* cited by examiner

*Primary Examiner* — Jonathan S Lau
(74) *Attorney, Agent, or Firm* — Baker Botts L.L.P.

(57) ABSTRACT

Compositions and methods for inhibiting and/or sensitizing or re-sensitizing a parasite to an antiparasitic drug are provided. The compositions can comprise a rifamycin derivative or a pharmaceutically acceptable salt, hydrate, or prodrug thereof in an amount and formulation sufficient to inhibit or induce drug-sensitization in a parasite. The methods can comprise administering a rifamycin derivative or a pharmaceutically acceptable salt, hydrate, or prodrug thereof to a parasite in an amount and formulation sufficient to inhibit or induce drug-sensitization in the parasite.

18 Claims, 4 Drawing Sheets

COMPOSITIONS AND METHODS FOR DRUG SENSITIZATION OF PARASITES

CROSS-REFERENCE TO RELATED APPLICATION

The present application is a continuation application of PCT International Application Number PCT/US2015/016631 filed Feb. 19, 2015,which claims priority to U.S. Provisional Application No. 61/941,879 filed Feb. 19, 2014, the contents of which are hereby incorporated by reference in their entirety for all purposes.

TECHNICAL FIELD

The present disclosure relates to compositions for parasite inhibition and/or sensitization or re-sensitization of a parasite to another drug or combination of drugs. In particular, it relates to compositions comprising rifamycin and rifamycin derivatives, such as rifabutin or rifabutin derivatives, or rifampicin and rifampicin derivatives, or pharmaceutically acceptable salts, hydrates, or prodrugs thereof, or combinations thereof. The present disclosure also relates to methods of parasite inhibition and/or sensitizing or re-sensitizing a parasite to another drug or combination of drugs by applying rifamycin or a rifamycin derivative, such as rifabutin or a rifabutin derivative, or rifampicin or a rifampicin derivative, or a pharmaceutically acceptable salt, hydrate, or prodrug thereof, or a combination thereof, or a composition comprising the same to the parasite.

BACKGROUND

Treatment of Parasitic Infection

Parasitic infection is treated, or prevented, by the administration of a drug or drugs, such as xenobiotic chemotherapeutic drugs, to a susceptible or infected host organism. Effective treatment of parasitic infection by drug administration is frequently impaired, however, due to resistance of the parasite to the drug. Such resistance can be "inherent" to the parasite in the sense that the susceptibility of the parasite to the drug has not increased due to widespread use of the drug. Commonly, however, drug resistance of infectious parasites is observed due to evolved resistance associated with widespread treatment with the drug and associated selection pressure for resistant phenotypes. Currently, many infectious parasites are completely or highly resistant to available drugs and drug combinations, and parasites still susceptible to available drugs require treatment with greater doses than previously required, such that complete or effectively complete resistance is foreseeable.

For example, chloroquine resistance in certain species of malaria-causing *Plasmodium* parasites is so widespread that alternative or combination anti-malarial therapies are now required, and many parasitic species, including malaria-causing *Plasmodium* species, are now multi-drug resistant. As a further example, the incidence of parasite resistance to avermectins a widely used class of nematicides, acaridices and insecticides in veterinary and human medicine and plant protection, is increasing.

Resistance of infectious parasites to anti-parasitic drugs can be avoided or lessened by rendering the parasites more sensitive to one or more drugs. The calcium channel blocker Verapramil for example has been evaluated for its effect on sensitization of parasites to xenobiotics. However, safe, economical, and effective methods for sensitizing parasites in such a manner are lacking.

Drug Efflux Pumps

Drug efflux pumps are a primary mediator of drug resistance in parasites. Generally drug efflux pumps are cell membrane proteins that function as transporters of xenobiotic compounds within a cell to the exterior of the cell. In the malarial protozoan *Plasmodium falciparum*, for example, at least three transmembrane proteins are known to mediate chloroquine resistance, namely P-glycoprotein (permeability glycoprotein 1, "P-gp"), also referred to as multidrug resistance ("MDR") protein, P-glycoprotein homolog 1 (Pgh1,) and *Plasmodium falciparum*multidrug resistance protein (PfMDR). P-gp is an ATP-dependent drug efflux pump associated with drug and multidrug resistance in cells and organisms, and is known to mediate drug resistance in numerous parasites. B. Ullman, *Multidrug Resistance and P-glycoproteins in Parasitic Protozoa*, J. Bioenergetics and Biomembranes 27:1:77-84 (1995).

Rifamycin Antibiotics for Parasite Inhibition and or Sensitization

Rifabutin is a member of the rifamycin class of antibiotics, and was approved for use as an antibiotic in the United States in 1992. Although rifabutin has been tested for other antibiotic and anti-inflammatory uses, its most common use remains the treatment of tuberculosis and other *Mycobacterium* infections. Rifampicin, another member of the rifamycin class of antibiotics, was introduced in 1967 and is also used to treat tuberculosis and similar infections.

Several antibiotics, including tetracycline and rifampicin, have been reported to exhibit antimalarial activity. For example, rifampicin has been reported to prolong survival in mouse models of malaria, while the $FCR_{3TC}$ strain of *P. falciparum* has been reported to exhibit sensitivity to rifampicin at approximately 3.2 uM (a concentration that has been reported to be both achieved and effective in vivo during tuberculosis therapy) in vitro. Rifampicin was also reported to be effective against the chloroquine-resistant C10 strain of *P. falciparum* at 2.5 uM in vitro and against murine *P. chabaudi* infections with pretreatment or daily post-infection treatment post-infection at a dose of 100-200 mg/kg. However, a study of 60 human *P. vivax* patients found that rifampicin alone was not effective against the parasite. See Alger, N. E. et al., *Inhibition of rodent malaria in mice by rifampicin*. Nature, 1970. 227(5256): p. 381-2; Geary, T. G. and J. B. Jensen, *Effects of antibiotics on Plasmodium falciparum in vitro*. Am J Trop Med Hyg, 1983. 32(2): p. 221-5; Strath, M. et al., *Antimalarial activity of rifampicin in vitro and in rodent models*. Trans R Soc Trop Med Hyg, 1993. 87(2): p. 211-6; Pukrittayakamee, S., et al., *Antimalarial effects of rifampin in Plasmodium vivax malaria*. Antimicrob Agents Chemother, 1994. 38(3): p. 511-4.

SUMMARY

The present disclosure, in certain embodiments, relates to compositions comprising rifamycin, rifamycin derivatives, such as rifabutin or rifabutin derivatives, rifampicin and rifampicin derivatives, pharmaceutically acceptable salts, hydrates, or prodrugs thereof, and combinations thereof. The compositions are operable to inhibit, and/or to induce drug sensitization in, a parasite.

According to certain embodiments, the disclosure provides methods of sensitizing a parasite to a drug by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same, to the parasite.

According to certain embodiments, the disclosure provides methods of sensitizing a parasite to a drug by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same, to an organism susceptible to infection by the parasite.

According to certain embodiments, the disclosure provides a method of increasing the amount of a drug in a parasite by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same in an amount and for a time sufficient to decrease activity of or inhibit a drug efflux pump in the parasite.

According to certain embodiments, the disclosure provides methods of inhibiting a parasite with a drug by administering rifamycin, a rifamycin derivative, such as rifabutin or rifabutin derivatives, rifampicin, a rifampicin derivative, or a pharmaceutically acceptable salt, hydrate, or prodrug thereof, or a combination thereof, or a composition comprising same to the parasite in an amount and for a time sufficient to sensitize the parasite to the drug and administering the drug to the parasite in an amount and for a time sufficient to inhibit the parasite. The amount or time of administration with respect to the drug are less than that required to achieve the same inhibition in the absence of the rifamycin, rifamycin derivative, rifampicin, rifampicin derivative, or pharmaceutically acceptable salt, hydrate, or prodrug thereof, or combination thereof, or composition comprising same with respect to a given parasite.

According to certain embodiments, the disclosure provides methods of increasing susceptibility of a parasite to a drug by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same to the parasite in an amount and for a time sufficient to increase the amount of the drug in the parasite as compared to the amount of the drug that would be present in the absence of the rifamycin, rifamycin derivative, rifampicin, rifampicin derivative, or pharmaceutically acceptable salt, hydrate, or prodrug thereof, or combination thereof, or composition comprising same, and administering the drug to the parasite in an amount and for a time sufficient to inhibit the parasite.

According to certain embodiments, the disclosure provides methods of increasing susceptibility of a parasite to a drug by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same to an organism susceptible to infection by the parasite in an amount and for a time sufficient to increase the amount of the drug in the parasite as compared to the amount of the drug that would be present in the absence of the rifamycin, rifamycin derivative, rifampicin, rifampicin derivative, or pharmaceutically acceptable salt, hydrate, or prodrug thereof, or combination thereof, or composition comprising same and administering the drug to organism susceptible to infection by the parasite in an amount and for a time sufficient to inhibit the parasite.

According to certain embodiments, the disclosure provides methods of increasing susceptibility of a parasite to a drug by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same to an organism susceptible to infection by the parasite in an amount and for a time sufficient to increase the amount of the drug in the parasite as compared to the amount of the drug that would be present in the absence of the rifamycin, rifamycin derivative, rifampicin, rifampicin derivative, or pharmaceutically acceptable salt, hydrate, or prodrug thereof, or combination thereof, or composition comprising same, and administering the drug to organism susceptible to infection by the parasite in an amount and for a time sufficient to inhibit the parasite.

According to certain embodiments, the disclosure provides methods of inhibiting a parasite to a drug by administering rifamycin, a rifamycin derivative, such as rifabutin or a rifabutin derivative, rifampicin, a rifampicin derivative, or a pharmaceutically acceptable salt, hydrate, or prodrug thereof, or a combination thereof, or a composition comprising same, to the parasite in an amount and for a time sufficient to inhibit the parasite.

The following abbreviations are used throughout the specification: RTI-x—designates a rifamycin derivative in which "x" is replaced by an identification number used in the present specification to designate a particular composition.

DETAILED DESCRIPTION

Figure 1A:
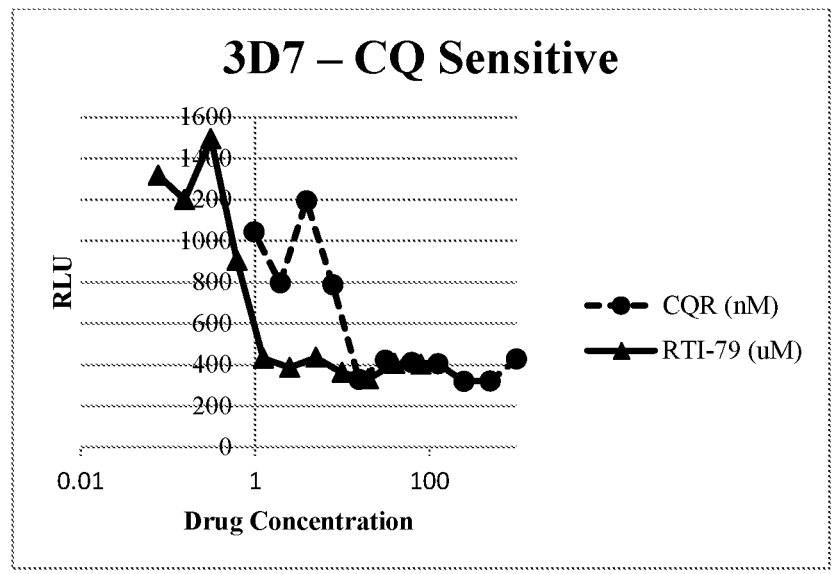
FIG. 1A is a graph of the dose response curves of chloroquine-sensitive 3D7 P. falciparum to chloroquine (CQR) and RTI-79 according to an exemplary embodiment of the present disclosure.

The present disclosure relates to compositions and methods for inhibition and/or drug-sensitization of a parasite. These compositions and methods are described in further detail below.

Unless otherwise indicated by the specific context of this specification a parasite can include any type of parasite or any part thereof. Furthermore, it can include a parasite in a host organism, or outside a host organism, such as in the environment occupied by an organism susceptible to infection by the parasite. The organism or host organism can be any animal. By way of example, and not limitation, the organism or host organism can be a mammal, such as a human, a pet mammal such as a dog or cat, an agricultural mammal, such as a horse, cow, pig, sheep, or goat, or a zoo mammal.

Although many embodiments herein are described with reference to a single parasite, the present disclosure is not so limited. The present disclosure encompasses, for example, infections of a single host animal with a plurality of parasites of the same species and with a plurality of parasites of different species, concurrently or otherwise. These embodiments and others will be readily apparent to one of ordinary skill in the art in view of the present disclosure.

Drug-sensitization, unless otherwise indicated by the specific context of this specification, can include increased sensitivity to a drug, decreased resistance to a drug, or potentiation of a drug's activity or efficacy. Any effect can be measured using any methods accepted in the art. In certain embodiments, drug-sensitization can be determined by an increased ability of the drug to inhibit a parasite. Parasitic inhibition can include killing the parasite, rendering the parasite more susceptible to the immune system of a host organism, arresting the parasite in a phase of its life cycle that is relatively benign with respect to the host organism, reducing the rate of propagation of the parasite in the host organism, or otherwise negatively affecting a parasite. An increased ability of the drug to inhibit a parasite can be demonstrated by, for example, an ability to inhibit the cell with a reduced amount of drug or in a shorter period of time than in the absence of drug-sensitization. In the case of drug-resistant parasites, which include parasites with inherent or acquired resistance, drug-sensitization can result in a renewed, restored, restored or newly acquired ability of the drug to inhibit a parasite or type of parasite.

Administration to a parasite, unless otherwise indicated by the specific context of this specification, can include administration directly to a parasite or indirect administration to a parasite, such as by direct or indirect administration to a host organism infected by the parasite or by prophylactic administration to an organism susceptible to infection by the parasite, or such as by administration to the environment of the parasite, such as by administration to an environment of the parasite. By way of example and not limitation, administration to a parasite can include, in addition to directly contacting the parasite with the composition administered, oral, enteral, and parenteral administration to an infected or susceptible host, as well as administration of the compound to a body of or source of water, for example, in which the parasite resides or will reside, as well as administration of the compound to a substrate or fomite upon which the parasite resides or will reside, or upon which another host or susceptible host organism resides or will reside, such as, for example, a mosquito netting, a portion of a plant such as a leaf, or a consumer product that can come into close contact with the skin of a human or animal, such as a bedsheet, a protective athletic garment, or a harness. By way of further example, the compositions of the present disclosure can be administered to a susceptible animal or infected host in the form of aerosolized particles, e.g., by way of aerosolizer, nebulizer or other like device, or transdermally, or transbucally, or sublingually, or by subcutaneous administration, or any other method of drug delivery, and any combination thereof.

Compositions

The present disclosure includes parasite drug-sensitization compositions, such as rifamycin, rifamycin derivatives, such as rifabutin or rifabutin derivatives, rifampicin, rifampicin derivatives, or pharmaceutically acceptable salts, hydrates, or prodrugs thereof, or combinations thereof. Other rifamycin derivatives include rifapentine and rifalazil.

In certain embodiments, the present disclosure provides derivatives of rifabutin according to one of the following general structures:

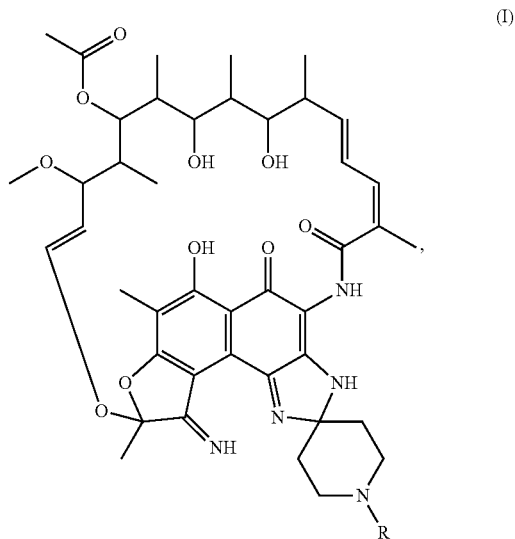

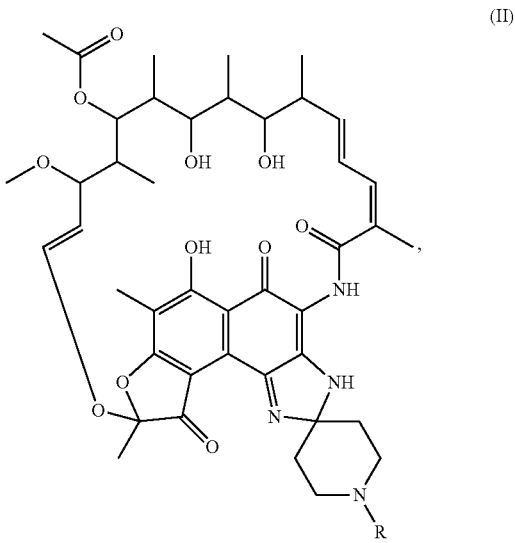

-continued
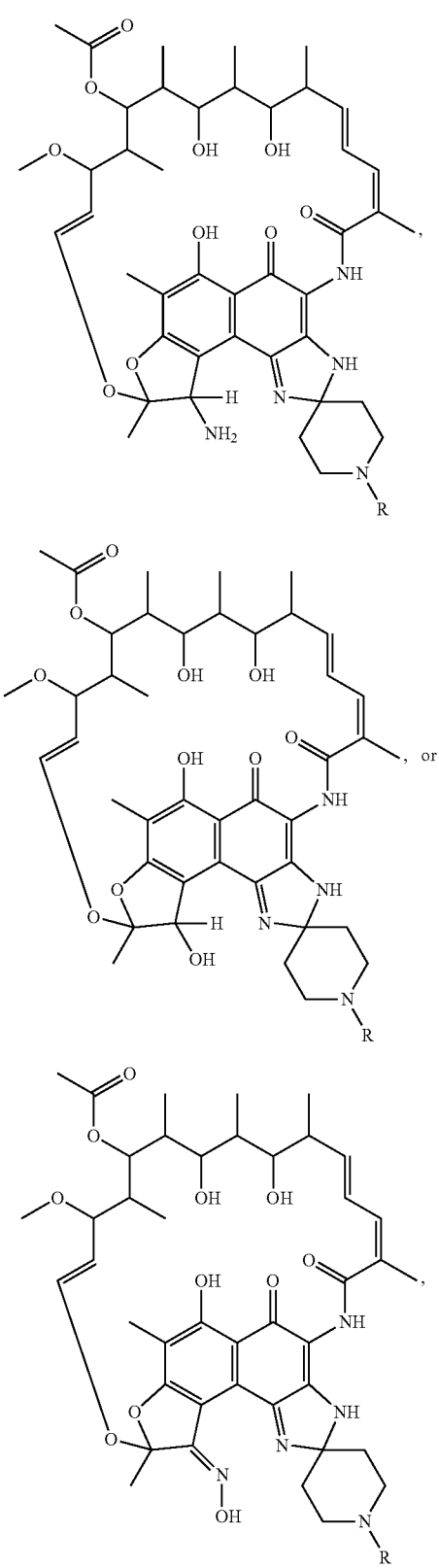
(III)
(IV)
(V)
in which R can be an alkyl, aryl, or hetero aryl group.
In additional or alternative embodiments, the present disclosure provides enantiomers of the general structures. In certain embodiments, it provides enantiomers with the following general chiral structures:
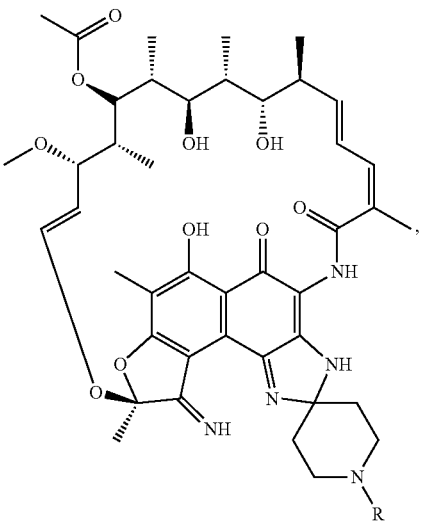
(Ia)
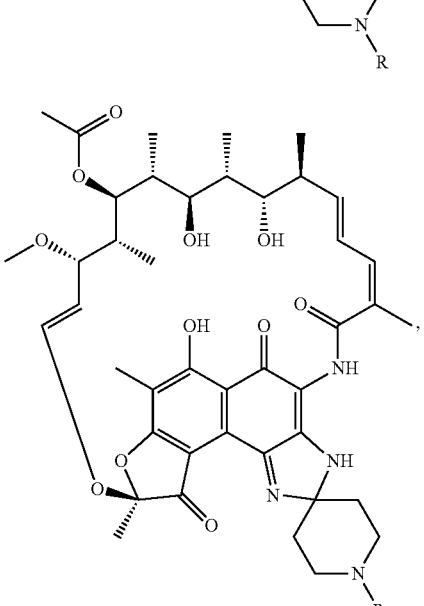
(IIa)
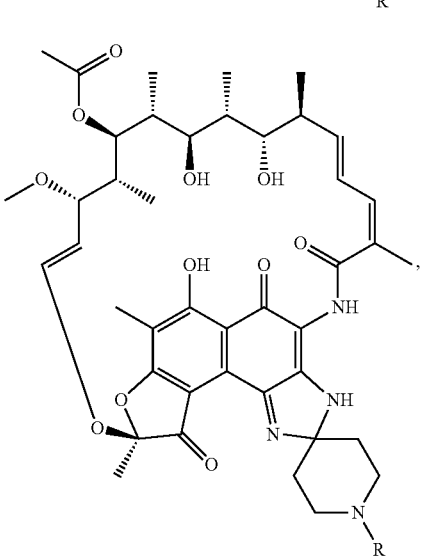
(IIIa)

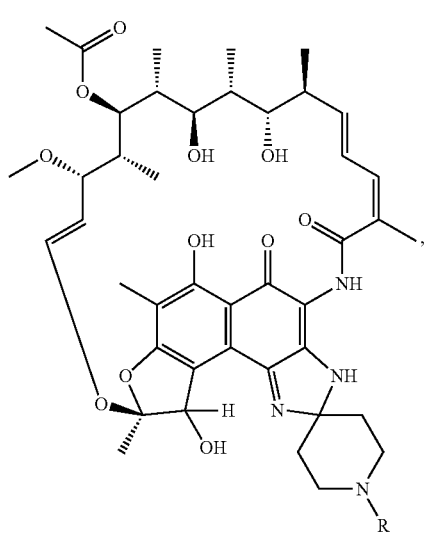

(IVa)

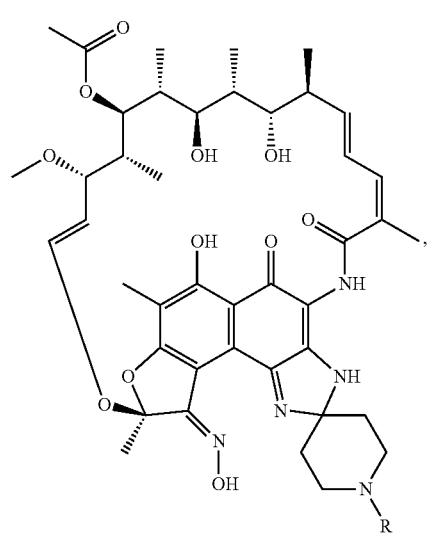

(Va)

in which R can be an alkyl, aryl, or hetero aryl group.

In certain embodiments having general structures I or II or general chiral structures Ia or IIa, R can be one of the following structures:

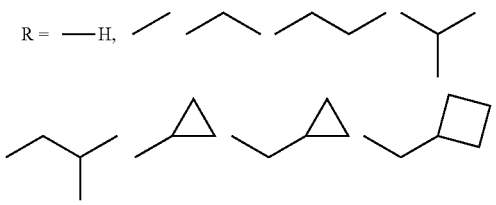

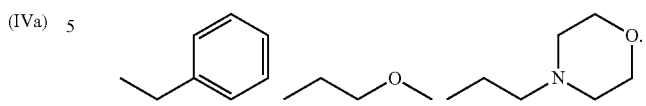

In certain embodiments, the present disclosure provides derivatives of rifabutin according to the following formula:

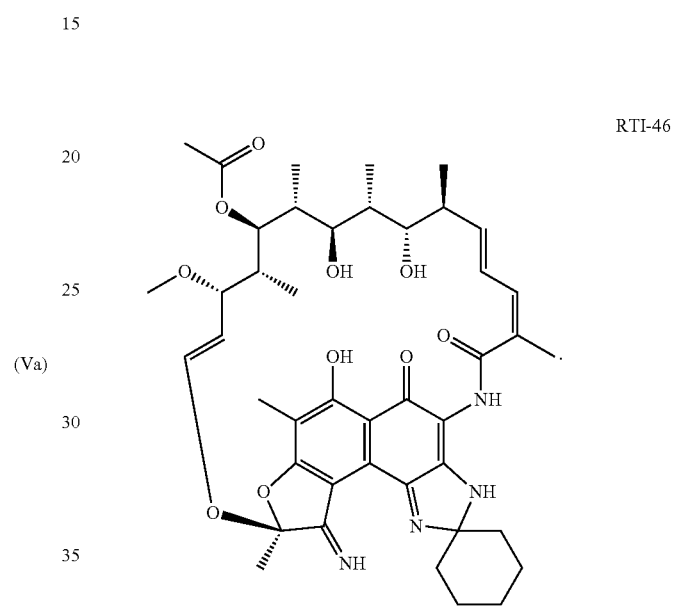

RTI-46

In certain embodiments, the present disclosure provides derivatives of rifabutin according to the following formula:

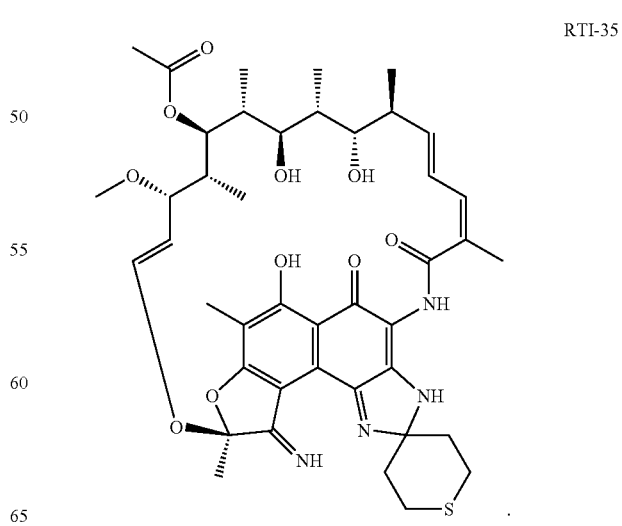

RTI-35

In certain embodiments, the present disclosure provides derivatives of rifabutin according to the following formula:

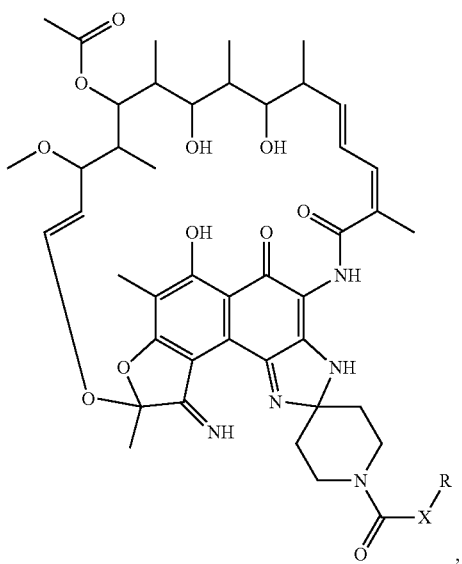

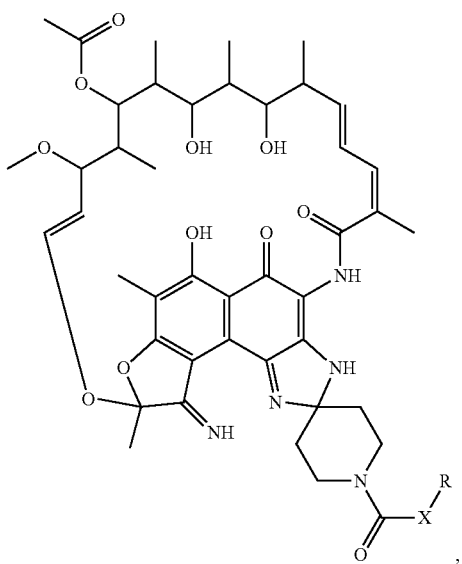

where X and R can include the following combinations:

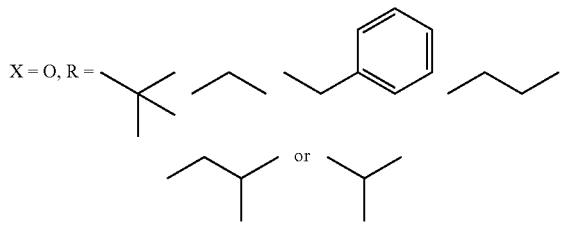

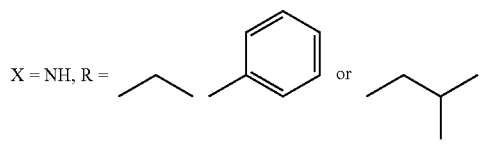

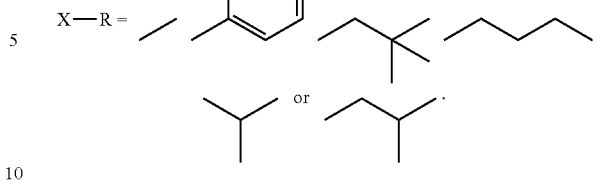

The structure with the general formula above can also be the following enantiomer:

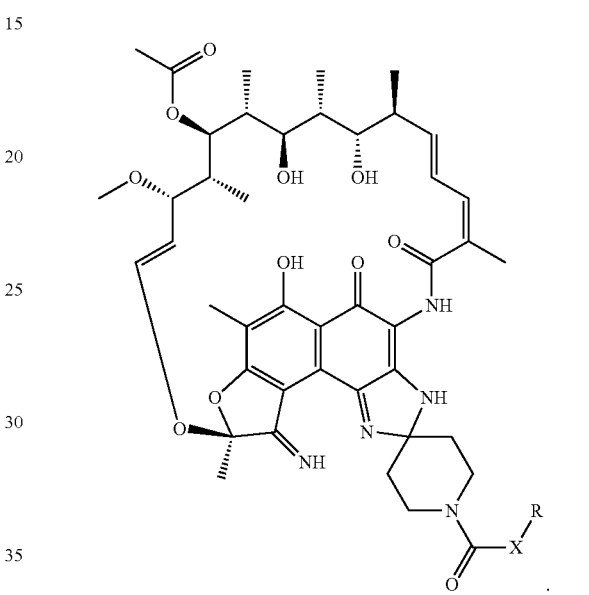

In certain embodiments, the present disclosure provides derivatives of rifabutin according to the following formula:

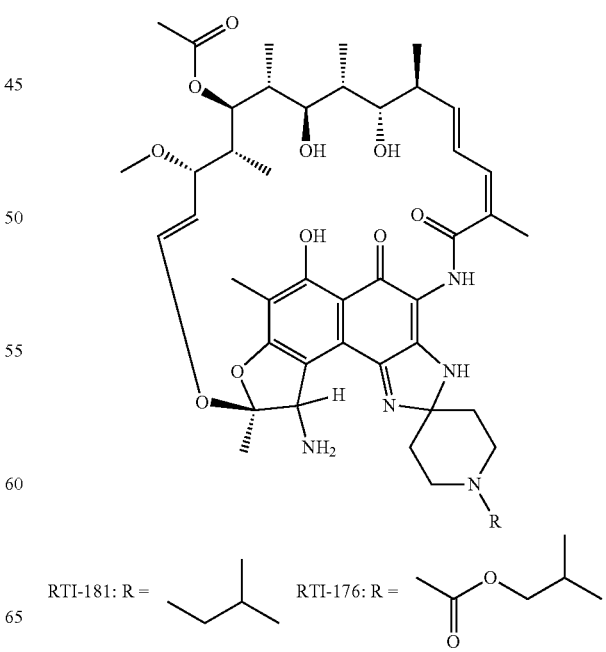

RTI-183: R = 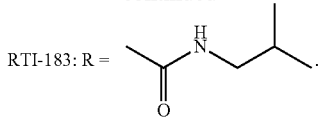

In certain embodiments having general structures III or IV or general chiral structures IIIa or IVa, R can be one of the following structures:

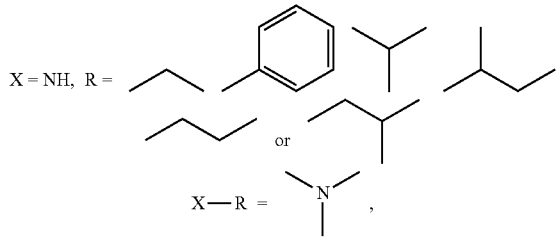

wherein X is a C, O, or N and R is an alkyl, aryl, or hetero-aryl group.

In another embodiment, the present disclosure provides derivatives of rifabutin according to the following formula:

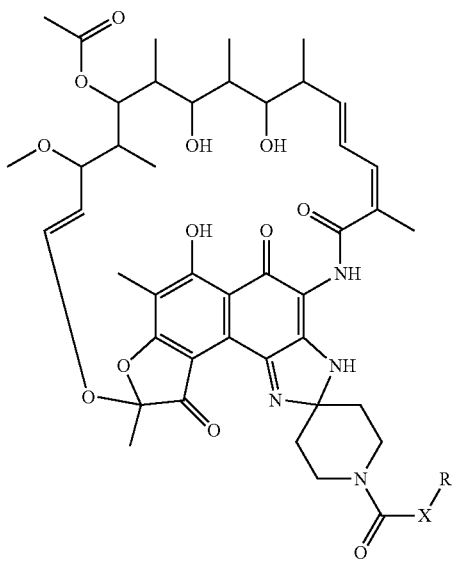

wherein X is a C, O, or N and R is an alkyl, aryl, or hetero-aryl group or wherein X and R are as follows:

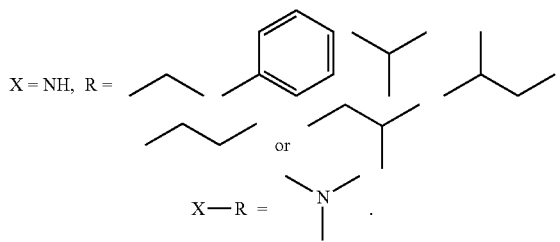

In certain embodiments, a composition of the general formula above can be the following enantiomer:

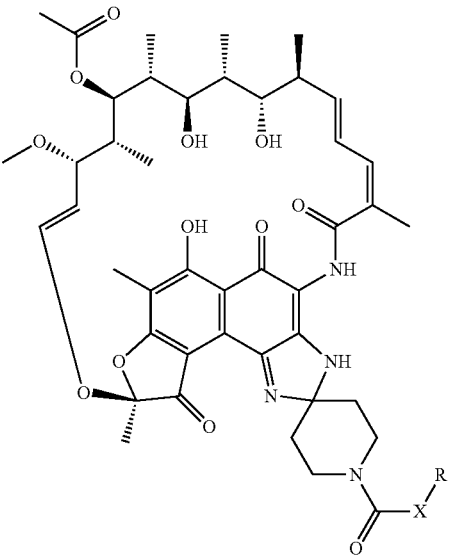

In certain embodiments, the present disclosure provides derivatives of rifabutin according to the following formula:

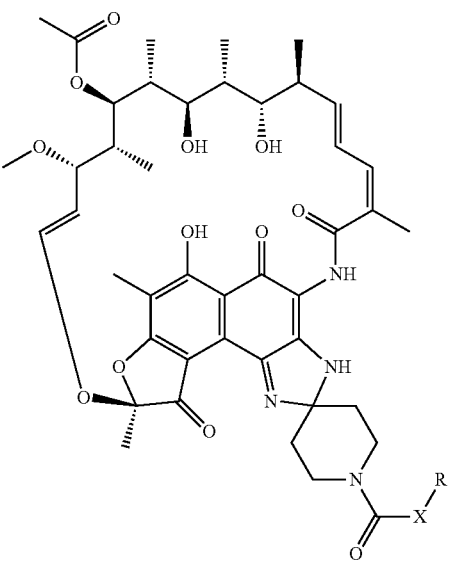

wherein X is a C, O, or N and R can include the structures listed below:

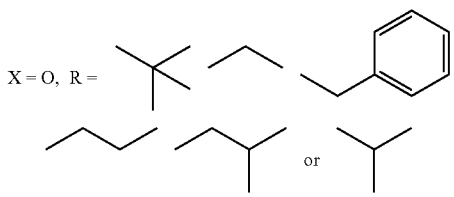

-continued

X—R = 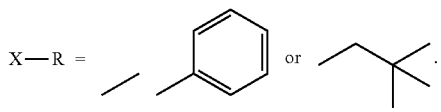

In certain embodiments, the present disclosure provides derivatives of rifabutin according to the following formula, wherein X is a C, O, or N:

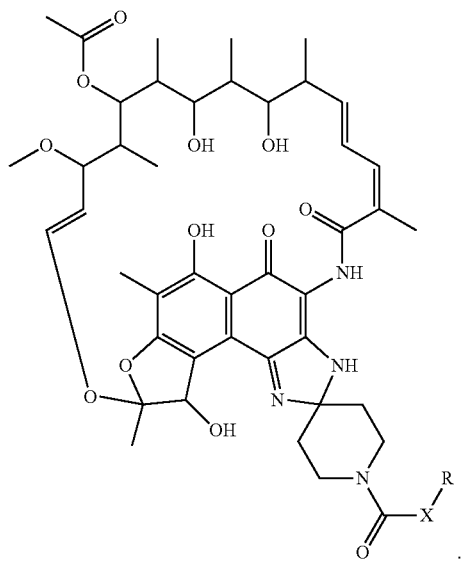

X = C, O, N

In certain embodiments, a composition with the general formula above can be the following enantiomer:

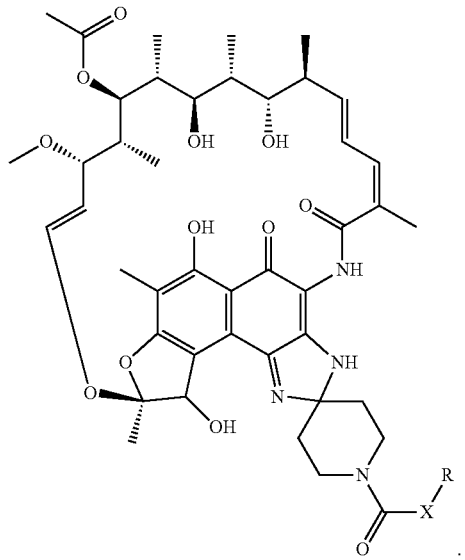

X = C, O, N

In certain embodiments, the present disclosure provides derivatives of rifabutin according to the following formula:

RTI-175

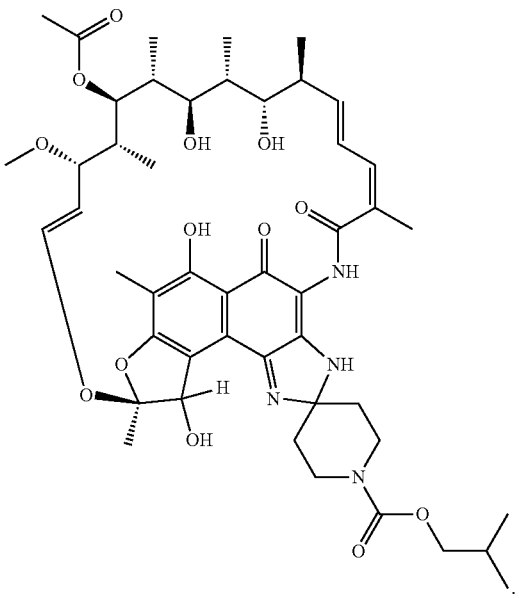

In certain embodiments, the present disclosure provides derivatives of rifabutin according to the following formula:

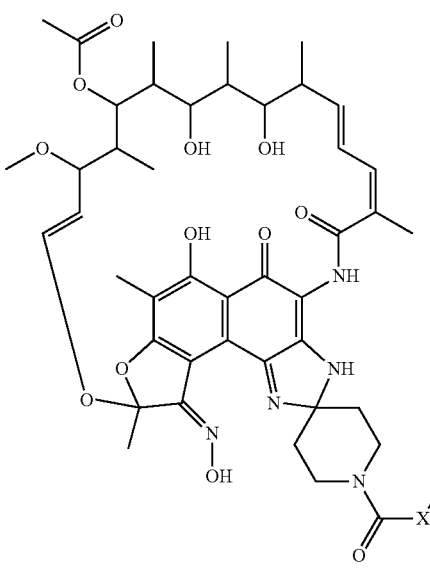

wherein X is a C, O, or N and R is an alkyl, aryl, or hetero-aryl group or wherein X and R are as follows:

X = O, R = 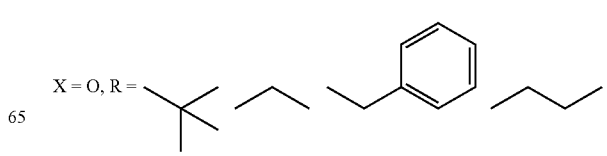

17

-continued

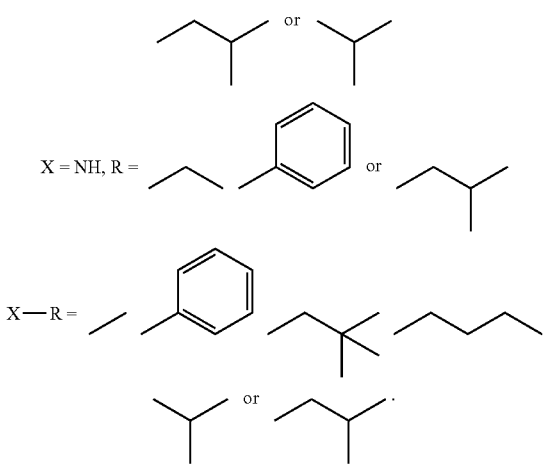

In certain embodiments, the present disclosure provides derivatives of rifabutin according to the following formula:

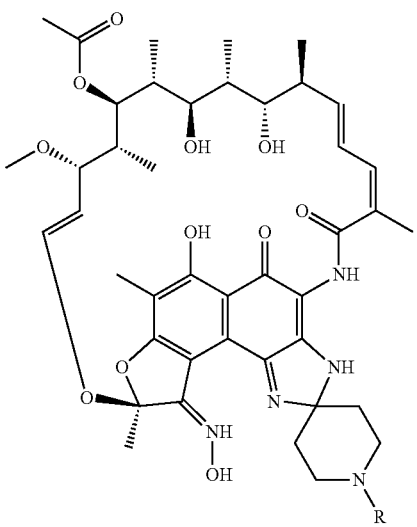

RTI-197: R = 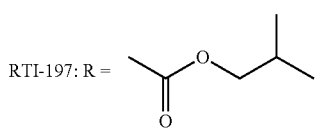

RTI-217: R = 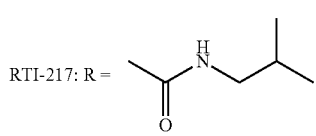

In other embodiments, the present disclosure provides a drug-sensitization composition including a series of 3,4-cyclo-rifamycin derivatives. Examples of such compositions are as follows:

18

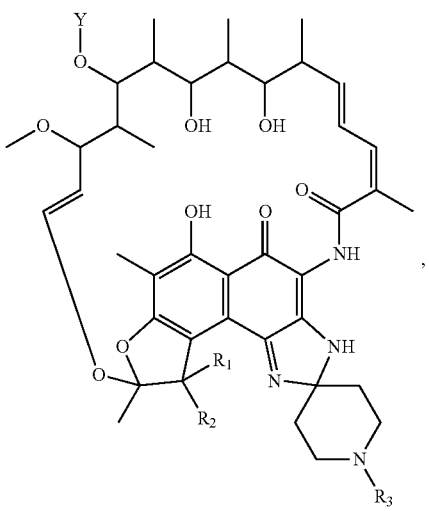

or the following enantiomer:

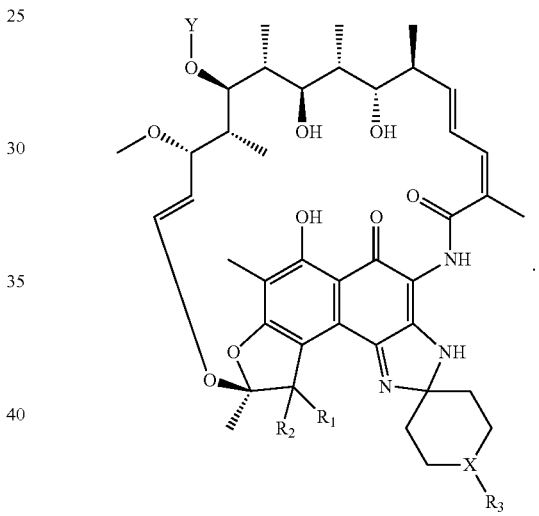

In certain embodiments X can be CH, S, SO, SO$_2$ or N. Y can be H or an acetyl group. R1 can be hydrogen. R2 can be a hydroxyl or an amino (—NH$_2$) group. R1 and R2 together can be an oxo or imine group. R3 can be one of the following groups: hydrogen, alkyl, alkenyl, alkynyl, cycloalkyl, aryl, heteroaryl and heterocycloalkyl groups that can be additionally substituted with from zero to four substituents chosen independently from halogen, hydroxyl, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy, and benzyloxy. In certain embodiments, R3 can be —C(=O)—R4, —C(=O)—O—R4 and —C(=O)—NH—R4 where R4 is independently selected from alkyl, alkenyl, alkynyl, cycloalkyl, aryl, heteroaryl and heterocycloalkyl groups that can be additionally substituted with from zero to four substituents chosen independently from halogen, hydroxyl, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy and benzyloxy.

In other embodiments the present invention provides compositions of the following structure:

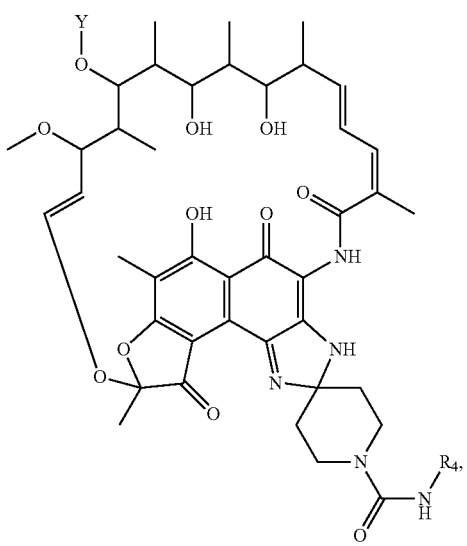

or the following enantiomer:

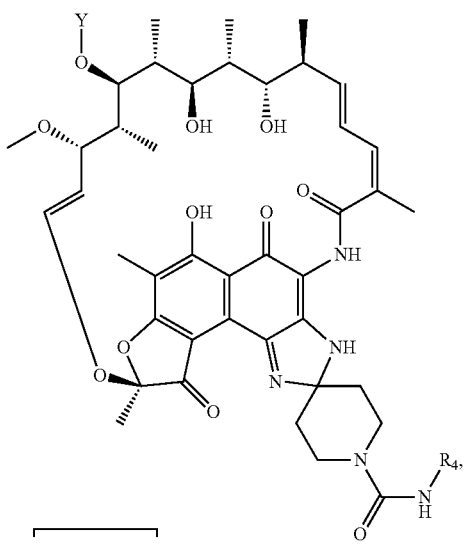

wherein Y is H or an acetyl group and R4 can be selected from alkyl, alkenyl, alkynyl, cycloalkyl, aryl, heteroaryl and heterocycloalkyl groups that can be additionally substituted with from zero to four substituents chosen independently from halogen, hydroxyl, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy and benzyloxy.

In certain embodiments, the present invention provides compositions with the following structure:

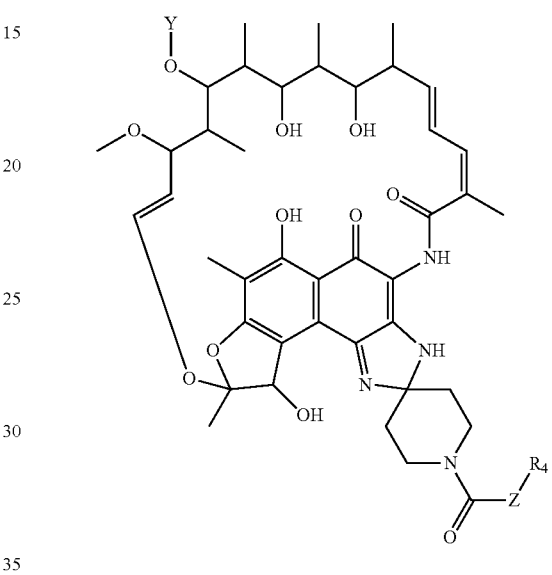

wherein Y is H, or acetyl group; Z is carbon, oxygen or nitrogen atom; and R4 is independently selected from alkyl, alkenyl, alkynyl, cycloalkyl, aryl, heteroaryl and heterocycloalkyl groups that can be additionally substituted with from zero to four substituents chosen independently from halogen, hydroxyl, alkoxy-alkyl, —CN, nitro, —S-alkyl, amino, alkylamino, dialkylamino, dialkylaminoalkyl, carboxy, carboalkoxy, acyl, carboxamido, alkylsulfoxide, acylamino, phenyl, benzyl, phenoxy and benzyloxy.

Examples of parasite sensitization compositions in accordance with certain embodiments of the present disclosure can include those listed in Table 1. Compositions of Table 1 are designated by like names throughout this specification.

TABLE 1

| | | Rifamycin Derivatives | |
|---|---|---|---|
| RTI-x | General structure | R | Name |
| 33 | I | 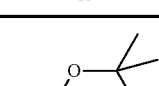 | 11-deoxy-11-imino-4-deoxy-3,4[2-spiro-[1-(t-butyloxycarbonyl)-piperidin-4-yl]]-(1H)-imidazo-(2,5-dihydro)rifamycin S |
| 44 | I | —H | 11-deoxy-11-imino-4-deoxy-3,4[2-spiro-[piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 49 | I | benzyl (CH2-phenyl) | 11-deoxy-11-imino-4-deoxy-3,4[2-spiro-[1-(benzyl)-piperidin-4-yl]]-(1H)-imidazo-(2,5-dihydro)rifamycin S |
| 51 | I | CH2CH2OCH3 | 11-deoxy-11-imino-4-deoxy-3,4[2-spiro-[1-(2-methoxyethyl)-piperidin-4-yl]]-(1H)-imidazo-(2,5-dihydro)rifamycin S |
| 53 | I | 2-morpholinoethyl | 11-deoxy-11-imino-4-deoxy-3,4[2-spiro-[1-(2-morpholinoethyl)-piperidin-4-yl]]-(1H)-imidazo-(2,5-dihydro)rifamycin S |
| 57 | I | cyclobutylmethyl | 11-deoxy-11-imino-4-deoxy-3,4[2-spiro-[1-(cyclobutylmethyl)-piperidin-4-yl]]-(1H)-imidazo-(2,5-dihydro)rifamycin S |
| 59 | I | cyclopropylmethyl | 11-deoxy-11-imino-4-deoxy-3,4[2-spiro-[1-(cyclopropylmethyl)-piperidin-4-yl]]-(1H)-imidazo-(2,5-dihydro)rifamycin S |
| 60 | I | isopropyl | 11-deoxy-11-imino-4-deoxy-3,4[2-spiro-[1-(isopropyl)-piperidin-4-yl]]-(1H)-imidazo-(2,5-dihydro)rifamycin S |
| 61 | I | -C(=O)OCH2CH3 | 11-deoxy-11-imino-4-deoxy-3,4[2-spiro-[1-(t-ethyloxycarbonyl)-piperidin-4-yl]]-(1H)-imidazo-(2,5-dihydro)rifamycin S |
| 63 | I | -C(=O)CH3 | 11-deoxy-11-imino-4-deoxy-3,4[2-spiro-[1-(acetyl)-piperidin-4-yl]]-(1H)-imidazo-(2,5-dihydro)rifamycin S |
| 64 | I | n-propyl | 11-deoxy-11-imino-4-deoxy-3,4[2-spiro-[1-(n-propyl)-piperidin-4-yl]]-(1H)-imidazo-(2,5-dihydro)rifamycin S |
| 65 | I | cyclopropyl | 11-deoxy-11-imino-4-deoxy-3,4[2-spiro-[1-(cyclopropyl)-piperidin-4-yl]]-(1H)-imidazo-(2,5-dihydro)rifamycin S |
| 66 | I | ethyl | 11-deoxy-11-imino-4-deoxy-3,4[2-spiro-[1-(ethyl)-piperidin-4-yl]]-(1H)-imidazo-(2,5-dihydro)rifamycin S |
| 67 | I | -C(=O)-phenyl | 11-deoxy-11-imino-4-deoxy-3,4[2-spiro-[1-(beRTIoyl)-piperidin-4-yl]]-(1H)-imidazo-(2,5-dihydro)rifamycin S |
| 68 | I | -C(=O)OCH2-phenyl | 11-deoxy-11-imino-4-deoxy-3,4[2-spiro[1-(benzyloxycarbonyl)-piperidin-4-yl]]-(1H)-imidazo-(2,5-dihydro)rifamycin S |
| 69 | I | —CH3 | 11-deoxy-11-imino-4-deoxy-3,4[2-spiro-[1-(methyl)-piperidin-4-yl]]-(1H)-imidazo-(2,5-dihydro)rifamycin S |
| 70 | I | 2-methylpropyl | 11-deoxy-11-imino-4-deoxy-3,4[2-spiro-[1-(2-methylpropyl)-piperidin-4-yl]]-(1H)-imidazo-(2,5-dihydro)rifamycin S |
| 74 | I | -C(=O)NH-phenyl | 11-deoxy-11-imino-4-deoxy-3,4[2-spiro-[1-(phenylaminocarbonyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 75 | II | | 4-deoxy-3,4[2-spiro-[1-(t-butyloxycarbonyl)-piperidin-4-yl]]-(1H)-imidazo-(2,5-dihydro)rifamycin S |
| 76 | II | | 4-deoxy-3,4[2-spiro-[1-(ethyloxycarbonyl)-piperidin-4-yl]]-(1H)-imidazo-(2,5-dihydro)rifamycin S |
| 77 | I | | 11-deoxy-11-imino-4-deoxy-3,4[2-spiro-[1-(ethyloxycarbonyl)-piperidin-4-yl]]-(1H)-imidazo-(2,5-dihydro)rifamycin S |
| 78 | II | | 4-deoxy-3,4[2-spiro[1-(n-propyloxycarbonyl)-piperidin-4-yl]]-(1H)-imidazo-(2,5-dihydro)rifamycin S |
| 79 | II | | 4-deoxy-3,4[2-spiro-[1-(isobutyloxycarbonyl)-piperidin-4-yl]]-(1H)-imidazo-(2,5-dihydro)rifamycin S |
| 80 | II | | 4-deoxy-3,4[2-spiro-[1-(benzyloxycarbonyl)-piperidin-4-yl]]-(1H)-imidazo-(2,5-dihydro)rifamycin S |
| 81 | I | | 11-deoxy-11-imino-4-deoxy-3,4[2-spiro-[1-(isobutyloxycarbonyl)-piperidin-4-yl]-(1H)-imidazo-(2,5-dihydro)rifamycin S |
| 82 | I | | 11-deoxy-11-imino-4-deoxy-3,4[2-spiro-[1-(ethylaminocarbonyl)-piperidin-4-yl]]-(1H)-imidazo(2,5-dihydro)rifamycin S |
| 83 | II | | 4-deoxy-3,4[2-spiro-[1-(ethylaminocarbonyl)-piperidin-4-yl]]-(1H)-imidazo-(2,5-dihydro)rifamycin S |
| 84 | I | | 11-deoxy-11-imino-4-deoxy-3,4[2-spiro-[1-(isopropyloxycarbonyl)-piperidin-4-yl]]-(1H)-imidazo-(2,5-dihydro)rifamycin S |
| 85 | II | | 4-deoxy-3,4[2-spiro-[1-(isopropyloxycarbonyl)-piperidin-4-yl]]-(1H)-imidazo-(2,5-dihydro)rifamycin S |
| 86 | II | | 4-deoxy-3,4[2-spiro-[1-(phenylaminocarbonyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 87 | II | (acetyl group) | 4-deoxy-3,4[2-spiro-[1-(acetyl)-piperidin-4-yl]]-(1H)-imidazo-(2,5-dihydro)rifamycin S |
| 88 | II | (benzoyl group) | 4-deoxy-3,4[2-spiro-[1-(beRTIoyl)-piperidin-4-yl]]-(1H)-imidazo-(2,5-dihydro)rifamycin S |
| 89 | II | (3,3-dimethylbutanoyl group) | 4-deoxy-3,4[2-spiro-[1-(3,3-dimethylbutanoyl)-piperidin-4-yl]]-(1H)-imidazo-(2,5-dihydro)rifamycin S |
| 91 | I | (3,3-dimethylbutanoyl group) | 11-deoxy-11-imino-4-deoxy-3,4[2-spiro-[1-(3,3-dimethylbutanoyl)-piperidin-4-yl]]-(1H)-imidazo-(2,5-dihydro)rifamycin S |
| 94 | I | (n-pentanoyl group) | 11-deoxy-11-imino-4-deoxy-3,4[2-spiro-[1-(n-pentanoyl)-piperidin-4-yl]]-(1H)-imidazo-(2,5-dihydro)rifamycin S |
| 97 | I | (2-methylpropanoyl group) | 11-deoxy-11-imino-4-deoxy-3,4[2-spiro-[1-(2-methylpropanoyl)-piperidin-4-yl]]-(1H)-imidazo-(2,5-dihydro)rifamycin S |
| 98 | I | (3-methylbutanoyl group) | 11-deoxy-11-imino-4-deoxy-3,4[2-spiro-[1-(3-methylbutanoyl)-piperidin-4-yl]]-(1H)-imidazo-(2,5-dihydro)rifamycin S |
| 101 | II | (dimethylaminocarbonyl group) | 4-deoxy-3,4[2-spiro-[1-(dimethylaminocarbonyl)-piperidin-4-yl]]-(1H)-imidazo-(2,5-dihydro)rifamycin S |
| 102 | II | (isobutylaminocarbonyl group) | 4-deoxy-3,4[2-spiro-[1-(isobutylaminocarbonyl)-piperidin-4-yl]]-(1H)-imidazo-(2,5-dihydro)rifamycin S |
| 103 | II | (isopropylaminocarbonyl group) | 4-deoxy-3,4[2-spiro-[1-(isopropylaminocarbonyl)-piperidin-4-yl]]-(1H)-imidazo-(2,5-dihydro)rifamycin S |
| 104 | II | ((1-methylpropyl)aminocarbonyl group) | 4-deoxy-3,4[2-spiro-[1-((1-methylpropyl) aminocarbonyl)-piperidin-4-yl]]-(1H)-imidazo-(2,5-dihydro)rifamycin S |

TABLE 1-continued

Rifamycin Derivatives

| RTI-x | General structure | R | Name |
|---|---|---|---|
| 105 | II | | 4-deoxy-3,4[2-spiro-[1-(t-butylaminocarbonyl)-piperidin-4-yl]]-(1H)-imidazo-(2,5-dihydro)rifamycin S |
| 174 | IV | | 11-deoxy-11-hydroxy-4-deoxy-3,4[2-spiro-[1-(2-methylpropyl)-piperidin-4-yl]]-(1H)-imidazo-(2,5-dihydro)rifamycin S |
| 175 | IV | | 11-deoxy-11-hydroxy-4-deoxy-3,4[2-spiro-[1-(isobutyloxycarbonyl)-piperidin-4-yl]]-(1H)-imidazo-(2,5-dihydro)rifamycin S |
| 176 | III | | 11-deoxy-11-amino-4-deoxy-3,4[2-spiro-[1-(isobutyloxycarbonyl)-piperidin-4-yl]]-(1H)-imidazo-(2,5-dihydro)rifamycin S |
| 181 | III | | 11-deoxy-11-amino-4-deoxy-3,4[2-spiro-[1-(2-methylpropyl)-piperidin-4-yl]]-(1H)-imidazo-(2,5-dihydro)rifamycin S |
| 182 | I | | 11-deoxy-11-imino-4-deoxy-3,4[2-spiro-[1-(isobutylaminocarbonyl)-piperidin-4-yl]]-(1H)-imidazo-(2,5-dihydro)rifamycin S |
| 183 | III | | 11-deoxy-11-amino-4-deoxy-3,4[2-spiro-[1-(isobutylaminocarbonyl)-piperidin-4-yl]]-(1H)-imidazo-(2,5-dihydro)rifamycin S |
| 197 | V | | 11-deoxy-11-hydroxyimino-4-deoxy-3,4[2-spiro-[1-(isobutyloxycarbonyl)-piperidin-4-yl]]-(1H)-imidazo-(2,5-dihydro)rifamycin S |
| 217 | V | | 11-deoxy-11-hydroxyimino-4-deoxy-3,4[2-spiro-[1-(isobutylaminocarbonyl)-piperidin-4-yl]]-(1H)-imidazo-(2,5-dihydro)rifamycin S |

Modification of the rifamycin structure in locations corresponding to the 21-OH 23-OH or 25-O—Ac sites of the rifabutin structures I, II, III, IV and V do not generally affect drug-sensitization activity and thus variations with modifications at these sites or even elimination of these sites are encompassed herein. Such variations can be used to improve synthesis yields, control costs, increase water solubility, or improve pharmaceutical properties of the composition. Sites 21, 23 and 25 are located as follows:

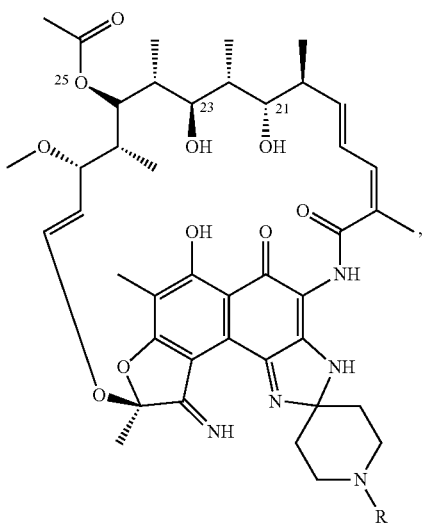

(I)

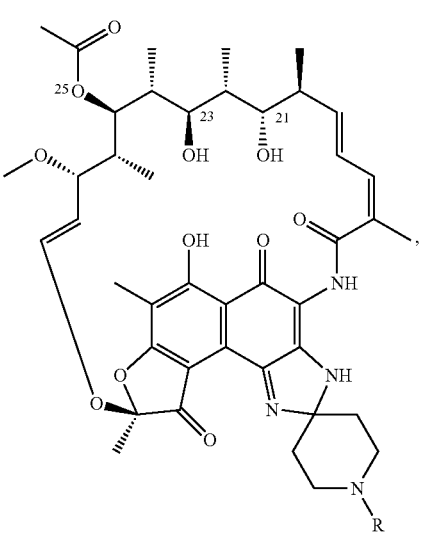

(II)

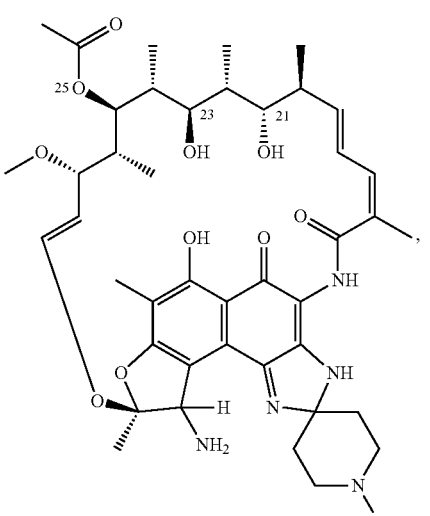

(III)

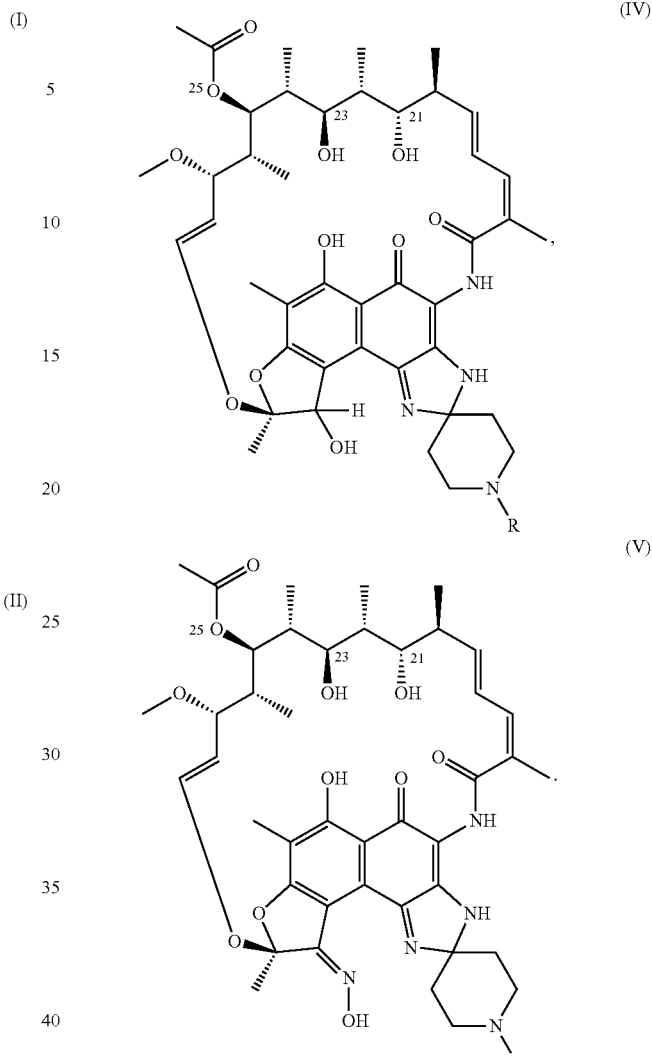

The present disclosure also includes pharmaceutically acceptable salts, hydrates, prodrugs, and mixtures of any of the above compositions. The term "pharmaceutically acceptable salt" refers to salts whose counter ion derives from pharmaceutically acceptable non-toxic acids and bases.

The 3,4-cyclo-rifamycin derivatives which contain a basic moiety, such as, but not limited to an amine or a pyridine or imidazole ring, can form salts with a variety of organic and inorganic acids. Suitable pharmaceutically acceptable (i.e., non-toxic, physiologically acceptable) base addition salts for the compounds of the present invention include inorganic acids and organic acids. Examples include acetate, adipate, alginates, ascorbates, aspartates, benzenesulfonate (besylate), benzoate, bicarbonate, bisulfate, borates, butyrates, carbonate, camphorsulfonate, citrate, digluconates, dodecylsulfates, ethanesulfonate, fumarate, gluconate, glutamate, glycerophosphates, hemisulfates, heptanoates, hexanoates, hydrobromides, hydrochloride, hydroiodides, 2-hydroxyethanesulfonates, isethionate, lactate, maleate, malate, mandelate, methanesulfonate, 2-naphthalenesulfonates, nicotinates, mucate, nitrate, oxalates, pectinates, persulfates, 3-phenylpropionates, picrates, pivalates, propionates, pamoate, pantothenate, phosphate, salicylates, succinate, sulfate, sulfonates, tartrate, p-toluenesulfonate, and the like.

The 3,4-cyclo-rifamycin derivatives which contain an acidic moiety, such as but not limited to a carboxylic acid, can form salts with variety of organic and inorganic bases. Suitable pharmaceutically acceptable base addition salts for the compounds of the present invention include, but are not limited to, ammonium salts, metallic salts made from calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine), t-butylamine, dicyclohexylamine, hydrabamine and procaine.

The 3,4-cyclo-rifamycin derivatives, and salts thereof, can exist in their tautomeric form (for example, as an amide or imino ether). All such tautomeric forms are contemplated herein as part of the present invention.

The compounds described herein can contain asymmetric centers and can thus give rise to enantiomers diastereomers and other stereoisomeric forms. Each chiral center can be defined in terms of absolute stereochemistry, as (R)- or (S)-. The present invention is meant to include all such possible isomers, as well as, their racemic and optically pure forms. Optically active (R)- and (S)-, or (D)- and (L)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The configuration of any carbon-carbon double bond appearing herein is selected for convenience only and unless explicitly stated, is not intended to designate a particular configuration. Thus the carbon-carbon double bond depicted arbitrarily above as E can be Z, E, or a mixture of the two in any proportion.

Abbreviations as used herein have the meanings known by one skilled in the art. Specifically, Ac represent acetyl group, Boc represents t-butoxycarbonyl group Bn represents benzyl group, DCM represents dichloromethane, DMF represents N,N-dimethylformamide, DMSO represents dimethyl sulfoxide, Et represents ethyl group, EtOAc represents ethylacetate, Me represents methyl group, Ph represents phenyl group, TEA represents trimethylamine, TFA represents trifluoroacetic acid, THF represents tetrahydrofuran, and TMS is trimethylsilane group.

Compositions of the present disclosure can also include a pharmaceutically acceptable carrier, in particular a carrier suitable for the intended mode of administration, or salts, buffers, or preservatives. Rifamycin and many of its derivatives, such as rifabutin and rifabutin derivatives are poorly soluble in water. Accordingly, aqueous compositions of the present disclosure can include solubility enhancers. Compositions for oral use can include components to enhance intestinal absorption. The overall formulation of the compositions can be based on the intended mode of administration. For instance, the composition can be formulated as a pill or capsule for oral ingestion. It can also be separately encapsulated.

Compositions of the present disclosure can contain a sufficient amount of rifamycin or rifamycin derivative, such as rifabutin or a rifabutin derivative, or rifampicin or a rifampicin derivative, or a pharmaceutically acceptable salt, hydrate, or prodrug thereof, or a combination thereof, to cause drug-sensitization to occur when the composition is administered to a parasite. The amount can vary depending on other components of the composition and their effects on drug availability in a patient, the type of drug or drugs to which the parasite is sensitized, the amount of drug otherwise required to inhibit the parasite, the intended mode of administration, the intended schedule for administration, any drug toxicity concerns, drug-drug interactions, such as interactions with other medications administered to the host or susceptible organism, or the individual response of a host or susceptible organism. Many compositions can contain an amount of rifamycin or rifamycin derivative, such as rifabutin or a rifabutin derivative, or rifampicin or a rifampicin derivative, or a pharmaceutically acceptable salt, hydrate, or prodrug thereof, or a combination thereof, well below levels at which toxicity to the host or susceptible organism becomes a concern.

Compositions of the present disclosure can also contain one or more drugs for which the rifamycin or rifamycin derivative, such as rifabutin or a rifabutin derivative, or rifampicin or a rifampicin derivative, or a pharmaceutically acceptable salt, hydrate, or prodrug thereof, or a combination thereof, causes drug-sensitization. Example drugs are described in the current specification. In certain embodiments, compositions of the present disclosure can contain one or more other drugs commonly used in combination with the drug for which sensitization occurs. For example, a composition can include rifamycin or rifamycin derivative, such as rifabutin or a rifabutin derivative, or rifampicin or a rifampicin derivative, or a pharmaceutically acceptable salt, hydrate, or prodrug thereof, or a combination thereof, with any avermectin drug, regardless of whether rifabutin causes drug-sensitization for that drug.

Compositions of the present disclosure can further include other therapeutic agents. For example, they can include any one or more of the anti-parasite agents listed herein, such as those described below in connection with Parasite Drug Sensitization Methods. The amounts of those chemotherapeutic agents in compositions of the present disclosure can be reduced as compared to normal doses of such agents administered in a similar fashion.

The amount of rifamycin or rifamycin derivative, such as rifabutin or a rifabutin derivative, or rifampicin or a rifampicin derivative, or a pharmaceutically acceptable salt, hydrate, or prodrug thereof, or a combination thereof, present in a composition can be measured in any of a number of ways. The amount may, for example, express concentration or total amount. Concentration can be for example, weight/weight, weight/volume, moles/weight, or moles/volume. Total amount can be total weight, total volume, or total moles. Typically, the amount can be expressed in a manner standard for the type of formulation or dosing regimen used.

The present disclosure further includes methods of identifying whether a rifamycin derivative, such as rifabutin or a rifabutin derivative, or rifampicin or a rifampicin derivative, or a pharmaceutically acceptable salt, hydrate, or prodrug thereof, or a combination thereof, is able to sensitize a parasite to a drug. Such methods include preparing or obtaining such a derivative, applying it to a parasite, and identifying that the derivative renders the parasite more susceptible to the drug in any manner described herein.

Parasite Drug Sensitization and Inhibition Methods

The present disclosure also includes drug-sensitization and/or inhibition methods in which a composition comprising rifamycin or a rifamycin derivative, such as rifabutin or a rifabutin derivative, or rifampicin or a rifampicin derivative, or a pharmaceutically acceptable salt, hydrate, or prodrug thereof, or a combination thereof, is administered to a parasite in order to sensitize the parasite to another drug or combination of drugs and/or to inhibit the parasite. The composition can be any composition described above. In certain embodiments, the composition can be administered with any other drug or drugs which can alternatively be present in a pharmaceutical composition as described herein. For example, the other drug can include ivermectin.

In methods in which a parasite is sensitized to a drug or drugs, the drug or drugs can be any drug or drugs for which rifamycin or a rifamycin derivative, such as rifabutin or a rifabutin derivative, or rifampicin or a rifampicin derivative, or a pharmaceutically acceptable salt, hydrate, or prodrug thereof, or a combination thereof, increases sensitivity in a parasite. In certain embodiments, the drug or drugs can include an antiparasitic drug. Example types of suitable antiparasitic drugs and drug combinations include antinematodic drugs, anticestodic drugs, antitrematodic drugs, antiamamoebic drugs, antiprotazoal drugs, antihelminthic drugs, tiniacides, antiprotozoic drugs, and other drugs. Example classes of suitable antiparasitic drugs include benzimidazoles, avermectins, milbemycins, piperazines, octadepsipeptides, thiophenes, pamoates, spiroindoles, imadazothiazoles, quinines, biguanides, sulfonamides, tetracyclines, lincomycins, alkaloids, carbamates, formamidines, organophosphates, Rifampin, Amphotericin B, Melarsoprol, Eflornithine, Miltefosine, Metronidazole, Tinadadazole, Quinine-pyrithamine-sulfadiazine, Trimethoprin-sulfa methoxazole, Piperazine, Praziquantel, Triclabendazole, Octadepsipeptides, Amino Acetonitrile derivatives and derivatives thereof.

Exemplary suitable antiparasitic drugs for use with the compositions and methods of the present disclosure include, without limitation, ivermectin, selamectin, doramectin, abamectin, albendazole, mebendazole, thiabendazole, fenbendazole, triclabendazole, flubendazole, diethylcarbazamine, niclosamide, suramin, pyrantel, pamoate, levamisole, praziquantel, emodepside, monepantel, derquantel, rifoxanide, artemether, quinine, quinidine, chloroquine, amodiaquine, pyrimethamine, proguanil, sulfadozine, mefloquine, atovaquone, primaquine, artemisinin, doxycycline, clindamycin, sulfadoxine-pyrimethamine, moxidectin, permethrin, hexylresorcinol, and combinations thereof.

Accordingly, in certain embodiments, the antiparasitic drug or drugs to which sensitivity is increased in a parasite by the rifamycin or rifamycin derivative, or pharmaceutically acceptable salt, hydrate, or prodrug thereof, or a combination thereof, can include, without limitation, one or more of the antiparasitic drugs listed in Table 2 below, or any class or type referred to therein, or any antiparasitic drug referred to herein.

TABLE 2

Antiparasitic Drugs

| Antiparasitic Drug | Class/Type | Mechanism/Target |
|---|---|---|
| Trimethoprim | Anti-folate | Dihydrofolate reductase ("DHFR") |
| Pyrimethamine (Daraprim) | | |
| Proguanil (Paludrine) | | |
| Sulfamethoxazole | | deoxyhypusine synthase ("DHPS") |
| Sulfadiazine | | |
| Sulfadoxine | | |
| Atovaquone (Mepron) | Ubiquinone Analog | Perturbs Mitochondrial Electron Transport |
| Spiramycin (Rovmycin) - | Antibiotic | Ketolide Protein Synthesis Inhibitor |
| Azithromycin (Zithromax) - | | Macrolide Protein Synthesis Inhibitor |
| Paromomycin (Humatin) - | | Aminoglycoside Protein Synthesis Inhibitor |
| Clindamycin (Cleocin) - | | Lincosamide Protein Synthesis Inhibitor |
| Tetracycline (Sumycin) - | | Polyketide Protein Synthesis Inhibitor |
| Doxycycline (Vibramycin) - | | Polyketide Protein Synthesis Inhibitor |
| Metronidazole (Flagyl) | Nitroimidazole | PFOR-Dependent RNS Generation |
| Tinidazole (Tindamax) | | |
| Nitazoxanide (Alinia) | Nitrothiazole | |
| Iodoquinol (Yodoxin) | Quinoline | Iron chelation |
| Chloroquine | | Hemozoin Inhibitor |
| Primaquine | | |
| Mefloquine | | |
| Quinine | | |
| Quinidine | | |
| Praziquantel (Biltride)[1,2] | | Paralytic |
| Oxaminquine (Vansil)[1] | | |
| Triclabendazole (Egaten)[1] | Benzimidazole | Prevents tubulin polymerization |
| Niridazole[1] | Thiazole | Paralytic Phosphofructokinase Inhibitor |
| Stibophen[1] | Arylsulfonate | |
| Trichlorfon[1] | Organophosphate | Paralytic ACE Inhibitor |
| Mebendazole (Vermox)[2,3] | Benzimidazole | Prevents tublin polymerization |
| Albendazole (Albenza)[2,3] | | |
| Niclosamide[2] | Salicylanilide | Decouples Oxidative Phosphorylation |
| Ivermectin (Stromectol, Mectizan)[3,4] | Macroyclic Lactone | Paralytic GABA Agonist |
| Doxycycline (Vibramycin)[3] | Antibiotic | Targets Symbiotic Bacteria in Parasite Gut |
| Diethylcarbamazine (DEC)[3] | Piperazine | Perturbs Arachidonic Acid Metabolism |
| Pyrantel Pamoate (Helmex)[3] | Tetrahydropyrimidine | Paralytic |
| Permethrin (Elimite, Nix)[4] | Pyrethroid | Neurotoxin via Na-Channel Binding |
| Tiabendazole[3,5] | Nitrothiazole | Fumarate reductase |

TABLE 2-continued

Antiparasitic Drugs

| Antiparasitic Drug | Class/Type | Mechanism/Target |
|---|---|---|
| Levamisole[3,5] | Imidazothiazole | Paralytic Ach agonist |
| Mibemycin[3] | Macrolide | Glutamate sensitive chloride channels |

[1]Anti-trematodal;
[2]Anti-cestodal;
[3]Anti-nematodal:
[4]Anti-ectoparasitic;
[5]Anti-helminthic In methods of the current disclosure, the parasite can be sensitized to a drug or drugs already known to inhibit the parasite, or it can be sensitized to a drug or drugs not previously used with that type of parasite. If the parasite is a drug-resistant parasite that has acquired or evolved a resistance to a drug, it can be sensitized to a drug that previously exhibited a decreased ability to inhibit the parasite. In certain embodiments, sensitization of the parasite to the drug occurs at least in part by P-gp inhibition.

In certain embodiments, the composition can directly inhibit the parasite instead of or in addition to causing drug-sensitization.

The parasite that undergoes drug-sensitization or inhibition can be any type of parasite. It may, for instance, be a helminth, such as a nematode, a trematode, or a cestode, a protozoa, or an arthropod (i.e., an ectoparasite). The parasite can be a parasite of any animal or plant. By way of example and not limitation, the parasite that undergoes drug-sensitization or inhibition can be a species of the genus *Plasmodium*, such as *Plasmodium falciparum, Plasmodium malariae, Plasmodium ovale*, and *Plasmodium vivax*, a species of the genus *Ascaris*, such as *Ascaris lumbricoides*, a species of the genus *Enterobius*, such as *Enterobius vermicularis*, a species of the genus *Trichinella*, such as *Trichinella spiralis*, a species of the genus *Haemonchus*, such as *Haemonchus contorlus*, a species of the genera *Aphelenchoides, Ditylenchus, Globodera, Heterodera, Longidorus, Meloidogyne, Nacobbus, Pratylenchus, Trichodorus*, and *Xiphinema*, a species of the genus *Bursaphelenchus*, such as *Bursaphelenchus xylophilus*, a species of the genus *Fasciola*, such as *Fasciola hepatica*, a species of the genus *Coccidoides*, or a species of the genus *Onchocerca*, such as *Onchocerca vohulus*.

The parasite that undergoes drug-sensitization or inhibition can be any parasite. The parasite can be, for example, any parasite commonly referred to or known as a flea, a tick, a worm, a hookworm, a roundworm, a heartworm, a fluke, a mite, a spider, a beetle, a mosquito, a fly, or a bed bug.

Accordingly, in certain embodiments the parasite that undergoes drug-sensitization or inhibition can be a protozoan parasite, such as, for example, the protozoan parasites of Table 3 below. In certain embodiments, the parasite that undergoes drug sensitization or inhibition can be a helminthic parasite (parasitic worm) such as, for example the helminthic parasites of Table 4 below. In certain embodiments, the parasite that undergoes drug sensitization or inhibition can be an ectoparasite, such as, for example, the helminthic parasites of Table 5 below. In certain embodiments, multiple parasites of different species, genera, class, or other category can simultaneously undergo drug sensitization or inhibition in a single host harboring the multiple parasites.

TABLE 3

Representative Protozoan Parasites

| Parasite | Disease | Symptoms (humans) | Current Drug Regimen |
|---|---|---|---|
| *Cryptosporidium hominis, parvum* | Cryptosporidiasis | Diarrhea-causing parasites (typically asymptomatic) but deadly in susceptible pop. (AIDS, Children, etc.) | Uncomplicated: Nitazoxanide (Alinia) AIDS: Paromomycin (Humatin) w/ Azithromycin (Zithromax) Questionable Efficacy for both regimes. |
| *Isosporiasis belli* | Isosporiasis | Diarrhea-causing parasites (typically asymptomatic) but deadly in susceptible pop. (AID'S, Children, etc.) | #1: Trimethoprim-Sulfamethoxazole w/ folinic acid (Leucovorin) #2: Pyrimethamine (Daraprim) w/ folinic acid (Leucovorin) |
| *Cyclospora cayetanesis* | Cycosporiasis | Diarrhea-causing parasites (typically asymptomatic) but deadly in susceptible pop. (AIDS, Children, etc.) | Uncomplicated: No Recognized Effective Treatment AIDS: Trimethoprim-Sulfamethoxazole w/folinic acid (Leucovorin) considered effective at reducing severity. Control HIV infection to resolve parasite infestation. |

TABLE 3-continued

Representative Protozoan Parasites

| Parasite | Disease | Symptoms (humans) | Current Drug Regimen |
| --- | --- | --- | --- |
| *Toxoplasma gondii* | Toxoplasmosis | Usually asymptomatic but causes fatal encephalitis in AIDS/Immunocompromised Patients. TORCH Pathogen associated with transplacental infection. | Uncomplicated: Pyrimethamine (Daraprim) + sulfadiazine/clindamycin (Cleocin)/ azithromycin (Zithromax) Pregnancy: Uncomplicated + Spiramycin (Rovamycin) AIDS: Pyrimethamine (Daraprim) + sulfadiazine/clindamycin (Cleocin)/ azithromycin (Zithromax). Treat patient indefinitely once Dx. *** All regimes require folinic acid (Leucovorin) *** |
| *Balantidium coli* | Balantidiasis | Diarrhea, Constiption. Can mimick inflammatory bowel conditions. | #1: Tetracycline (Sumycin) #2: Metronidazole (Flagyl) #3: Iodoquinol (Yodoxin) |
| *Entamoeba histolytica, dispar* | Amebiasis | Typically asymptomatic but can cause wide range of symptoms ranging from mild diarrhea to severe dysentery with mucoid, bloody diarrhea. May cause ameobic liver abscesses w/ or w/o intestinal disease. | Asymptomatic: Luminal Agents Iodoquinol (Yodoxin) or paromomycin (Humatin) Symptomatic: Colitis & Hepatic Abscess Metronidazole (Flagyl) + Luminal Agents. |
| *Giardia lamblia* | Giardiasis | 2/3 Asymptomatic. Others experience diarrhea varying in severity, sulfurous gas/belches, weight loss, cramping, pain, etc. Traveler's Diarrhea. | Metronidazole (Flagyl) |
| *Trichmonas vaginalis* | Trichomoniasis | Very common STI that is usually asymtomatic but can cause vaginits, urethritis, etc. | #1 Metronidazole (Flagyl) #2 Tinidazole (Tindamax) |
| *Dientamoeba fragilis* | Dientamoebiasis | Traveler's diarrhea, chronic diarrhea/abdominal pain, failure to thrive. | Prophylaxis: Paromomycin (Humatin) Symptomatic: Iodouinol (Yodoxin), Paromomycin (Humatin), Tetracycline (Sumycin), Metronidazole (Flagyl) combination of any two. |
| *Blastocystis hominis* | Blastocystosis | Typically nonsymptomatic and colonization transient. Nonspecific GI symptoms including diarrhea, flatulence, pain, etc. | Metronidazole (Flagyl) now considered ineffective. Nitazoxanide (Alinia) possible replacement (trials ongoing) |
| *Plasmodium falciparum, vivax, ovale, malariea* | Malaria | Classical paroxysm (cyclic fevers) w/headache, joint pain, vomiting, hemolytic anemia, jaundice, and convulsions. Neurologica signs in severe cases. Presents 1-3 weeks post infection w/o prophylaxis. | Hemozoin Inhibitors: Chloroquine (I), Primaquine (II), Mefloquine (I), Quinine (I), Quinidine Gluconate (I). Antifolates: sulfadoxine (I), sulfamethoxypyrazine (I) + proguanil (II) or pyrimethamine (I). Sesquiterpene Lactones: Artemether, Artesunate, Dihyroartemisin, Artemotil, Artemisin (II) None FDA Approved. Naphthoquinonones: Atovaquone (II) Adjuncts: Tetracycline/Doxycycline, Clindamycin (Lincosamides). Proven Schizoticides. Use when indicated for Severe Disease. |
| *Babesia divergens, microfti*, other | Babesiosis | Typically asymptomatic (>50%) with others developing malaria-like illness w/hemolytic anemia, cyclic fevers, thrombocytopenia, and possible organ failure 1-4 weeks post infection. | Mild/Moderate: Atovaquone (Mepron) w/Azithromycin (Zithromax) Severe: Quinine Sulfate w/ Clindamycin (Cleocin) |
| *Trypanosoma brucei* | African Trypanosomiasis (Sleeping Sickness) | Hemolymphatic phase with fever, headache, pains, and fever followed by CNS involvement. Fatal if not treated promptly. | No CNS *T.b. rhodesiense*: Suramin No CNS *T.b. gambiense*: Pentamidine CNS *T.b. rhodesiense*: Melarsoprol (Mel B, Arsobal) CNS *T.b. gambiense*: Eflornithine (DFMO, Ordinyl) |

TABLE 3-continued

Representative Protozoan Parasites

| Parasite | Disease | Symptoms (humans) | Current Drug Regimen |
| --- | --- | --- | --- |
| *Trypanosoma cruzi* | American Trypanosomiasis (Chaga's Disease) | Acute disease usually asymptomatic but cagoma/Romana's Sign may be present. Chronic infection destroys myenteric complex causing megaesophaug, colon, other dilations and dilated cardiomyopathy. | #1: Nifurtimox (Lampit) #2: Benzidazole (Rohagan) Both drugs can effect radical cure in acute phase but become less effective in chronic patients (especially those who have been infected for longer periods of time) |
| *Leishomania, mexicana aethiopica, tropic, braziliensis, donovani, infantum.* | Leishmaniasis | Cutaneous, mucocutaneous, difffuse cutaneous, and viseral (Kala Azar) Presentations | Classical Tx: Sodium Stibogluconate + pentavalent antimony (Pentostam) w/meglumine antimonate (Glucontime). Retired due to tox & resistance. Cutaneous Local: Topical paromomycin + gentamicin formulation. Oral Systemic: Miltefosine (Impavido) w/azoles ketoconazole, itraconazole, fluconazole IV Systemic: Amphotericin B (Ambisome) |

TABLE 4

Representative Helminthic Parasites

| Parasite | Disease | Symptoms (humans) | Current Drug Regimen |
| --- | --- | --- | --- |
| *Schistosoma mansoni, japonicum, haemotobium* | Schistosomiasis | Direct skin penetration in aquatic soils, etc. with infected fresh-water snails resulting in prolonged colonizationof the intestines/urinary tact dependent on species. Causes malnutiriton, organ damage, and associated with bladder cancer. | Praziquantel (Biltride) |
| *Trichobilharzia regenti* | Swimmer's Itch | Direct skin penetration in aquatic soils, etc. with infected fresh-water snails. Mild w/localized skin irritation. | Antihistamines No specific treatment |
| *Clonorchis simensis* | Clonorchiasis | Following ingestion of raw fish, colonize biliary tract. Associated with cholangiocarcinoma, liver damage, etc. | #1: Praziquantel (Biltride) #2: Albendazole |
| *Fasciola hepatica, gigantica* | Fascioliasis | Liver dysfunction, pain following colonization of the liver and biliary tract | Triclabendazole (Egaten) |
| *Opisthorchis viverrinil* | Opisthorchiasis | Following ingestion of raw fish, colonize biliary tract. Associated with cholangiocarcinoma, liver damage, etc. | #1: Praziquantel (Biltride) #2: Albendazole |
| *Paragonimus westermani, kellicotti* | Paragonimiasis | Liver, Lung dysfunction w/ pulmonary manifestations in chronic infections. | #1: Praziquantel (Biltride) #2: Triclabendazole (Egaten) |
| *Fasciolopsis buski* | Fasciolopisiasis | Typically asymptomatic but can include diarrhea, abdominal pain, obstruction. | Praziquantel (Biltride) |
| *Metagonimus yokagawai* | Metagonimiasis | Diarrhea, colic, obstruction. | Praziquantel (Biltride) |
| *Heterophyes heterophyes* | Heterophyiasis | Diarrhea, colic, obstruction. | Praziquantel (Biltride) |
| *Echinococcus granulosus, multilocularis* | Echinocccosis | Typically asymptomatic with formation of large cysts containing parasites. Rupture results in allergic reaction/anaphylaxis. Can behave like slow-growing destructive tumors. | Cystic: Albendazole (Albenza) w/ Surgical resection of cysts. Add Praziquantel (Biltride) if cyst spillage occurs during surgery. Alveolar: Albendazole (Albenza) or Mebendazole (Vermox) |

TABLE 4-continued

Representative Helminthic Parasites

| Parasite | Disease | Symptoms (humans) | Current Drug Regimen |
| --- | --- | --- | --- |
| *Taenia saginata, solium, asiatica* | Taeniasis | Tapeworms acquired from eating undercooked beef and pork. Adult worms reside in intestines and reach large sizes causing malnutrition, obstruction, etc. | Praziquantel (Biltride) |
| *Taenia solium, asiatica* | Cysticerosis | Occur following infection with pork tapeworms. All tissues susceptible to cyst infestation, CNS/CVS most dangerous. | Praziquantel (Biltride) w/ prednisone |
| *Hymenolpeis nana, diminuta* | Hymenolepiasis | Asymptomatic dwarf tapeworm. Extremely common. | #1: Praziquantel<br>#2: Niclosamide<br>#3: Nitazoxanide |
| *Diphyllobotrium latum, mansonoides* | Diphyllobothriasis | Freshwater fish tapeworm. Largest of all tapeworms and can cause obstruction, B12 def. w/megaloblastic anemia. | Praziquantel |
| *Spirometra erinaceieuropaei* | Sparganosis | Asymptomatic unless woms migrate to CNS. Typically nonspecific skin irritation as worms migrate. | No drug treatment. Surgical removal of worms required. |
| *Dracunculus medinensis* | Dracunculiasis | Guinea Worms. Enough said. | No drug treatment. "Stick Therapy" to remove erupting worms from lower extremities. |
| *Onchocerca volvulus* | Onchocerciasis | River Blindess | Ivermectin (Stromectol) & Doxycycline (Vibramycin) |
| *Loa loa* | Loiasis | Asymptomatic Eye Worm | Diethylcarbamazine |
| *Mansonella perstans, ozzardi, streptocera* | Mansonellosis | Swelling, nonspecific skin symptoms, rashes, typically asymptomatic. | #1: Mebendazole (Vermox) or Albendazole (Albenza)<br>#2: Ivermectin (Stromectol)<br>*** Include doxycycline (Vibramycin) w/#1 or #2 *** |
| *Wucheria bancrofti, Brugia malayi, timori* | Lymphatic Filariasis | Typically asymtomatic but some develop profound lymphatic obstruction and lymphadema (Elephantiasis) w/episodes of febrile/afebrile lymphangitis and lymphadenitis. Nocturnal cough associated with migrating worms. | Ivermectin (Stromectol) w/ Deithylcarbamazine (DEC) Typically responds poorly to drugs once lymphedema sets in. |
| *Gnathostoma spinigerum, hispidium* | Gnathostomiasis | Painful, intermittent, itchy swellings caused by migrating worms. Possible VLM organism. | #1: Ivermectin (Stromectol)<br>#2: Albendazole (Albenza) |
| *Ancylostoma duodenale, brazilienes* | Ancylostomiasis and Cutaneous Larva Migrans | Signs of iron-deficiency anemia, malnutrition, and skin manifestations following infection by penetration of intact skin from infected soil. (Hookworms) | #1: Albendazole (Albenza)<br>#2: Mebendazole (Vermox)<br>#3: Pyrantel Pamoate (Helmex) |
| *Necator americanus* | Necatoriasis | Signs of iron-deficiency anemia, malnutrition, and skin manifestations following infection by penetration of intact skin from infected soil. (Hookworms) | #1: Albendazole (Albenza)<br>#2: Mebendazole (Vermox)<br>#3: Pyrantel Pamoate (Helmex) |
| *Angiostrongylus cantonensis* | Angiostrongyliasis | Abdominal disease and eosinophilic meningitis presentations possible. | #1: Albendazole (Albenza)<br>#2: Mebendazole (Vermox)<br>*** w/prednisolone *** |
| *Ascaris lumbricoides* | Ascariasis | Typically asymptomatic w/ nonspecific respiratory symptoms during pulmonary stage followed by adominal pain and possible obstrcution of biliary tract and/or intestines. | #1: Abendazole (Albenza)<br>#2: Mebendazole (Vermox)<br>#3: Ivermectin (Stromectol) |
| *Toxocara canis, cati* | Toxocariasis and Visceral Larva Migrans | Typically asymptomatic. VLM very serious depending on what organ is invaded. Non-VLM show generalized signs of worm infestations. | #1: Ivermectin (Stromectol)<br>#2: Albendazole (Albenza) |

TABLE 4-continued

Representative Helminthic Parasites

| Parasite | Disease | Symptoms (humans) | Current Drug Regimen |
|---|---|---|---|
| *Strongyloides stercoralis* | Strongyloidiasis | Typically asymptomatic w/ mild GI symptoms including pain and diarrhea. May present with rashes. | #1: Mebendazole (Vermox) #2: Albendazole (Albenza) |
| *Enterobius vermicularis* | Enterobiasis | Typically asymptomatic w/ pruitic perianal region and possible superinfections. | #1: Albendazole (Albenza) #2: Mebendazole (Vermox) #3: Pyrantel Pamoate (Helmex) |
| *Trichinella spiralis* | Trichinellosis | Acquired from undercooked pork resulting in tissue infestation following actue GI symptoms. Larval encystments cause organ-specific symptoms. | #1: Mebendazole (Vermox) #2: Albendazole (Albenza) |
| *Trichuris trichiura* | Trichuriasis | Typically asymptomatic but heavy infections may cause GI symptoms. | #1: Mebendazole (Vermox) or #2: Albendazole (Albenza) #3: Ivermectin (Stromectol) |

TABLE 5

Representative Ectoparasites

| Parasite | Disease | Symptoms (humans) | Current Drug Regimen |
|---|---|---|---|
| *Pediculus humanus capitus, humanus* | Pediculosis | Head lice, body lice spread by direct contact with either infected persons or infested bedding, clothing, hats, etc. | Permethrin (Elimite, Nix, Acticin, etc.) OTC any 1% formulation topical only. |
| *Phthiriasis pubis* | Phthiriasis | Pubic lice or "Crabs" spread by direct contact (sexual). | Permethrin (Elimite, Nix, Acticin, etc.) OTC any 1% formulation topical only. |
| *Sarcoptes scabiei* | Scabies | Mite infests stratum corneum with resulting immune reaction forming itchy blisters/lesions. | #1: Rx Permethrin (Elimite, Lyclear, Nix) Any 5% formulation. #2: Crotamiton (Eurax, Crotan) #3: Lindane 1% #4 Ivermectin (Stromectol) for Norwegian variant. |

The composition can be delivered to the parasite in a host organism by delivering the composition to the host organism, such as by administering, feeding, injecting, topical application, attachment, or providing for inhalation. In certain embodiments, the composition contacts the parasite by diffusion throughout the host organism after administration. Additionally or alternatively, the composition can be delivered to a recipient prophylactically, i.e., prior to recipient infection, or contact with, or exposure to, the parasite. The mode of delivery can be selected based on a number of factors, including metabolism of the rifamycin or a rifamycin derivative, such as rifabutin or a rifabutin derivative, or rifampicin or a rifampicin derivative, or a pharmaceutically acceptable salt, hydrate, or prodrug thereof, or a combination thereof, or another drug in the composition, the mode of administration of other drugs to the host organism, such as the drug to which the parasite is sensitized, the location and type of parasite to be drug-sensitized, the health of the host organism, the ability or inability to use particular dosing forms or schedules with the host organism, preferred dosing schedule, including any adjustment to dosing schedules due to side effects of other drugs, and ease of administration. In certain embodiments, the mode of administration can be enteral, such as orally or by introduction into a feeding tube. In certain embodiments, the mode of administration can be parenteral, such as intravenously. In certain embodiments, the mode of administration is transcutaneous. In certain embodiments, the mode of administration is topical. In certain embodiments the mode of administration is by affixing a dosage form to the to body of an infected or susceptible animal, such as a collar or tag.

The dosage amounts of the and administration schedule of the rifamycin or rifamycin derivative, such as rifabutin or rifabutin derivative, or rifampicin or rifampicin derivative, or pharmaceutically acceptable salt, hydrate, or prodrug thereof, or combination thereof, can vary depending on other components of the composition and their effects on drug availability in a recipient, the type of drug or drugs to which the parasite is sensitized, the intended mode of administration, the intended schedule for administration, when other drugs are administered, any drug toxicity concerns, and the recipient's response to the drug. In certain embodiments, the amount and frequency of delivery of rifamycin or rifamycin derivative, such as rifabutin or rifabutin derivative, or rifampicin or rifampicin derivative, or pharmaceutically acceptable salt, hydrate, or prodrug thereof, or combination thereof, can be such that levels in the recipient remain well below levels at which toxicity to the recipient becomes a concern. However the amount and frequency can also be such that the levels of rifamycin or rifamycin derivative, such as rifabutin or rifabutin derivative, or rifampicin or rifampicin derivative, or pharmaceutically acceptable salt, hydrate, or prodrug thereof, or combination thereof, in the recipient remain continuously at a level sufficient to induce drug-sensitization or are at a level sufficient to induce drug sensitization when or shortly after the drug to which the parasite is sensitized is delivered to it. Accordingly, the composition can be taken on a regular basis during treatment with the drug to which the parasite is sensitized or it can be taken only a set time before, at the same time, or a set time after the drug to which the parasite is sensitized.

Without limiting the compositions and methods of administration described herein, in certain embodiments, the rifamycin or rifamycin derivative, such as rifabutin or rifabutin derivative, or rifampicin or rifampicin derivative, or pharmaceutically acceptable salt, hydrate, or prodrug thereof, or combination thereof, can exhibit its drug-sensitization effect on a parasite by directly or indirectly inhibiting one or more drug efflux pumps. In certain embodiments, the one or more drug efflux pumps includes P-gp (also referred to as ATP-binding cassette sub-family B member 1 (ABCB1) pump). This glycoprotein is found in cellular membranes, such as the cell membrane and/or vacuolar membranes, and actively transports certain drugs, such as xenobiotic drugs, out of parasites, reducing efficacy of the drug. In certain embodiments, the one or more drug efflux pumps includes a P-gp homolog. In certain embodiments, the one or more drug efflux pumps include a drug or multidrug resistance pump. By inhibiting these pumps, the amount of drug present in a parasite can be increased and thus the killing or inhibiting effect on the parasite can be increased.

EXAMPLES

The following examples are provided to further illustrate certain embodiments of the disclosure. They are not intended to disclose or describe each and every aspect of the disclosure in complete detail and should be not be so interpreted. Unless otherwise specified, designations of cells lines and compositions are used consistently throughout these examples.

Example 1

Rifamycin Derivative Synthesis

The 3,4-cyclo-rifamycin (rifabutin) derivatives of the current disclosure made be prepared as shown in the schemes listed below.

Scheme 1 illustrates the general preparation of 11-deoxo-11-imino-3,4-spiro-piperidyl-rifamycins (1c) and 11-deoxo-11-amino-3,4-spiro-piperidyl-rifamycins (1d). The compounds of (1c) are synthesized by condensation of 3-amino-4-deoxy-4-imino-rifamycin S (1a) with a substituted piperidone or hexanon-type of ketone (1 b) at a temperature range from 10° C. to 70° C. in organic solvent, such as THF or ethanol, in the presence of an excess of ammonium salt, such as ammonium acetate, in a sealed reaction tube. Reduction of 11-imino-rifamycin (1c) with reducing reagent, such as NaBH$_4$, in organic solvent, such as THF and EtOH at a temperature range from 0° C. to room temperature produces 11-amino-rifamycin (1d). When the compound is RTI-35, the thioether could be oxidized to sulfoxide (—SO—) or sulfone (—SO2-) depending upon the ratio of compound 1c and oxidizing agents. When the compound is RTI-44, product is obtained by de-protection of Boc-propected-piperidine or Fmoc-protected-piperidine.

Scheme 1

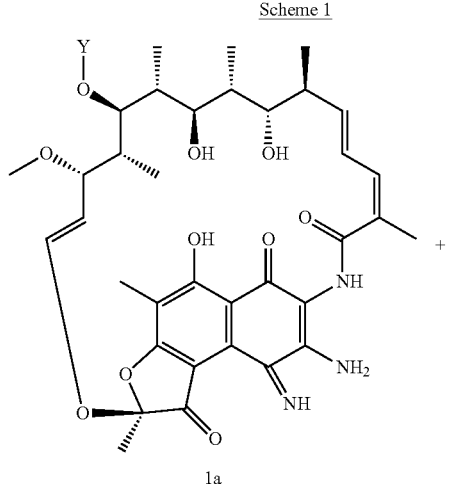

1a

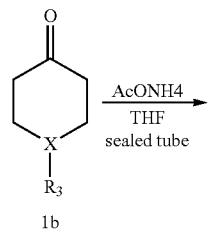

1b

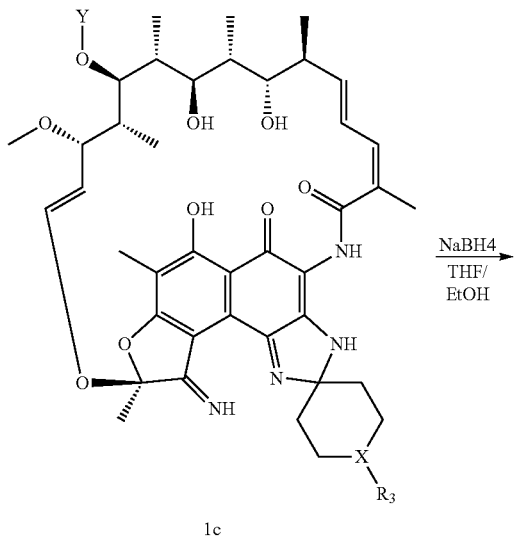

1c

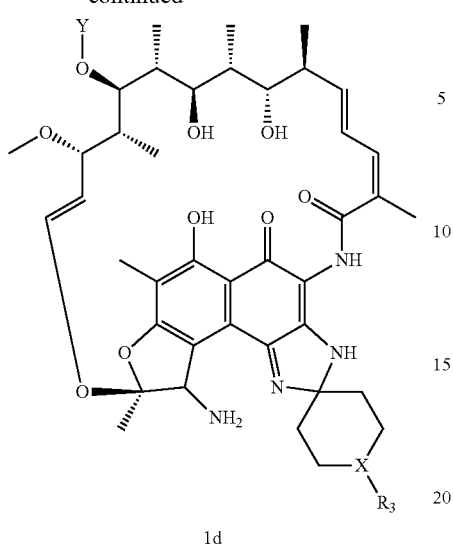

1d

Scheme 2 illustrates the general preparation of 3,4-spiro-piperidyl-rifamycins (2c) and 11-deoxo-11-hydroxy-3,4-spiro-piperidyl-rifamycins (2d). The compounds of (2c) are synthesized by condensation of 3-amino-4-deoxo-4-imino-rifamycin S (1a) with a substituted piperidone or hexanon-type of ketone (1b) at a temperature range from 10° C. to 70° C. in organic solvent, such as THF or ethanol, in the presence or absence of a catalyst, such as Zinc. Reduction of 11-oxo of rifamycin (2c) with reducing reagent such as NaBH$_4$, in organic solvent, such as THF and EtOH at a temperature range from 0° C. to room temperature produce 11-hydroxy-rifamycin (2d).

Scheme 2.

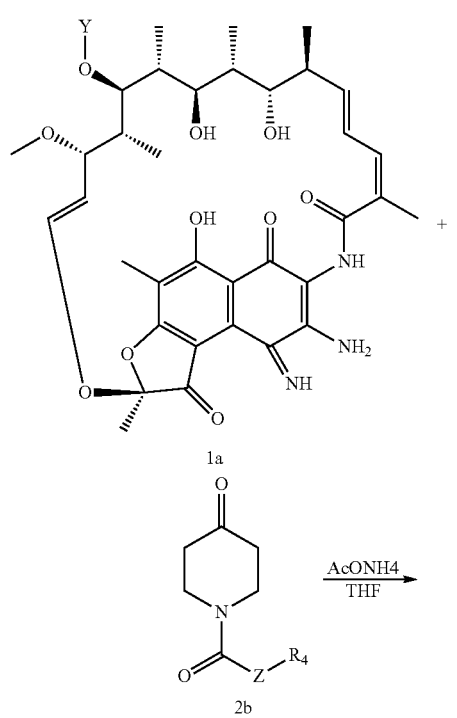

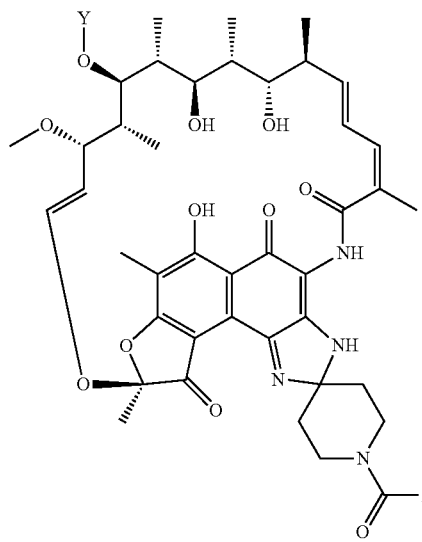

2c

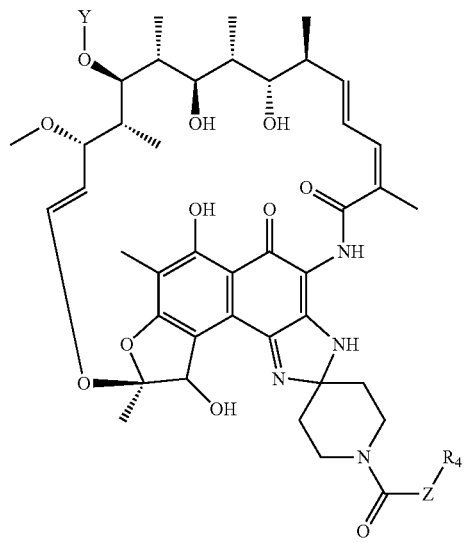

2d

The intermediate of (1a) is commercially available or can be obtained from the rifamycin S. The hexanon-type of ketone or 4-substituted piperidone (1b or 2b: Z=C, or O) is either commercially available or can be prepared by known procedures. The 4-oxo-piperidine-1-carboxamide (2b: X=NH) is prepared by reacting 4-oxo-piperidine-1-carbonyl chloride.

Scheme 3 illustrates the general preparation of 11-deoxo-11-hydroxyimino-3,4-spiro-piperidyl-rifamycins (3c). The compounds of (3c) are synthesized from the reaction of 11-oxy-rifamycin compound (2c) with hydroxylamine (or its HCl salt) at a temperature range from 10° C. to 70° C. in organic solvent, such as THF or methanol, in the presence or absence of base, such as pyridine.

Scheme 3.

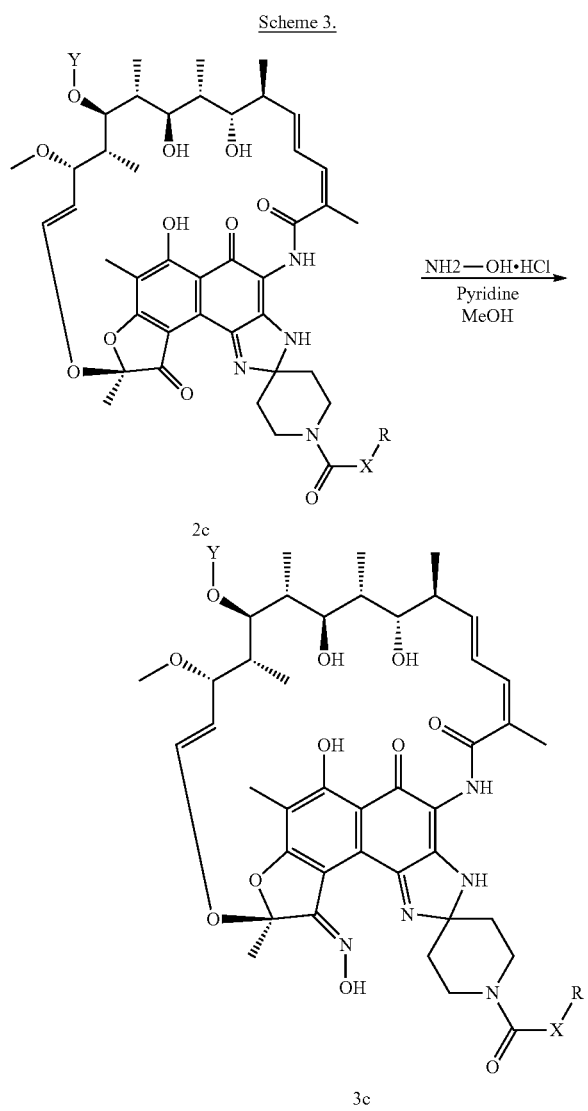

The above syntheses schemes are preferred schemes for the preparation of the indicated types of compounds. It is apparent to one skilled in art that other sequences of the reactions, and alternative reagents can be used for the synthesis of the rifamycin derivatives of the present disclosure. These alternatives for the synthesis of the derivatives are within the scope of this invention.

The following examples provide synthesis schemes for specific rifabutin derivative compositions. All starting material used in these examples are either purchased from commercial sources or prepared according to published procedures. Reagents were purchased from commercial sources and used without further purification. Reactions with moisture-sensitive reagents were performed under a nitrogen atmosphere. Concentration of solutions was performed by reduced pressure (in vacuum) rotary evaporation. Column flash chromatography was performed using silica gel 60 as stationary phase. The preparative thin-layer chromatography (TLC) was performed using glass plates (20×20 cm) of silica gel (60 F254, thickness 1 mm or 2 mm).

Proton nuclear magnetic resonance (1H-NMR) spectra were recorded on a Varian Inova 300, or 500 MHz, magnetic resonance spectrometer. 1H-NMR refers to proton nuclear magnetic resonance spectroscopy with chemical shifts reported in ppm (parts per million) downfield from tetramethylsilane or referred to a residue signal of solvent ($CHCl_3$=7.27). 13C-NMR spectra were recorded on Varian Inova 500 MHz, spectrometer operating at 125 MHz, and Chemical shifts were reported in ppm and referenced to residual solvent signals ($CHCl_3$=d 77.23 for carbon)

The high resolution mass spectra (HRMS) were carried out in a Bruker-micrOTOF-QII spectrometer, using electro spray ionization positive (ESI+) method and reported as M+H or M+Na, referring to protonated molecular ion or its sodium complex.

The following examples are for illustration purposes and are not intended to limit the scope of the invention. It will be apparent to one skilled in the art that the compounds of current invention can be prepared by a variety of synthetic routes, including but not limited to substitution of appropriate reagents, solvents or catalyst, change of reaction sequence, and variation of protecting groups.

General Procedure (A) for Synthesis of Compounds (1c in Scheme 1)

In a sealed reaction tube a reaction mixture of 3-amino-4-imino-rifamycin S (1a) (0.1 mmol), piperidone or hexanon-type of ketone (1b) (0.2-0.3 mmol) and ammonium acetate (1 mmol) in THF (3 ml) was stirred at 60° C. overnight under nitrogen. The reaction mixture was allowed to cool to room temperature and diluted with DCM (20 ml) and water (20 ml). The aqueous phase was extracted with DCM (2×20 ml). The combined organic phase was washed with water (20 ml) and brine. The organic phase was dried over anhydrous sodium sulphate, filtered and concentrated under vacuum. The residue was purified either by silica gel column chromatography or by silica gel preparative thin-layer chromatography with methanol in DCM as eluent to give the product as purple solid.

General Procedure (B) for Synthesis of Compounds (2c in Scheme 1)

In a round bottom flask with condenser, a reaction mixture of 3-amino-4-imino-rifamycin S (1a) (0.1 mmol), piperidone or hexanon-type of ketone (1b) (0.2-0.3 mmol), and ammonium acetate (0.2-0.3 mmol) in THF (8 ml) was stirred at 75° C. overnight under nitrogen. The reaction mixture was allowed to cool to room temperature and diluted with DCM (20 ml) and water (20 ml). The aqueous phase was extracted with DCM (2×20 ml). The combined organic phase was washed with water (20 ml) and brine. The organic phase was dried over anhydrous sodium sulphate, filtered and concentrated under vacuum. The residue was purified either by silica gel column chromatography or by silica gel preparative thin-layer chromatography with methanol in DCM as eluent to give the product as purple solid.

General Procedure (C) for Synthesis of Compounds (1d in Scheme 1 and 2d in Scheme 2)

To a solution of rifamycin 11-imine or 11-oxo-compound (1c or 2c) (0.1 mmol) in THF (4 ml) was added a suspension of NaBH4 (0.2 mmol) in ethanol (4 ml) at room temperature. The reaction mixture stirred at room temperature for 1.5 hours and diluted with ethyl acetate (20 ml) and water (20 ml). The aqueous phase was extracted with ethyl acetate (2×20 ml). The combined organic phase was washed with water and brine. The organic phase was dried over anhydrous sodium sulphate, filtered and concentrated under vacuum. The residue was purified either by silica gel column chromatography or by silica gel preparative thin-layer chromatography with methanol in DCM as eluent to give the product as purple solid.

Preparation of RTI-33 11-deoxy-11-imino-4-deoxy-3,4[2-spiro-[1-(t-butyloxycarbonyl)-piperidin-4-yl]]-(1H)-imidazo-(2,5-dihydro)rifamycin S Following the general procedure (A), the title compound was obtained as a pure solid. HRMS (ESI$^+$): 890.4570 (M+H)$^+$; calculated for (M+H)$^+$: 890.4553; 1H-NMR (300 MHz, CDCl$_3$) δ −0.09 (d, J=7 Hz, 3H), 0.61 (d, J=7 Hz, 3H), 0.84 (d, J=7 Hz, 3H), 1.04 (d, J=7 Hz, 3H), 1.44 (m, 1H), 1.50 (s, 9H), 1.6-1.85 (m, 4H), 1.88 (s, 3H), 1.9-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.49 (s, 1H), 3.60 (d, J=5 Hz, 1H), 3.68 (d, J=10 Hz, 1H), 3.6-3.8 (br, 2H), 3.95-4.1 (br, 2H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (dd, J=16 and 10 Hz, 1H), 8.26 (s, 1H), 8.71 (bs, 1H), 12.93 (s, 1H), 14.21 (s, 1H).

Preparation of RTI-35 11-deoxy-11-imino-4-deoxy-34[2-spiro-tetrahydrothiopyran-4-yl]-(1H)-imidazo-(25-dihydro)rifamycin S Following the general procedure (A), the title compound was obtained as a pure solid. HRMS (ESI$^+$): 807.3665 (M+H)$^+$; calculated for (M+H)$^+$: 807.3640; RTI-035A, 1H-NMR (300 MHz, CDCl3); −0.08 (d, J=7 Hz, 3H), 0.62 (d, J=7 Hz, 3H), 0.85 (d, J=7 Hz, 3H), 1.05 (d, J=7 Hz, 3H), 1.44 (m, 1H), 1.75-1.85 (m, 2H), 1.89 (s, 3H), 2.02 (s, 3H), 2.07 (s, 3H) 1.9-2.15 (m, 4H), 2.35 (s, 3H), 2.40 (m, 1H), 2.75-2.9 (m, 2H), 3.00 (m, 1H), 3.09 (s, 3H), 3.15-3.3 (m, 2H), 3.34 (dd, J=7 and 2 Hz, 1H), 3.47 (s, 1H), 3.60 (d, J=6 Hz, 1H), 3.68 (d, J=10 Hz, 1H), 4.72 (d, J=10 Hz, 1H), 5.07 (dd, J=12 and 8 Hz, 1H), 6.03 (dd, J=15 and 6 Hz, 1H), 6.18 (d, J=12 Hz, 1H), 6.30 (d, J=10 Hz, 1H), 6.40 (dd, J=15 and 10 Hz, 1H), 8.23 (s, 1H), 8.78 (s, 1H) 12.93 (s, 1H), 14.21 (s, 1H).

Preparation of RTI-44 11-deoxy-11-imino-4-deoxy-3,4[2-spiro-[piperidin-4-yl]]-(1H)-imidazo-(2,5-dihydro)rifamycin S Following the general procedure (A), the title compound was obtained as a pure solid. HRMS (ESI$^+$): 790.4078 (M+H)$^+$; calculated for (M+H)$^+$: 790.4029; RTI-044C, 1H-NMR (300 MHz, CDCl3): −0.08 (d, J=7 Hz, 3H), 0.61 (d, J=7 Hz, 3H), 0.85 (d, J=7 Hz, 3H), 1.05 (d, J=7 Hz, 3H), 1.44 (m, 1H), 1.75-1.85 (m, 2H), 1.89 (s, 3H), 2.02 (s, 3H), 2.07 (s, 3H), 1.85-2.15 (m, 4H), 2.35 (s, 3H), 2.40 (m, 1H), 3.00 (m, 1H), 3.09 (s, 3H), 3.15-3.3 (m, 2H), 3.3-3.45 (m, 4H), 3.50 (s, 1H), 3.45-3.65 (br, 1H), 3.69 (d, J=10 Hz, 1H), 4.75 (d, J=10 Hz, 1H), 5.08 (dd, J=12 and 7 Hz, 1H), 6.04 (dd, J=15 and 6 Hz, 1H), 6.18 (d, J=12 Hz, 1H), 6.30 (d, J=10 Hz, 1H), 6.42 (dd, J=15 and 10 Hz, 1H), 8.24 (s, 1H), 8.82 (s, 1H), 13.00 (s, 1H), 14.28 (s, 1H).

Preparation of RTI-46 11-deoxy-11-imino-4-deoxy-3,4[2-spiro-cyclohexyl]-(1H)-imidazo-(2,5-dihydro)rifamycin S Following the general procedure (A), the title compound was obtained as a pure solid. HRMS (ESI$^+$): 789.4122 (M+H)$^+$; calculated for (M+H)$^+$: 789.4076; RTI-046C, 1H-NMR (300 MHz, CDCl3): −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.7-1.9 (m, 10H), 1.89 (s, 3H), 2.01 (s, 3H), 2.06 (s, 3H), 1.95-2.1 (m, 2H), 2.33 (s, 3H), 2.40 (m, 1H), 3.00 (m, 1H), 3.08 (s, 3H), 3.34 (dd, J=7 and 3 Hz, 1H), 3.45 (s, 1H), 3.62 (d, J=6 Hz, 1H), 3.68 (d, J=10 Hz, 1H), 4.75 (d, J=10 Hz, 1H), 5.08 (dd, J=12 and 7 Hz, 1H), 6.03 (dd, J=15 and 6 Hz, 1H), 6.16 (d, J=12 Hz, 1H), 6.27 (d, J=10 Hz, 1H), 6.40 (dd, J=15 and 10 Hz, 1H), 8.21 (s, 1H), 8.87 (s, 1H), 13.00 (s 1H), 14.33 (s, 1H).

Preparation of RTI-49 11-deoxy-11-imino-4-deoxy-3,4[2-spiro-[1-(benzyl)-piperidin-4-yl]]-(1H)-imidazo-(2,5-dihydro)rifamycin S Following the general procedure (A), the title compound was obtained as a pure solid. HRMS (ESI$^+$): 880.4535 (M+H)$^+$; calculated for (M+H)$^+$: 880.4498; RTI-049A, 1H-NMR (300 MHz, CDCl3); −0.09 (d, J=7 Hz, 3H), 0.60 (d, J=7 Hz, 3H), 0.84 (d, J=7 Hz, 3H), 1.04 (d, J=7 Hz, 3H), 1.44 (m, 1H), 1.65-1.85 (m, 2H), 1.91 (s, 3H), 2.01 (s, 3H), 2.07 (s, 3H), 2.35 (s, 3H), 2.40 (m, 1H), 2.47 (t, J=6 Hz, 2H), 2.76 (t, J=6 Hz, 2H), 2.8-2.95 (m, 4H), 3.00 (m, 1H), 3.09 (s, 3H), 3.33 (dd, J=7 and 2 Hz, 1H), 3.46 (s, 1H), 3.60-3.72 (m, 4H), 4.74 (d, J=10 Hz, 1H), 5.08 (dd, J=12 and 7 Hz, 1H), 6.04 (dd, J=16 and 7 Hz, 1H), 6.18 (d, J=12 Hz, 1H), 6.27 (d, J=10 Hz, 1H), 6.40 (dd, J=16 and 10 Hz, 1H), 7.3-7.45 (m, 5H), 8.22 (s, 1H), 8.80 (s, 1H), 12.99 (s, 1H), 14.31 (s, 1H).

Preparation of RTI-51 11-deoxy-11-imino-4-deoxy-3,4[2-spiro-[1-(2-methoxyethyl)-piperidin-4-yl]]-(1H)-imidazo-(25-dihydro)rifamycin S Following the general procedure (A), the title compound was obtained as a pure solid. HRMS (ESI$^+$): 848.4487 (M+H)$^+$; calculated for (M+H)$^+$: 848.4447; RTI-051A, 1H-NMR (300 MHz, CDCl3); −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.65-1.85 (m, 4H), 1.90 (s, 3H), 2.02 (s, 3H), 2.07 (s, 3H), 1.85-2.15 (br, 2H), 2.35 (s, 3H), 2.40 (m, 1H), 2.79 (t, J=5 Hz, 2H), 2.85-2.95 (m, 4H), 3.00 (m, 1H), 3.09 (s, 3H), 3.33 (dd, J=7 and 2 Hz, 1H), 3.41 (s, 3H), 3.49 (s, 1H), 3.59 (t, J=5 Hz, 2H), 3.64 (d, J=6 Hz, 1H), 3.68 (d, J=10 Hz, 1H), 4.75 (d, J=10 Hz, 1H), 5.08 (dd, J=12 and 7 Hz, 1H), 6.04 (dd, J=15 and 7 Hz, 1H), 6.16 (d, J=12 Hz, 1H), 6.27 (d, J=10 Hz, 1H), 6.41 (dd, J=15 and 10 Hz, 1H), 8.25 (s, 1H), 8.77 (s, 1H), 12.94 (s, 1H), 14.31 (s, 1H).

Preparation of RTI-53 11-deoxy-11-imino-4-deoxy-3,4[2-spiro-[1-(2-morpholinoethyl)-piperidin-4-yl]]-(1H)-imidazo-(2,5-dihydro)rifamycin S Following the general procedure (A), the title compound was obtained as a pure solid. HRMS (ESI$^+$): 903.4904 (M+H)$^+$; calculated for (M+H)$^+$: 903.4869; RTI-053A, 1H-NMR (300 MHz, CDCl3); −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.65-1.85 (m, 4H), 1.90 (s, 3H), 2.02 (s, 3H), 2.07 (s, 3H), 1.85-2.15 (br, 2H), 2.34 (s, 3H), 2.40 (m, 1H), 2.5-2.65 (m, 6H), 2.74 (m, 2H), 2.85-2.95 (m, 4H), 3.00 (m, 1H), 3.09 (s, 3H), 3.33 (dd, J=7 and 2 Hz, 1H), 3.49 (s, 1H), 3.64 (d, J=6 Hz, 1H), 3.68 (d, J=10 Hz, 1H), 3.74 (t, J=5 Hz, 4H), 4.75 (d, J=10 Hz, 1H), 5.08 (dd, J=12 and 7 Hz, 1H), 6.04 (dd, J=15 and 7 Hz, 1H), 6.16 (d, J=12 Hz, 1H), 6.28 (d, J=10 Hz, 1H), 6.40 (dd, J=15 and 10 Hz, 1H), 8.25 (s, 1H), 8.77 (s, 1H), 12.94 (s, 1H), 14.29 (s, 1H).

Preparation of RTI-57 11-deoxy-11-imino-4-deoxy-3,4[2-spiro-[1-(cyclobutylmethyl)-piperidin-4-yl]]-(1H)-imidazo-(2,5-dihydro)rifamycin S Following the general procedure (A), the title compound was obtained as a pure solid. HRMS (ESI$^+$): 858.4690

(M+H)+; calculated for (M+H)+: 858.4655; RTI-057A, 1H-NMR (300 MHz, CDCl3); −0.09 (d, J=7 Hz, 3H), 0.61 (d, J=7 Hz, 3H), 0.85 (d, J=7 Hz, 3H), 1.04 (d, J=7 Hz, 3H), 1.44 (m, 1H), 1.7-1.85 (m, 8H), 1.90 (s, 3H), 1.9-2.15 (m, 4H), 2.02 (s, 3H), 2.07 (s, 3H), 2.35 (s, 3H), 2.40 (m, 1H), 2.60 (m, 3H), 2.7-2.9 (br, 4H), 3.00 (m, 1H), 3.09 (s, 3H), 3.34 (dd, J=7 and 2 Hz, 1H), 3.46 (s, 1H), 3.63 (d, J=6 Hz, 1H), 3.68 (d, J=10 Hz, 1H), 4.75 (d, J=10 Hz, 1H), 5.08 (dd, J=12 and 7 Hz, 1H), 6.03 (dd, J=16 and 7 Hz, 1H), 6.17 (d, J=12 Hz 1H), 6.28 (d, J=10 Hz, 1H), 6.40 (dd, J=16 and 10 Hz, 1H), 8.22 (s, 1H), 8.80 (s, 1H), 12.95 (s, 1H), 14.31 (s, 1H).

Preparation of RTI-59 11-deoxy-11-imino-4-deoxy-3,4[2-spiro-[1-(cyclopropylmethyl)-piperidin-4-yl]]-(1H)-imidazo-(2,5-dihydro)rifamycin S Following the general procedure (A), the title compound was obtained as a pure solid. HRMS (ESI+): 844.4536 (M+H)+; calculated for (M+H)+: 844.4498; RTI-059A, 1H-NMR (300 MHz, CDCl3); −0.09 (d, J=7 Hz, 3H), 0.18 (m, 2H), 0.57 (m, 2H), 0.61 (d, J=7 Hz, 3H), 0.84 (d, J=7 Hz, 3H), 0.93 (m, 1H), 1.04 (d, J=7 Hz, 3H), 1.44 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.46 (d, J=7 Hz, 2H), 2.8-3.05 (m, 5H), 3.09 (s, 3H), 3.35 (dd, J=7 and 2 Hz, 1H), 3.49 (s, 1H), 3.63 (d, J=6 Hz, 1H), 3.68 (d, J=10 Hz, 1H), 4.74 (d, J=10 Hz, 1H), 5.07 (dd, J=12 and 7 Hz, 1H), 6.03 (dd, J=16 and 7 Hz, 1H), 6.17 (d, J=12 Hz, 1H), 6.28 (d, J=10 Hz, 1H), 6.40 (dd, J=16 and 10 Hz, 1H), 8.25 (s, 1H), 8.78 (s, 1H), 12.93 (s, 1H), 14.31 (s, 1H).

Preparation of RTI-60 11-deoxy-11-imino-4-deoxy-3,4[2-spiro-[1-(isopropyl)-piperidin-4-yl]]-(1H)-imidazo-(2,5-dihydro)rifamycin S Following the general procedure (A), the title compound was obtained as a pure solid. HRMS (ESI+): 832.4542 (M+H)+; calculated for (M+H)+: 832.4498; RTI-060A, 1H-NMR (300 MHz, CDCl3); −0.09 (d, J=7 Hz, 3H), 0.60 (d, J=7 Hz, 3H), 0.84 (d, J=7 Hz, 3H), 1.04 (d, J=7 Hz, 3H), 1.16 (d, J=6 Hz, 6H), 1.44 (m, 1H), 1.7-1.8 (m, 4H), 1.88 (s, 3H), 1.95-2.15 (br, 2H), 2.01 (s, 3H), 2.05 (s, 3H), 2.33 (s, 3H), 2.40 (m, 1H), 2.75-3.05 (m, 6H), 3.08 (s, 3H), 3.34 (dd, J=7 and 2 Hz, 1H), 3.47 (s, 1H), 3.64 (d, J=6 Hz, 1H), 3.68 (d, J=10 Hz, 1H), 4.75 (d, J=10 Hz, 1H), 5.07 (dd, J=12 and 7 Hz, 1H), 6.03 (dd, J=16 and 7 Hz, 1H), 6.16 (d, J=12 Hz, 1H), 6.27 (d, J=10 Hz, 1H), 6.40 (dd, J=16 and 10 Hz, 1H), 8.22 (s, 1H), 8.76 (s, 1H) 12.91 (s, 1H), 14.31 (s, 1H).

Preparation of RTI-61 11-deoxy-11-imino-4-deoxy-3,4[2-spiro-[1-(t-ethyloxycarbonyl)-piperidin-4-yl]]-(1H)-imidazo-(2,5-dihydro)rifamycin S Following the general procedure (A), the title compound was obtained as a pure solid. HRMS (ESI+): 862.4270 (M+H)+; calculated for (M+H)+: 862.4240; RTI-61A, 1H-NMR (300 MHz, CDCl3); −0.08 (d, J=7 Hz, 3H), 0.62 (d, J=7 Hz, 3H), 0.84 (d, J=7 Hz, 3H), 1.04 (d, J=7 Hz, 3H), 1.30 (t, J=7 Hz, 3H), 1.44 (m, 1H), 1.6-1.85 (m, 4H), 1.89 (s, 3H), 2.0-2.15 (m, 2H), 2.02 (s, 3H), 2.06 (s, 3H), 2.35 (s, 3H), 2.40 (m, 1H), 3.00 (m, 1H), 3.09 (s, 3H), 3.33 (m, 1H), 3.50 (s, 1H), 3.61 (d, J=5 Hz, 1H), 3.68 (d, J=10 Hz, 1H), 3.6-3.8 (br, 2H), 4.0-4.2 (br, 2H), 4.21 (q, J=7 Hz, 2H), 4.72 (d, J=10 Hz, 1H), 5.07 (dd, J=12 and 7 Hz, 1H), 6.03 (dd, J=16 and 7 Hz, 1H), 6.17 (d, J=12 Hz, 1H), 6.29 (d, J=10 Hz, 1H), 6.41 (dd, J=16 and 10 Hz, 1H), 8.26 (s, 1H), 8.72 (bs, 1H), 12.93 (s, 1H), 14.21 (s, 1H).

Preparation of RTI-63 11-deoxy-11-imino-4-deoxy-3,4[2-spiro-[1-(acetyl)-piperidin-4-yl]]-(1H)-imidazo-(2,5-dihydro)rifamycin S Following the general procedure (A), the title compound was obtained as a pure solid. HRMS (ESI+): 832.4181 (M+H)+; calculated for (M+H)+: 832.4134. RTI-63A, 1H-NMR (300 MHz, CDCl3); −0.06 (d, J=7 Hz, 3H), 0.62 (d, J=7 Hz, 3H), 0.85 (d, J=7 Hz, 3H), 1.04 (d, J=7 Hz, 3H), 1.45 (m, 1H), 1.6-1.85 (m, 4H), 1.89 (s, 3H), 2.03 (s, 3H), 2.06 (s, 3H), 2.0-2.2 (m, 2H), 2.20 (s, 3H), 2.35 (s, 3H), 2.40 (m, 1H), 3.00 (m, 1H), 3.10 (s, 3H), 3.33 (m, 1H), 3.47 (s, 0.4H), 3.51 (s, 0.6H), 3.55-3.70 (m, 3H), 3.90 (m, 2H), 4.48 (m, 1H), 4.73 (m, 1H), 5.07 (m, 1H), 6.03 (dd, J=16 and 6 Hz, 1H), 6.18 (d, J=12 Hz, 1H), 6.29 (d, J=10 Hz, 1H), 6.38 (m, 1H), 8.25 (s, 1H), 8.66 (s, 0.6H), 8.71 (s, 0.4H), 12.92 (s, 1H), 14.16 (s, 0.4H), 14.19 (s, 0.6H).

Preparation of RTI-64 11-deoxy-11-imino-4-deoxy-3,4[2-spiro-[1-(n-propyl)-piperidin-4-yl]]-(1H)-imidazo-(2,5-dihydro)rifamycin S Following the general procedure (A), the title compound was obtained as a pure solid. HRMS (ESI+): 832.4552 (M+H)+; calculated for (M+H)+: 832.4498; RTI-064A, 1H-NMR (300 MHz, CDCl3); −0.09 (d, J=7 Hz, 3H), 0.61 (d, J=7 Hz, 3H), 0.85 (d, J=7 Hz, 3H), 0.96 (t, J=7 Hz, 3H), 1.04 (d, J=7 Hz, 3H), 1.44 (m, 1H), 1.55-1.65 (m, 2H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.54 (m, 2H), 2.8-2.9 (m, 4H), 3.00 (m, 1H), 3.09 (s, 3H), 3.35 (dd, J=7 and 2 Hz, 1H), 3.46 (s, 1H), 3.62 (d, J=6 Hz, 1H), 3.67 (d, J=10 Hz, 1H), 4.75 (d, J=10 Hz, 1H), 5.07 (dd, J=12 and 7 Hz, 1H), 6.03 (dd, J=16 and 7 Hz, 1H), 6.17 (d, J=12 Hz, 1H), 6.27 (d, J=10 Hz, 1H), 6.40 (dd, J=16 and 10 Hz, 1H), 8.21 (s, 1H), 8.78 (s, 1H), 12.95 (s, 1H), 14.30 (s, 1H).

Preparation of RTI-65 11-deoxy-11-imino-4-deoxy-3,4[2-spiro-[1-(cyclopropyl)-piperidin-4-yl]]-(1H)-imidazo-(2,5-dihydro)rifamycin S Following the general procedure (A), the title compound was obtained as a pure solid. HRMS (ESI+): 830.4386 (M+H)+; calculated for (M+H)+: 830.4342; RTI-065A, 1H-NMR (300 MHz, CDCl3); −0.09 (d, J=7 Hz, 3H), 0.45-0.55 (m, 5H), 0.61 (d, J=7 Hz, 3H), 0.85 (d, J=7 Hz, 3H), 1.04 (d, J=7 Hz, 3H), 1.44 (m, 1H) 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.9-3.1 (m, 5H), 3.09 (s, 3H), 3.35 (dd, J=7 and 2 Hz, 1H), 3.46 (s, 1H), 3.63 (d, J=6 Hz, 1H), 3.67 (d, J=10 Hz, 1H), 4.75 (d, J=10 Hz, 1H), 5.08 (dd, J=12 and 7 Hz, 1H), 6.04 (dd, J=16 and 7 Hz, 1H), 6.17 (d, J=12 Hz, 1H), 6.27 (d, J=10 Hz, 1H), 6.40 (dd, J=16 and 10 Hz, 1H), 8.21 (s, 1H), 8.79 (s, 1H), 12.97 (s, 1H), 14.30 (s, 1H).

Preparation of RTI-66 11-deoxy-11-imino-4-deoxy-3,4[2-spiro-[1-(ethyl)-piperidin-4-yl]]-(1H)-imidazo-(2,5-dihydro)rifamycin S Following the general procedure (A), the title compound was obtained as a pure solid. HRMS (ESI+): 818.4388 (M+H)+; calculated for (M+H)+: 818.4342; RTI-066A, 1H-NMR (300 MHz, CDCl3); −0.08 (d, J=7 Hz, 3H), 0.61

(d, J=7 Hz, 3H), 0.85 (d, J=7 Hz, 3H), 1.04 (d, J=7 Hz, 3H), 1.18 (t, J=7 Hz, 3H), 1.44 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.64 (q, J=7 Hz, 2H), 2.8-2.95 (m, 4H), 3.00 (m, 1H), 3.09 (s, 3H), 3.35 (d, J=7 Hz, 1H), 3.46 (s, 1H), 3.63 (d, J=6 Hz, 1H), 3.67 (d, J=10 Hz, 1H), 4.75 (d, J=10 Hz, 1H), 5.08 (dd, J=12 and 7 Hz, 1H), 6.04 (dd, J=16 and 7 Hz, 1H), 6.16 (d, J=12 Hz, 1H), 6.27 (d, J=10 Hz, 1H), 6.40 (dd, J=16 and 10 Hz, 1H), 8.22 (s, 1H), 8.77 (s, 1H), 12.95 (s, 1H), 14.29 (s, 1H).

Preparation of RTI-67 11-deoxy-11-imino-4-deoxy-3,4[2-spiro-[1-(beRTIoyl)-piperidin-4-yl]]-(1H)-imidazo-(2,5-dihydro)rifamycin S Following the general procedure (A), the title compound was obtained as a pure solid. HRMS (ESI$^+$): 916.4169 (M+Na)$^+$; calculated for (M+Na)$^+$: 916.4109. RTI-67A, 1H-NMR (300 MHz, CDCl3); −0.07 (br, 3H), 0.60 (br, 3H), 0.84 (br, 3H), 1.02 (d, J=7 Hz, 3H), 1.45 (m, 1H), 1.6-1.85 (m, 4H), 1.88 (s, 3H), 2.00 (s, 3H), 2.04 (s, 3H), 1.9-2.2 (m, 2H), 2.34 (s, 3H), 2.40 (m, 1H), 3.00 (m, 1H), 3.08 (s, 3H), 3.2-3.9 (br, 7H), 4.2 (br, 1H), 4.6 (br, 1H), 5.05 (br, 1H), 6.0 (br, 1H), 6.18 (br, 1H), 6.29 (br, 1H), 6.40 (br, 1H), 7.40 (m, 2H), 7.45 (m, 3H), 8.25 (s, 1H), 8.6 (brs, 1H), 12.93 (s, 1H), 14.16 (s, 1H).

Preparation of RTI-68 11-deoxy-11-imino-4-deoxy-3,4[2-spiro-[1-(benzyloxycarbonyl)-piperidin-4-yl]]-(1H)-imidazo-(2,5-dihydro)rifamycin S Following the general procedure (A), the title compound was obtained as a pure solid. HRMS (ESI$^+$): 924.4435 (M+H)$^+$; calculated for (M+H)$^+$: 924.4396; RTI-68A, 1H-NMR (300 MHz, CDCl3); −0.09 (d, J=7 Hz, 3H), 0.60 (d, J=7 Hz, 3H), 0.84 (d, J=7 Hz, 3H), 1.04 (d, J=7 Hz, 3H), 1.44 (m, 1H), 1.6-1.85 (m, 4H), 1.88 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (br, 1H), 3.49 (s, 1H), 3.60 (d, J=5 Hz, 1H), 3.68 (d, J=10 Hz, 1H), 3.6-3.8 (br, 2H), 4.0-4.2 (m, 2H), 4.72 (d, J=10 Hz, 1H), 5.07 (dd, J=12 and 7 Hz, 1H), 5.20 (s, 2H), 6.03 (dd, J=16 and 7 Hz, 1H), 6.17 (d, J=12 Hz, 1H), 6.29 (d, J=10 Hz, 1H), 6.41 (dd, J=16 and 10 Hz, 1H), 7.38 (m, 5H), 8.26 (s, 1H), 8.70 (bs, 1H), 12.92 (s, 1H), 14.20 (s, 1H).

Preparation of RTI-69 11-deoxy-11-imino-4-deoxy-3,4[2-spiro-[1-(methyl)-piperidin-4-yl]]-(1H)-imidazo-(2,5-dihydro)rifamycin S Following the general procedure (A) the title compound was obtained as a pure solid. HRMS (ESI$^+$): 804.4213 (M+H)$^+$; calculated for (M+H)$^+$: 804.4185; RTI-069A 1H-NMR (300 MHz, CDCl3); −0.08 (d, J=7 Hz, 3H), 0.61 (d, J=7 Hz, 3H), 0.85 (d, J=7 Hz, 3H), 1.04 (d, J=7 Hz, 3H), 1.45 (m, 1H), 1.7-1.85 (m, 4H), 1.90 (s, 3H), 1.95-2.15 (br, 2H), 2.02 (s, 3H), 2.07 (s, 3H), 2.35 (s, 3H), 2.40 (m, 1H), 2.49 (s, 3H), 2.7-2.95 (m, 4H), 3.00 (m, 1H), 3.09 (s, 3H), 3.34 (d, J=7 Hz, 1H), 3.48 (s, 1H), 3.63 (d, J=6 Hz, 1H), 3.68 (d, J=10 Hz, 1H), 4.75 (d, J=10 Hz, 1H), 5.08 (dd, J=12 and 7 Hz, 1H), 6.04 (dd, J=16 and 7 Hz, 1H), 6.17 (d, J=12 Hz, 1H), 6.27 (d, J=10 Hz, 1H), 6.40 (dd, J=16 and 10 Hz, 1H), 8.23 (s, 1H), 8.77 (s, 1H), 12.95 (s, 1H), 14.29 (s, 1H).

Preparation of RTI-70 11-deoxy-11-imino-4-deoxy-3,4[2-spiro-[1-(2-methylpropyl)-piperidin-4-yl]]-(1H)-imidazo-(2,5-dihydro)rifamycin S Following the general procedure (A), the title compound was obtained as a pure solid. HRMS (ESI$^+$): 846.4682 (M+H)$^+$; calculated for (M+H)$^+$: 846.4655; RTI-070A 1H-NMR (500 MHz, CDCl3); −0.09 (d, J=7 Hz, 3H), 0.60 (d, J=7 Hz, 3H), 0.84 (d, J=7 Hz, 3H), 0.94 (d, J=7 Hz, 6H), 1.04 (d, J=7 Hz, 3H), 1.44 (m, 1H), 1.74-1.85 (m, 3H), 1.89 (s 3H) 1.9-2.15 (m 4H), 2.01 (s, 3H), 2.05 (s, 3H), 2.29 (d, J=7 Hz, 2H), 2.33 (s, 3H), 2.40 (m, 1H), 2.75-2.85 (m, 4H), 3.00 (m, 1H), 3.08 (s, 3H), 3.33 (dd, J=7 and 2 Hz, 1H), 3.46 (s, 1H), 3.63 (d, J=6 Hz, 1H), 3.68 (d, J=10 Hz, 1H), 4.75 (dd, J=10 and 2 Hz, 1H), 5.07 (dd, J=12 and 7 Hz, 1H), 6.03 (dd, J=16 and 7 Hz, 1H), 6.16 (d, J=12 Hz, 1H), 6.27 (d, J=10 Hz, 1H), 6.40 (dd, J=16 and 10 Hz, 1H), 8.23 (s, 1H), 8.78 (s, 1H), 12.96 (s, 1H), 14.30 (s, 1H), 13C-NMR (125 MHz, CDCl3).

Preparation of RTI-74 11-deoxy-11-imino-4-deoxy-3,4[2-spiro-[1-(phenylaminocarbonyl)-piperidin-4-yl]]-(1H)-imidazo-(2,5-dihydro)rifamycin S Following the general procedure (A), the title compound was obtained as a pure solid. HRMS (ESI$^+$): 909.4433 (M+H)$^+$; calculated for (M+H)$^+$: 909.4400; RTI-074A, 1H-NMR (300 MHz, CDCl3); −0.07 (d J=7 Hz, 3H), 0.62 (d, J=7 Hz, 3H), 0.84 (d, J=7 Hz, 3H), 1.04 (d, J=7 Hz, 3H), 1.44 (m, 1H), 1.6-1.85 (m, 3H), 1.89 (s, 3H), 1.9-2.25 (m, 3H), 2.02 (s, 3H), 2.05 (s, 3H), 2.35 (s, 3H), 2.40 (m, 1H), 3.00 (m, 1H), 3.09 (s, 3H), 3.33 (m, 1H), 3.51 (s, 1H), 3.61 (d, J=6 Hz, 1H), 3.68 (d, J=10 Hz, 1H), 3.6-3.8 (br, 2H), 4.0-4.2 (br, 2H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (m, 2H), 7.15 (m, 1H), 7.34 (m, 4H), 8.27 (s, 1H), 8.69 (s, 1H), 12.92 (s, 1H), 14.19 (s, 1H).

Preparation of RTI-77 11-deoxy-11-imino-4-deoxy-3,4[2-spiro-[1-(ethyloxycarbonyl)-piperidin-4-yl]]-(1H)-imidazo-(2,5-dihydro)rifamycin S Following the general procedure (A), the title compound was obtained as a pure solid. HRMS (ESI$^+$): 876.4417 (M+H)$^+$; calculated for (M+H)$^+$: 876.4396; RTI-77A, 1H-NMR (300 MHz, CDCl3); −0.08 (d, J=7 Hz, 3H), 0.61 (d, J=7 Hz, 3H), 0.84 (d, J=7 Hz, 3H), 1.04 (d, J=7 Hz, 3H), 0.99 (t, J=7 Hz, 3H), 1.44 (m, 1H), 1.6-1.85 (m, 6H), 1.88 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.49 (s, 1H), 3.60 (d, J=5 Hz, 1H), 3.68 (d, J=10 Hz, 1H), 3.6-3.8 (br, 2H), 4.0-4.2 (m, 4H), 4.72 (d, J=10 Hz, 1H), 5.07 (dd, J=12 and 7 Hz, 1H), 6.03 (dd, J=16 and 7 Hz, 1H), 6.17 (d, J=12 Hz, 1H), 6.28 (d, J=10 Hz, 1H), 6.41 (dd, J=16 and 10 Hz, 1H), 8.25 (s, 1H), 8.7 (bs, 1H), 12.93 (s, 1H), 14.20 (s, 1H).

Preparation of RTI-81 11-deoxy-11-imino-4-deoxy-3,4[2-spiro-[1-(isobutyloxycarbonyl)-piperidin-4-yl]]-(1H)-imidazo-(2,5-dihydro)rifamycin S Following the general procedure (A), the title compound was obtained as a pure solid. HRMS (ESI$^+$): 890.4552 (M+H)$^+$; calculated for (M+H)$^+$: 890.4553; RTI-081, 1H-NMR (300 MHz, CDCl3); −0.09 (d, J=7 Hz, 3H), 0.61 (d, J=7 Hz, 3H), 0.84 (d, J=7 Hz, 3H), 0.98 (d, J=7 Hz, 6H), 1.04 (d, J=7 Hz, 3H), 1.44 (m, 1H), 1.6-1.85 (m, 4H), 1.88 (s, 3H), 1.9-2.15 (m, 3H), 2.01 (s, 3H), 2.05 (s, 3H), 2.35 (s, 3H), 2.40 (m, 1H), 3.00 (m, 1H), 3.09 (s, 3H), 3.33 (m, 1H), 3.49 (s, 1H), 3.60 (d, J=6 Hz, 1H), 3.68 (d, J=10 Hz, 1H), 3.6-3.8 (br, 2H), 3.95 (m, 2H), 4.0-4.2 (br, 2H), 4.72 (d, J=10 Hz, 1H), 5.07 (dd, J=12 and 7 Hz, 1H), 6.03 (dd, J=16 and 7 Hz 1H), 6.16 (d, J=12 Hz, 1H), 6.27 (d, J=10 Hz, 1H), 6.40 (dd, J=16 and 10 Hz, 1H), 8.25 (s, 1H), 8.7 (bs, 1H), 12.93 (s, 1H), 14.20 (s, 1H).

Preparation of RTI-82 11-deoxy-11-imino-4-deoxy-3,4[2-spiro-[1-(ethylaminocarbonyl)-piperidin-4-yl]]-(1H)-imidazo-(2,5-dihydro)rifamycin S Following the general procedure (A), the title compound was obtained as a pure solid. HRMS (ESI+): 883.4175 (M+Na)+; calculated for (M+Na)+: 883.4218; RTI-082A, 1H-NMR (300 MHz, CDCl3); −0.08 (d, J=7 Hz, 3H), 0.61 (d, J=7 Hz, 3H), 0.84 (d, J=7 Hz, 3H), 1.04 (d, J=7 Hz, 3H), 1.20 (t, J=7 Hz, 3H), 1.44 (m, 1H), 1.6-1.85 (m, 3H), 1.88 (s, 3H), 1.9-2.25 (m, 3H), 2.02 (s, 3H), 2.05 (s, 3H), 2.35 (s, 3H), 2.40 (m, 1H), 3.00 (m, 1H), 3.09 (s, 3H), 3.3-3.4 (m, 3H), 3.50 (s, 1H), 3.61 (d, J=6 Hz, 1H), 3.68 (d, J=10 Hz, 1H), 3.6-3.7 (br, 2H), 3.8-4.0 (br, 2H), 4.52 (m, 1H), 4.72 (d, J=10 Hz, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (m, 1H), 8.25 (s, 1H), 8.69 (s, 1H), 12.92 (s, 1H), 14.20 (s, 1H).

Preparation of RTI-83 4-deoxy-3,4[2-spiro-[1-(ethylaminocarbonyl)-piperidin-4-yl]]-(1H)-imidazo-(2,5-dihydro)rifamycin S Following the general procedure (B), the title compound was obtained as a pure solid. HRMS (ESI+): 884.4048 (M+Na)+; calculated for (M+Na)+: 884.4058; RTI-083A, 1H-NMR (300 MHz, CDCl3); −0.04 (d, J=7 Hz, 3H), 0.61 (d, J=7 Hz, 3H), 0.84 (d, J=7 Hz, 3H,) 1.04 (d, J=7 Hz, 3H), 1.20 (t, J=7 Hz, 3H), 1.4-1.6 (m, 2H), 1.65-1.85 (m, 3H), 1.74 (s, 3H), 1.95-2.2 (m, 2H), 2.02 (s, 3H), 2.04 (s, 3H), 2.35 (s, 3H), 2.40 (m, 1H), 3.00 (m, 1H), 3.09 (s, 3H), 3.3-3.4 (m, 3H), 3.43 (s, 1H), 3.56 (d, J=6 Hz, 1H), 3.68 (d, J=10 Hz, 1H), 3.7-4.0 (m, 4H), 4.50 (m, 1H), 4.72 (d, J=10 Hz, 1H), 5.13 (dd, J=12 and 7 Hz, 1H), 6.03 (dd, J=16 and 7 Hz, 1H), 6.18 (d, J=12 Hz, 1H), 6.27 (d, J=10 Hz, 1H), 6.38 (m, 1H), 8.18 (s, 1H), 8.90 (s, 1H), 14.57 (s, 1H).

Preparation of RTI-84 11-deoxy-11-imino-4-deoxy-3,4[2-spiro-[1-(isopropyloxycarbonyl)-piperidin-4-yl]]-(1H)-imidazo-(2,5-dihydro)rifamycin S Following the general procedure (A) the title compound was obtained as a pure solid. HRMS (ESI+): 898.4203 (M+Na)+; calculated for (M+Na)+: 898.4215; RTI-084A, 1H-NMR (300 MHz, CDCl3); −0.09 (d, J=7 Hz, 3H), 0.61 (d, J=7 Hz, 3H), 0.84 (d, J=7 Hz, 3H), 1.04 (d, J=7 Hz, 3H), 1.30 (d, J=6 Hz, 6H), 1.44 (m, 1H), 1.6-1.85 (m, 4H), 1.88 (s, 3H), 1.9-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.50 (s, 1H), 3.61 (d, J=6 Hz, 1H), 3.68 (d, J=10 Hz, 1H), 3.6-3.8 (br, 2H), 4.0-4.2 (br, 2H), 4.72 (d, J=10 Hz, 1H), 4.99 (m, 1H), 5.07 (dd, J=12 and 7 Hz, 1H), 6.03 (dd, J=16 and 7 Hz, 1H), 6.16 (d, J=12 Hz, 1H), 6.28 (d, J=10 Hz, 1H), 6.40 (dd, J=16 and 10 Hz, 1H), 8.27 (s, 1H), 8.7 (bs, 1H), 12.93 (s, 1H), 14.21 (s, 1H).

Preparation of RTI-86 4-deoxy-3,4[2-spiro-[1-(phenylaminocarbonyl)-piperidin-4-yl]]-(1H)-imidazo-(2,5-dihydro)rifamycin S Following the general procedure (B), the title compound was obtained as a pure solid. HRMS (ESI+): 932.4038 (M+Na)+; calculated for (M+Na)+: 932.4058; RTI-086A, 1H-NMR (300 MHz, CDCl3); −0.02 (d, J=7 Hz, 3H), 0.62 (d, J=7 Hz, 3H), 0.84 (d, J=7 Hz, 3H), 1.04 (d, J=7 Hz, 3H), 1.4-1.6 (m, 2H), 1.65-1.85 (m, 3H), 1.75 (s, 3H), 1.95-2.2 (m, 3H), 2.02 (s, 3H), 2.05 (s, 3H), 2.35 (s, 3H), 3.00 (m, 1H), 3.09 (s, 3H), 3.3 (m, 1H), 3.45 (s, 1H), 3.58 (d, J=6 Hz, 1H), 3.67 (d, J=10 Hz, 1H), 3.8-4.2 (m, 4H), 4.72 (d, J=10 Hz, 1H), 5.13 (dd, J=12 and 7 Hz, 1H), 6.03 (dd, J=16 and 7 Hz, 1H), 6.18 (d, J=12 Hz, 1H), 6.27 (d, J=10 Hz, 1H), 6.38 (m, 1H), 6.44 (s, 1H), 7.10 (m, 1H), 7.37 (m, 4H), 8.21 (s, 1H), 8.88 (s, 1H), 14.56 (s, 1H).

Preparation of RTI-91 11-deoxy-11-imino-4-deoxy-3,4[2-spiro-[1-(3,3-dimethylbutanoyl)-piperidin-4-yl]]-(1H)-imidazo-(2,5-dihydro)rifamycin S Following the general procedure (A), the title compound was obtained as a pure solid. HRMS (ESI+): 910.4589 (M+Na)+; calculated for (M+Na)+: 910.4579; RTI-91A, 1H-NMR (300 MHz, CDCl3); −0.07 (d, J=7 Hz, 3H), 0.61 (d, J=7 Hz, 3H), 0.85 (d, J=7 Hz, 3H), 1.05 (m, 3H), 1.10 (s, 9H), 1.45 (m, 1H), 1.6-1.85 (m, 4H), 1.88 (s, 3H), 2.02 (s, 3H), 2.05 (s, 3H), 2.0-2.2 (m, 2H), 2.35 (s, 3H), 2.3-2.45 (m, 3H), 3.00 (m, 1H), 3.09 (s, 3H), 3.33 (m, 1H), 3.47 (s, 0.4H), 3.52 (s, 0.6H), 3.55-3.70 (m, 3H), 3.8-4.0 (m, 2H), 4.5 (m, 1H), 4.75 (m, 1H), 5.06 (m, 1H), 6.0 (m, 1H), 6.17 (m, 1H), 6.29 (d, J=10 Hz, 1H), 6.4 (m, 1H), 8.27 (s, 1H) 8.63 (s, 0.6H), 8.71 (s, 0.4H), 12.92 (s, 1H), 14.16 (s, 0.4H), 14.20 (s, 0.6H).

Preparation of RTI-94 11-deoxy-11-imino-4-deoxy-3,4[2-spiro-[1-(n-pentanoyl)-piperidin-4-yl]]-(1H)-imidazo-(2,5-dihydro)rifamycin S Following the general procedure (A), the title compound was obtained as a pure solid. HRMS (ESI+): 874.4644 (M+H)+; calculated for (M+H)+: 874.4604; RTI-94A, 1H-NMR (300 MHz, CDCl3); −0.07 (d, J=7 Hz, 3H), 0.61 (d, J=7 Hz, 3H), 0.84 (d, J=7 Hz, 3H), 0.97 (t, J=7 Hz, 3H), 1.04 (m, 3H), 1.42 (m, 3H), 1.6-1.85 (m, 6H), 1.88 (s, 3H), 2.02 (s, 3H), 2.05 (s, 3H), 1.9-2.2 (m, 2H), 2.35 (s, 3H), 2.3-2.45 (m, 3H), 3.00 (m, 1H), 3.09 (s, 3H), 3.33 (m, 1H), 3.49 (s, 0.4H), 3.53 (s, 0.6H), 3.55-3.70 (m, 3H), 3.8-4.0 (m, 2H), 4.5 (m, 1H), 4.72 (m, 1H), 5.06 (m, 1H), 6.0 (m, 1H), 6.17 (m, 1H), 6.29 (d, J=10 Hz, 1H), 6.4 (m, 1H), 8.29 (s, 1H), 8.63 (s, 0.6H), 8.70 (s, 0.4H), 12.92 (s, 1H), 14.17 (s, 0.4H), 14.20 (s, 0.6H).

Preparation of RTI-97 11-deoxy-11-imino-4-deoxy-3,4[2-spiro-[1-(2-methylpropanoyl)-piperidin-4-yl]]-(1H)-imidazo-(2,5-dihydro)rifamycin S Following the general procedure (A), the title compound was obtained as a pure solid. HRMS (ESI+): 860.4482 (M+H)+; calculated for (M+H)+: 860.4447. RTI-97A, 1H-NMR (300 MHz, CDCl3); −0.07 (d, J=7 Hz, 3H), 0.61 (d, J=7 Hz, 3H), 0.84 (d, J=7 Hz, 3H), 1.04 (m, 3H), 1.20 (d, J=7 Hz, 6H), 1.43 (m, 1H), 1.6-1.85 (m, 4H), 1.88 (s, 3H), 2.02 (s, 3H), 2.05 (s, 3H), 2.0-2.2 (m, 2H), 2.35 (s, 3H), 2.40 (m, 1H), 2.89 (m, 1H), 3.01 (m, 1H), 3.09 (s, 3H), 3.33 (m, 1H), 3.47 (s, 0.4H), 3.50 (s, 0.6H), 3.55-3.70 (m, 3H), 3.8-4.1 (m, 2H), 4.5 (m, 1H), 4.72 (m, 1H), 5.06 (m, 1H), 6.01 (dd, J=15 and 6 Hz, 1H), 6.18 (d, J=12 Hz, 1H), 6.29 (d, J=10 Hz, 1H), 6.39 (m, 1H), 8.25 (s, 1H), 8.67 (s, 0.6H), 8.70 (s, 0.4H), 12.93 (s, 1H), 14.16 (s, 0.4H), 14.19 (s, 0.6H).

Preparation of RTI-98 11-deoxy-11-imino-4-deoxy-3,4[2-spiro-[1-(3-methylbutanoyl)-piperidin-4-yl]]-(1H)-imidazo-(2,5-dihydro)rifamycin S Following the general procedure (A), the title compound was obtained as a pure solid. HRMS (ESI$^+$): 874.4632 (M+H)$^+$; calculated for (M+H)$^+$: 874.4604.RTI-98A, 1H-NMR (300 MHz, CDCl3); −0.07 (d, J=7 Hz, 3H), 0.61 (d, J=7 Hz, 3H), 0.84 (d, J=7 Hz, 3H), 1.04 (m, 3H), 1.02 (d, J=7 Hz, 6H), 1.43 (m, 1H), 1.6-1.85 (m, 4H), 1.88 (s, 3H), 2.02 (s, 3H), 2.05 (s, 3H), 2.0-2.2 (m, 3H), 2.30 (m, 3H), 2.35 (s, 3H), 2.40 (m, 1H), 3.00 (m, 1H), 3.09 (s, 3H), 3.33 (m, 1H), 3.47 (s, 0.4H), 3.50 (s, 0.6H), 3.55-3.70 (m, 3H), 3.8-4.0 (m, 2H), 4.5 (m, 1H), 4.72 (m, 1H), 5.06 (m, 1H), 6.01 (m, 1H), 6.17 (d, J=12 Hz, 0.6H), 6.18 (d, J=12 Hz, 0.4H), 6.29 (d, J=10 Hz, 1H), 6.40 (m, 1H), 8.24 (s, 1H), 8.65 (s, 0.6H), 8.72 (s, 0.4H), 12.92 (s, 1H), 14.16 (s, 0.4H), 14.19 (s, 0.6H).

Preparation of RTI-101 4-deoxy-3,4[2-spiro-[1-(dimethylaminocarbonyl)-piperidin-4-yl]]-(1H)-imidazo-(2,5-dihydro)rifamycin S Following the general procedure (B), the title compound was obtained as a pure solid. HRMS (ESI$^+$): 884.4036 (M+Na)$^+$; calculated for (M+Na)$^+$: 884.4058; RTI-101, 1H-NMR (300 MHz, CDCl3); −0.04 (d, J=7 Hz, 3H), 0.61 (d, J=7 Hz, 3H), 0.84 (d, J=7 Hz, 3H), 1.04 (d, J=7 Hz, 3H), 1.44 (m, 1H), 1.6 (m, 1H), 1.65-1.90 (m, 3H), 1.75 (s, 3H), 1.95-2.2 (m, 2H), 2.01 (s, 3H), 2.04 (s, 3H), 2.35 (s, 3H), 2.40 (m, 1H), 2.90 (s, 6H), 3.00 (m, 1H), 3.09 (s, 3H), 3.33 (m, 1H), 3.42 (s, 1H), 3.57 (d, J=6 Hz, 1H), 3.6-3.8 (m, 5H), 4.72 (d, J=10 Hz, 1H), 5.14 (dd, J=12 and 7 Hz, 1H), 6.00 (dd, J=16 and 7 Hz, 1H), 6.18 (d, J=12 Hz, 1H), 6.27 (d, J=10 Hz, 1H), 6.37 (m, 1H), 8.19 (s, 1H), 8.96 (s, 1H), 14.62 (s, 1H).

Preparation of RTI-102 4-deoxy-3,4[2-spiro-[1-(isobutylaminocarbonyl)-piperidin-4-yl]]-(1H)-imidazo-(2,5-dihydro)rifamycin S Following the general procedure (B), the title compound was obtained as a pure solid. HRMS (ESI$^+$): 912.4326 (M+Na)$^+$; calculated for (M+Na)$^+$: 912.4371; RTI-102 1H-NMR (300 MHz, CDCl3); −0.04 (d, J=7 Hz, 3H), 0.61 (d, J=7 Hz, 3H), 0.84 (d, J=7 Hz, 3H), 0.95 (d, J=7 Hz, 6H), 1.04 (d, J=7 Hz, 3H), 1.44 (m, 1H), 1.6 (m, 1H), 1.65-1.90 (m, 4H), 1.75 (s, 3H), 1.95-2.2 (m, 2H), 2.02 (s, 3H), 2.05 (s, 3H), 2.35 (s, 3H), 2.40 (m, 1H), 3.00 (m, 1H), 3.09 (s, 3H), 3.12 (m, 2H), 3.33 (m, 1H), 3.45 (s, 1H), 3.58 (d, J=6 Hz, 1H), 3.65 (d, J=10 Hz, 1H), 3.7-4.0 (m, 4H), 4.62 (m, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.20 (s, 1H), 8.89 (s, 1H), 14.58 (s, 1H).

Preparation of RTI-103 4-deoxy-3,4[2-spiro-[1-(isopropylaminocarbonyl)-piperidin-4-yl]]-(1H)-imidazo-(2,5-dihydro)rifamycin S Following the general procedure (B), the title compound was obtained as a pure solid. HRMS (ESI$^+$): 898.4194 (M+Na)$^+$; calculated for (M+Na)$^+$: 898.4215; RTI-103 1H-NMR (300 MHz, CDCl3); −0.04 (d, J=7 Hz, 3H), 0.61 (d, J=7 Hz, 3H), 0.84 (d, J=7 Hz, 3H), 1.04 (d, J=7 Hz, 3H), 1.21 (d, J=7 Hz, 6H), 1.44 (m, 1H), 1.55 (m, 1H), 1.65-1.90 (m 3H), 1.75 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.45 (s, 1H), 3.58 (d, J=6 Hz, 1H), 3.66 (d, J=10 Hz, 1H), 3.7-4.0 (m, 4H), 4.03 (m, 4H), 4.33 (d, J=7 Hz, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.20 (s, 1H), 8.89 (s, 1H), 14.59 (s, 1H).

Preparation of RTI-104 4-deoxy-3,4[2-spiro-[1-((1-methylpropyl)aminocarbonyl)-piperidin-4-yl]]-(1H)-imidazo-(2,5-dihydro)rifamycin S Following the general procedure (B) the title compound was obtained as a pure solid. HRMS (ESI$^+$): 912.4337 (M+Na)$^+$; calculated for (M+Na)$^+$: 912.4371; RTI-104 1H-NMR (300 MHz, CDCl3); −0.04 (d, J=7 Hz, 3H), 0.61 (d, J=7 Hz, 3H), 0.84 (d, J=7 Hz, 3H), 0.95 (t, J=7 Hz, 3H), 1.04 (d, J=7 Hz, 3H), 1.18 (d, J=7 Hz, 3H), 1.4-1.6 (m, 4H), 1.65-1.85 (m, 3H), 1.75 (s, 3H), 2.0-2.15 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.45 (s, 1H), 3.58 (d, J=6 Hz, 1H), 3.66 (d, J=10 Hz, 1H), 3.7-4.0 (m, 5H), 4.30 (d, J=8 Hz, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.38 (m, 1H), 8.20 (s, 1H), 8.89 (s, 1H), 14.59 (s, 1H).

Preparation of RTI-105 4-deoxy-3,4[2-spiro-[1-(t-butylaminocarbonyl)-piperidin-4-yl]]-(1H)-imidazo-(2,5-dihydro)rifamycin S Following the general procedure (B), the title compound was obtained as a pure solid. HRMS (ESI$^+$): 912.4333 (M+Na)$^+$; calculated for (M+Na)$^+$: 912.4371; RTI-105 1H-NMR (300 MHz, CDCl3); −0.05 (d, J=7 Hz, 3H), 0.61 (d, J=7 Hz, 3H), 0.84 (d, J=7 Hz, 3H), 1.04 (d, J=7 Hz, 3H), 1.40 (s, 9H), 1.4-1.6 (m, 2H), 1.7-1.85 (m, 3H), 1.75 (s, 3H), 2.0-2.15 (m, 2H), 2.01 (s, 3H), 2.05 (s, 3H), 2.35 (s, 3H), 2.40 (m, 1H), 3.00 (m, 1H), 3.09 (s, 3H), 3.33 (m, 1H), 3.46 (s, 1H), 3.59 (d, J=6 Hz, 1H), 3.66 (d, J=10 Hz, 1H), 3.7-4.0 (m, 4H), 4.43 (s, 1H), 4.73 (d, J=10 Hz, 1H), 5.13 (dd, J=12 and 7 Hz, 1H), 6.00 (dd, J=16 and 7 Hz, 1H), 6.18 (d, J=12 Hz 1H), 6.27 (d, J=10 Hz, 1H), 6.38 (m, 1H), 8.22 (s, 1H), 8.87 (s, 1H), 14.60 (s, 1H).

Preparation of RTI-175 11-deoxy-11-hydroxy-4-deoxy-3,4[2-spiro-[1-(isobutyloxycarbonyl)-piperidin-4-yl]]-(1H)-imidazo-(2,5-dihydro)rifamycin S Following the general procedure (C), the title compound was obtained as a pure solid. HRMS (ESI$^+$): 915.4334 (M+Na)$^+$; calculated for (M+Na)$^+$: 915.4368; RTI-175, 1H-NMR (300 MHz, CDCl3); 0.05 (d, J=7 Hz, 3H), 0.63 (d, J=7 Hz, 3H), 0.85 (d, J=7 Hz, 3H), 0.96 (d, J=7 Hz, 6H), 1.04 (d, J=7 Hz, 3H), 1.40-1.60 (m, 2H), 1.7-2.1 (m, 6H), 1.93 (s, 3H), 2.05 (s, 3H), 2.07 (s, 3H), 2.24 (s, 3H), 2.40 (m, 1H), 3.00 (m, 1H), 3.07 (s, 3H), 3.48 (m, 1H), 3.68 (s, 1H), 3.5-3.8 (m, 2H), 3.86 (d, J=6 Hz, 2H), 3.85-4.1 (m, 4H), 4.95 (dd, J=12 and 4 Hz, 1H), 5.05 (d, J=10 Hz, 1H), 5.54 (s, 1H), 5.99 (d, J=12 Hz, 1H), 6.16 (dd, J=16 and 6 Hz, 1H), 6.27 (d, J=10 Hz, 1H), 6.44 (dd, J=16 and 10 Hz, 1H), 6.72 (s, 1H) 8.07 (s, 1H), 8.22 (bs, 1H), 13.61 (s, 1H).

Preparation of RTI-176 11-deoxy-11-amino-4-deoxy-3,4[2-spiro-[1-(isobutyloxycarbonyl)-piperidin-4-yl]]-(1H)-imidazo-(2,5-dihydro)rifamycin S Following the general procedure (C), the title compound was obtained as a pure solid. HRMS (ESI$^+$): 892.4689

(M+H)+; calculated for (M+H)+: 892.4710; RTI-176 (RTI2-63B, 1H-NMR (300 MHz) (CDCl3); −0.05 (d, J=7 Hz, 3H), 0.64 (d, J=7 Hz, 3H), 0.85 (d, J=7 Hz, 3H), 0.96 (d, J=7 Hz, 6H), 1.04 (d, J=7 Hz, 3H), 1.40-1.70 (m, 2H), 1.7-1.9 (m, 4H), 1.9-2.1 (m, 2H), 1.94 (s, 3H), 2.05 (s, 3H), 2.08 (s, 3H), 2.24 (s, 3H), 2.40 (m, 1H), 2.6-2.8 (br, 2H), 3.03 (m, 1H), 3.07 (s, 3H), 3.52 (m, 1H), 3.67 (s, 1H), 3.6-3.7 (m, 2H), 3.80 (d, J=10 Hz, 1H), 3.91 (d, J=6 Hz, 2H), 3.85-4.1 (m, 2H), 4.11 (d, J=4 Hz, 1H), 4.77 (s, 1H), 4.87 (dd, J=12 and 4 Hz, 1H), 5.09 (d, J=10 Hz, 1H), 5.98 (d, J=12 Hz, 1H), 6.18 (dd, J=16 and 6 Hz, 1H), 6.25 (d, J=10 Hz, 1H), 6.44 (dd, J=16 and 11 Hz, 1H), 8.19 (s, 1H), 8.24 (bs, 1H), 13.93 (s, 1H).

Preparation of RTI-181 11-deoxy-11-amino-4-deoxy-3,4[2-spiro-[1-(2-methylpropyl)-piperidin-4-yl]]-(1H)-imidazo-(2,5-dihydro)rifamycin S Following the general procedure (C), the title compound was obtained as a pure solid. HRMS (ESI+): 848.4777 (M+H)+; calculated for (M+H)+: 848.4811; RTI-181, 1H-NMR (300 MHz, CDCl3); −0.05 (d, J=7 Hz, 3H), 0.63 (d, J=7 Hz, 3H), 0.85 (d, J=7 Hz, 3H), 0.92 (d, J=6 Hz, 6H), 1.04 (d, J=7 Hz, 3H), 1.40-1.50 (m, 1H), 1.7-2.1 (m, 9H), 1.94 (s, 3H), 2.05 (s, 3H), 2.07 (s, 3H), 2.23 (s, 3H), 2.24 (m, 2H), 2.40 (m, 1H), 2.6-2.8 (m, 4H), 3.03 (m, 1H), 3.07 (s, 3H), 3.50 (m, 1H), 3.68 (s, 1H), 3.80 (d, J=10 Hz, 1H), 4.11 (d, J=4 Hz, 1H), 4.76 (s, 1H), 4.87 (dd, J=12 and 4 Hz, 1H), 5.09 (d, J=10 Hz, 1H), 5.98 (d, J=12 Hz, 1H), 6.18 (dd, J=16 and 6 Hz, 1H), 6.25 (d, J=10 Hz, 1H), 6.44 (dd, J=16 and 11 Hz, 1H), 8.27 (s, 1H), 8.32 (s, 1H), 14.03 (s, 1H).

Preparation of RTI-182 11-deoxy-11-imino-4-deoxy-3,4[2-spiro-[1-(isobutylaminocarbonyl)-piperidin-4-yl]]-(1H)-imidazo-(2,5-dihydro)rifamycin S Following the general procedure (A), the title compound was obtained as a pure solid. HRMS (ESI+): 889.4678 (M+H)+; calculated for (M+H)+: 889.4713; RTI-182 1H-NMR (300 MHz, CDCl3); −0.08 (d, J=7 Hz, 3H), 0.61 (d, J=7 Hz, 3H), 0.84 (d, J=7 Hz, 3H), 0.96 (d, J=7 Hz, 6H), 1.04 (d, J=7 Hz, 3H), 1.4 (m, 1H), 1.65 (m, 1H), 1.7-1.85 (m, 4H), 1.88 (s, 3H), 1.95-2.15 (m, 2H), 2.02 (s, 3H), 2.05 (s, 3H), 2.34 (s, 3H), 2.40 (m, 1H), 3.00 (m, 1H), 3.09 (s, 3H), 3.12 (m, 2H), 3.33 (m, 1H), 3.50 (s, 1H), 3.62 (d, J=5 Hz, 1H), 3.67 (d, J=9 Hz, 1H), 3.6-3.7 (m, 2H), 3.8-4.0 (m, 2H), 4.62 (t, J=5 Hz, 1H), 4.72 (d, J=10 Hz, 1H), 5.06 (dd, J=12 and 7 Hz, 1H), 6.02 (dd, J=15 and 7 Hz, 1H), 6.16 (d, J=12 Hz, 1H), 6.29 (d, J=10 Hz, 1H), 6.38 (m, 1H), 8.27 (s, 1H), 8.67 (s, 1H), 12.92 (s, 1H), 14.58 (s, 1H).

Preparation of RTI-183 11-deoxy-11-amino-4-deoxy-3,4[2-spiro-[1-(isobuylaminocarbonyl)-piperidin-4-yl]]-(1H)-imidazo-(2,5-dihydro)rifamycin S Following the general procedure (C), the title compound was obtained as a pure solid. HRMS (ESI+): 891.4843 (M+H)+; calculated for (M+H)+: 891.4870; RTI-183, 1H-NMR (300 MHz, CDCl3); −0.05 (d, J=7 Hz, 3H), 0.64 (d, J=7 Hz, 3H), 0.85 (d, J=7 Hz, 3H), 0.94 (d, J=7 Hz, 6H), 1.04 (d, J=7 Hz, 3H), 1.48 (m, 1H), 1.7-1.89 (m, 8H), 1.94 (s, 3H), 2.01 (m, 1H), 2.04 (s, 3H), 2.08 (s, 3H), 2.24 (s, 3H), 2.40 (m, 1H), 3.03 (m, 1H), 3.07 (s, 3H), 3.09 (m, 2H), 3.52 (m, 1H), 3.55-3.75 (m, 3H), 3.75 (s, 1H), 3.81 (d, J=10 Hz, 1H), 3.85-4.0 (m, 1H), 4.13 (d, J=4 Hz, 1H), 4.62 (t, J=5 Hz, 1H), 4.77 (s, 1H), 4.88 (dd, J=12 and 4 Hz, 1H), 5.09 (d, J=10 Hz 1H), 5.98 (d, J=12 Hz, 1H), 6.18 (dd, J=16 and 6 Hz, 1H), 6.26 (d, J=10 Hz, 1H), 6.44 (dd, J=16 and 11 Hz, 1H), 8.20 (s, 1H), 8.35 (s, 1H), 13.94 (s, 1).

Preparation of RTI-75 4-deoxy-3,4[2-spiro-[1-(t-butyloxycarbonyl)-piperidin-4-yl]]-(1H)-imidazo-(2,5-dihydro)rifamycin S Following the general procedure (B), the title compound was obtained as a pure solid. HRMS (ESI+): 913.4267 (M+Na)+; calculated for (M+Na)+: 913.4211; RTI-75A, 1H-NMR (300 MHz, CDCl3); −0.04 (d, J=7 Hz, 3H), 0.61 (d, J=7 Hz, 3H), 0.84 (d, J=7 Hz, 3H), 1.04 (d, J=7 Hz, 3H), 1.40-1.60 (m, 2H), 1.51 (s, 9H), 1.7-1.85 (m, 3H), 1.75 (s, 3H), 1.9-2.1 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.43 (s, 1H), 3.57 (d, J=5 Hz, 1H), 3.67 (d, J=10 Hz, 1H), 3.6-3.8 (br, 2H), 3.9-4.1 (br, 2H), 4.72 (d, J=10 Hz, 1H), 5.13 (dd, J=12 and 7 Hz, 1H), 6.02 (dd, J=16 and 7 Hz, 1H), 6.18 (d, J=12 Hz, 1H), 6.28 (d, J=10 Hz, 1H), 6.40 (dd, J=16 and 10 Hz, 1H), 8.19 (s, 1H), 8.93 (bs, 1H), 14.59 (s, 1H).

Preparation of RTI-76 4-deoxy-3,4[2-spiro-[1-(ethyloxycarbonyl)-piperidin-4-yl]]-(1H)-imidazo-(2,5-dihydro)rifamycin S Following the general procedure (B), the title compound was obtained as a pure solid. HRMS (ESI+): 885.3945 (M+Na)+; calculated for (M+Na)+ 885.3898 RTI-76A, 1H-NMR (300 MHz, CDCl3); −0.04 (d, J=7 Hz, 3H), 0.61 (d, J=7 Hz, 3H), 0.84 (d, J=7 Hz, 3H), 1.04 (d, J=7 Hz, 3H), 1.30 (t, J=7 Hz, 3H), 1.40-1.60 (m, 2H), 1.7-1.85 (m, 3H), 1.75 (s, 3H), 1.9-2.1 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.44 (s, 1H), 3.57 (d, J=5 Hz, 1H), 3.66 (d, J=10 Hz, 1H), 3.7-3.9 (br, 2H), 4.0-4.2 (br, 2H), 4.21 (q, J=7 Hz, 2H), 4.72 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.40 (dd, J=16 and 10 Hz 1H), 8.20 (s, 1H), 8.92 (bs, 1H), 14.58 (s, 1H).

Preparation of RTI-78 4-deoxy-3,4[2-spiro-[1-(n-propyloxy)carbonyl)-piperidin-4-yl]]-(1H)-imidazo-(2,5-dihydro)rifamycin S Following the general procedure (B), the title compound was obtained as a pure solid. HRMS (ESI+): 899.3989 (M+Na)+; calculated for (M+Na)+ 899.4054; RTI-78A, 1H-NMR (300 MHz, CDCl3); −0.04 (d, J=7 Hz, 3H), 0.61 (d, J=7 Hz, 3H), 0.84 (d, J=7 Hz, 3H), 0.99 (t, J=7 Hz, 3H), 1.04 (d, J=7 Hz, 3H), 1.40-1.60 (m, 2H), 1.69 (m, 2H), 1.7-1.85 (m, 3H), 1.75 (s, 3H), 1.95-2.1 (m, 2H), 2.02 (s, 3H), 2.05 (s, 3H), 2.35 (s, 3H), 2.40 (m, 1H), 3.00 (m, 1H), 3.09 (s, 3H), 3.33 (m, 1H), 3.42 (s, 1H), 3.56 (d, J=5 Hz, 1H), 3.66 (d, J=10 Hz, 1H), 3.7-3.9 (br, 2H), 4.0-4.2 (br, 2H), 4.11 (t, J=7 Hz, 2H), 4.72 (d, J=10 Hz, 1H), 5.13 (dd, J=12 and 7 Hz, 1H), 6.00 (dd, J=16 and 7 Hz, 1H), 6.18 (d, J=12 Hz, 1H), 6.27 (d, J=10 Hz, 1H), 6.40 (dd, J=16 and 10 Hz, 1H), 8.17 (s, 1H), 8.92 (bs, 1H), 14.57 (s, 1H).

Preparation of RTI-79 4-deoxy-3,4[2-spiro-[1-(isobutyloxycarbonyl)-piperidin-4-yl]]-(1H)-imidazo-(2,5-dihydro)rifamycin S Following the general procedure (B), the title compound was obtained as a pure solid. HRMS (ESI+): 913.4163 (M+Na)+; calculated for (M+Na)+ 913.4211; RTI-79A, 1H-NMR (300 MHz, CDCl3); −0.03 (d, J=7 Hz, 3H), 0.61

(d, J=7 Hz, 3H), 0.84 (d, J=7 Hz, 3H), 0.97 (d, J=7 Hz, 6H), 1.04 (d, J=7 Hz, 3H), 1.40-1.60 (m, 2H), 1.7-1.85 (m, 3H), 1.75 (s, 3H), 1.9-2.1 (m, 3H), 2.02 (s, 3H), 2.05 (s, 3H), 2.35 (s, 3H), 2.40 (m, 1H), 3.00 (m, 1H), 3.09 (s, 3H), 3.33 (m, 1H), 3.42 (s, 1H), 3.56 (d, J=5 Hz, 1H), 3.66 (d, J=10 Hz, 1H), 3.7-3.9 (br, 2H), 3.93 (d, J=6 Hz, 2H), 4.0-4.2 (br, 2H), 4.72 (d, J=10 Hz, 1H), 5.13 (dd, J=12 and 7 Hz, 1H), 6.00 (dd, J=16 and 7 Hz, 1H), 6.19 (d, J=12 Hz, 1H), 6.27 (d, J=10 Hz, 1H), 6.39 (dd, J=16 and 10 Hz, 1H), 8.17 (s, 1H), 8.93 (bs, 1H), 14.57 (s, 1H).

Preparation of RTI-80 4-deoxy-3,4[2-spiro-[1-(beR-Tlyloxycarbonyl)-piperidin-4-yl]]-(1H)-imidazo-(2,5-dihydro)rifamycin S Following the general procedure (B), the title compound was obtained as a pure solid. HRMS (ESI$^+$): 947.3987 (M+Na)$^+$; calculated for (M+Na)$^+$947.4054; RTI-80A, 1H-NMR (300 MHz, CDCl3); −0.04 (d, J=7 Hz, 3H), 0.61 (d, J=7 Hz, 3H), 0.84 (d, J=7 Hz, 3H), 1.04 (d, J=7 Hz, 3H), 1.40-1.60 (m, 2H), 1.7-1.85 (m, 3H), 1.74 (s, 3H), 1.9-2.1 (m, 2H), 2.01 (s, 3H), 2.04 (s, 3H), 2.35 (s, 3H), 2.40 (m, 1H), 3.00 (m, 1H), 3.09 (s, 3H), 3.33 (br, 1H), 3.42 (br, 1H) 3.56 (d, J=5 Hz, 1H), 3.66 (d, J=10 Hz, 1H), 3.7-3.9 (br, 2H), 4.0-4.2 (br, 2H), 4.72 (d, J=10 Hz, 1H), 5.13 (dd, J=12 and 7 Hz, 1H), 5.20 (m, 2H), 6.00 (dd, J=16 and 7 Hz, 1H), 6.18 (d, J=12 Hz, 1H), 6.27 (d, J=10 Hz, 1H), 6.39 (dd, J=16 and 10 Hz, 1H), 7.39 (m, 5H), 8.16 (s, 1H), 8.93 (bs, 1H), 14.57 (s, 1H).

Preparation of RTI-174 11-deoxy-11-hydroxy-4-deoxy-3,4[2-spiro-[1-(2-methylpropyl)-piperidin-4-yl]]-(1H)-imidazo-(2,5-dihydro)rifamycin S Following the general procedure (C), the title compound was obtained as a pure solid. HRMS (ESI$^+$): 871.4433 (M+Na)$^+$; calculated for (M+Na)$^+$871.4470.

Preparation of RTI-197 11-deoxy-11-hydroxyimino-4-deoxy-3,4[2-spiro-[1-(isobutyloxycarbonyl)-piperidin-4-yl]]-(1H)-imidazo-(2,5-dihydro)rifamycin S Following the general procedure (D), the title compound was obtained as a solid. HRMS (ESI$^+$): 906.4535 (M+H)$^+$; calculated for (M+H)$^+$ 906.4535; RTI-197 1H-NMR (300 MHz, CDCl3); −0.03 (d, J=7 Hz, 3H), 0.62 (d, J=7 Hz, 3H), 0.84 (d, J=7 Hz, 3H), 0.97 (d, J=7 Hz, 6H), 1.04 (d, J=7 Hz, 3H), 1.35-1.40 (m, 1H), 1.7-1.8 (m, 1H), 1.85-2.1 (m, 6H), 2.00 (s, 3H), 2.04 (s, 3H), 2.13 (s, 3H), 2.33 (s, 3H), 2.40 (m, 1H), 3.00 (m, 1H), 3.10 (s, 3H), 3.34 (m, 1H), 3.42-3.50 (m, 2H), 3.67 (d, J=10 Hz, 1H), 3.8-3.9 (m, 4H), 3.93 (d, J=6 Hz, 2H), 4.60 (d, J=10 Hz, 1H), 5.23 (dd, J=12 and 8 Hz, 1H), 5.98 (dd, J=15 and 6 Hz, 1H), 6.30 (d, J=12 Hz, 2H), 6.40 (dd, J=16 and 10 Hz, 1H), 8.35 (s, 1H), 8.92 (bs, 1H), 14.13 (s, 1H).

Preparation of RTI-217 11-deoxy-11-hydroxyimino-4-deoxy-3,4[2-spiro-[1-(isobutylaminocarbonyl)-piperidin-4-yl]]-(1H)-imidazo-(2,5-dihydro)rifamycin S Following the general procedure (D), the title compound was obtained as a solid. HRMS (ESI$^+$): 905.4695 (M+H)$^+$; calculated for (M+H)$^+$ 905.4662; RTI-217 1H-NMR (300 MHz, CDCl3); −0.03 (d, J=7 Hz, 3H), 0.62 (d, J=7 Hz, 3H), 0.84 (d, J=7 Hz, 3H), 0.95 (d, J=7 Hz, 6H), 1.04 (d, J=7 Hz, 3H), 1.35-1.40 (m, 1H), 1.7-1.8 (m, 1H), 1.85-2.1 (m, 6H), 2.00 (s, 3H), 2.04 (s, 3H), 2.13 (s, 3H), 2.33 (s, 3H), 2.40 (m, 1H), 3.00 (m, 1H), 3.10 (s, 3H), 3.08-3.14 (m, 2H), 3.34 (m, 1H), 3.45 (s, 1H), 3.47 (d, J=6 Hz, 1H), 3.65-3.8 (m, 5H), 4.60 (m, 2H), 5.23 (dd, J=12 and 8 Hz, 1H), 5.98 (dd, J=16 and 7 Hz, 1H), 6.30 (d, J=12 Hz, 2H), 6.40 (dd, J=16 and 10 Hz, 1H), 8.34 (s, 1H), 8.89 (s, 1H), 14.14 (s, 1H).

Preparation of a Rifabutin Derivative Modified on Alternative Sites

Biotin-glycine-substituted rifabutin derivative RTI-173 contains a substitution at the 21-hydroxy site. Biotin-glycine-linked rifabutin derivative (RTI-173) has the following formula:

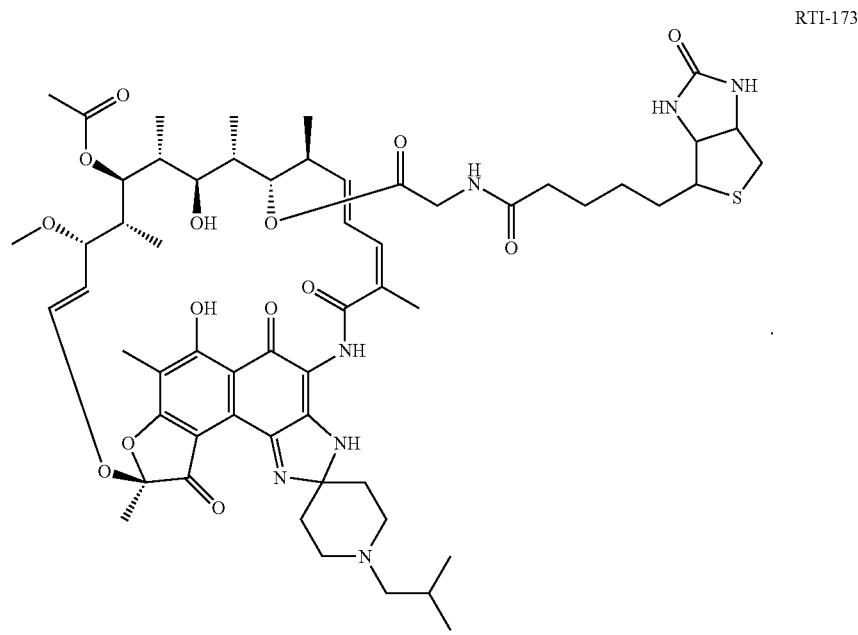 [SMILES: CO[C@H]1/C=C/O[C@@]2(C)Oc3c(C)c(O)c4c(c3C2=O)C2=NC3(CCN(CC(C)C)CC3)NC2=C(NC(=O)/C(C)=C\C=C\[C@H](C)[C@H](OC(=O)CNC(=O)CCCCC2SCC3NC(=O)NC32)[C@@H](C)[C@@H](O)[C@@H](C)[C@H](OC(C)=O)[C@@H]1C)C4=O]

RTI-173

RTI-173 was prepared by the following method:

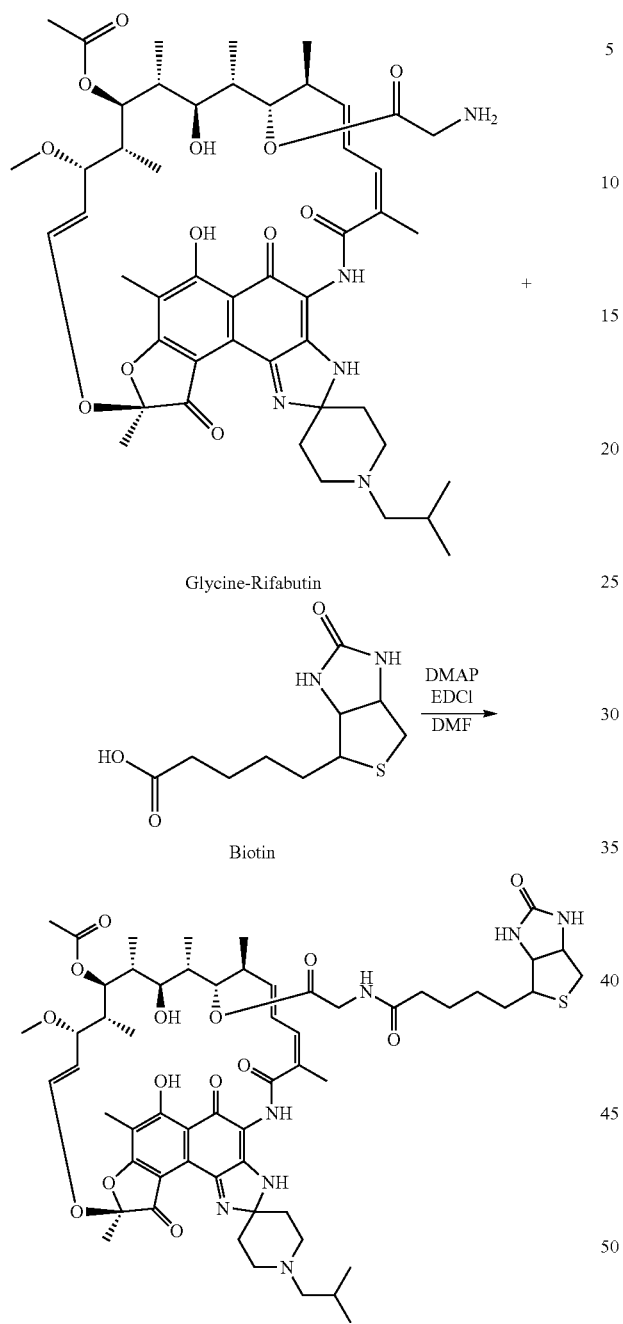

A solution of Glycine-rifabutin (240 mg, 0.27 mmole) in DMF (2 ml) was added to a solution of biotin (65 mg, 0.27 mmol), DMAP (33 mg, 0.27 mmol) and EDCI (52 mg, 0.27 mmole) in DMF (3 ml) at room temperature. The reaction mixture stirred at room temperature overnight and diluted with DCM (40 ml) and washed with water and brine. The organic phase was dried over anhydrous sodium sulphate, filtered and concentrated under vacuum. The residue was purified by silica gel column chromatography with methanol in DCM as eluent to give 108 mg of the product as purple solid. HRMS (ESI$^+$): 1152.5538 (M+Na)$^+$; calculated for (M+Na)$^+$1152.5304.

Example 2

Chloroquine Sensitization in Chloroquine-Resistant *P. Falciparum*

Efficacy of RTI-79 in restoring chloroquine sensitivity in chloroquine resistant *P. Falciparum* is evaluated. RTI-79 has previously been demonstrated to prevent drug efflux from cells by inhibition of membrane drug pump proteins, including P-gp. Quinine and quinine derivatives including chloroquine inhibit the *Plasmodium* parasites, including *P. Falciparum*, by accumulating in food vacuoles and causing accumulation of cytotoxic heme, thereby poisoning the parasite. Drug pump activity is a primary mediator of chloroquine resistance.

The effect of RTI-79 on two chloroquine resistant *P. Falciparum* variants and the chloroquine sensitive 3D7 variant is measured. The half-maximal inhibitory concentration (IC$_{50}$) of chloroquine for the chloroquine sensitive 3D7 variant is confirmed experimentally. Subsequently, all three *P. Falciparum* variants are subject to one of four chloroquine treatments: (i) exposure to chloroquine at the pre-determined IC50 for the chloroquine sensitive 3D7 variant; (ii) exposure to chloroquine in a concentration three times greater than the 3D7 IC$_{50}$; (iii) exposure to chloroquine at a concentration three times lower than the 3D7 IC$_{50}$; or (iv) no chloroquine treatment (negative control). For each chloroquine treatment experiment, RTI-79 is administered in a concentration of 0 μM, 5 μM, 10 μM, or 20 μM.

Exposure of the 3D7 *P. Falciparum* variant to chloroquine at a concentration at or greater than IC50 results in death of the parasite. All non-chloroquine treated variants survive. Chloroquine-resistant variants treated with chloroquine alone at a concentration equal to or less than the 3D7 IC$_{50}$ survive. Treatment with chloroquine and RTI-79 in combination reduces survival of all variants relative to treatment with chloroquine alone.

Example 3

In Vitro Activity of RTI-79 or Rifamycin in *P. Falciparum*

The inhibitory activity of RTI-79 in the chloroquine-sensitive 3D7 variant and the chloroquine-resistant Dd2 and K1 variants of *P. Falciparum* was tested in vitro. Chloroquine sensitivity of each of the variants was also measured and the observed sensitivity of the variants corresponded with previously-reported IC$_{50}$ of chloroquine in the chloroquine-sensitive 3D7 variant and in the chloroquine-resistant Dd2 and K1 *P. Falciparum* variants of ~10 nM, 100 nM, and 255 nM, respectively. The inhibitory activity of RTI-79 was compared to that of rifamycin in both the chloroquine-sensitive 3D7 variant and a chloroquine resistant variant Sensitivity of the *P. Falciparum* variants to (i.e. inhibition of the parasites by) RTI-79chloroquine, or rifamycin was quantitated via assay as previously described. Duffy, S. and V. M. Avery, *Development and optimization of a novel 384-well anti-malarial imaging assay validated for high-throughput screening*. Am J Trop Med Hyg, 2012. 86(1): p. 84-92. Inhibition of *P. Falciparum* with various concentrations of the inhibitors was quantified by measuring DAPI fluorescence of parasite DNA in erythrocyte cultures.

Figure 1B:
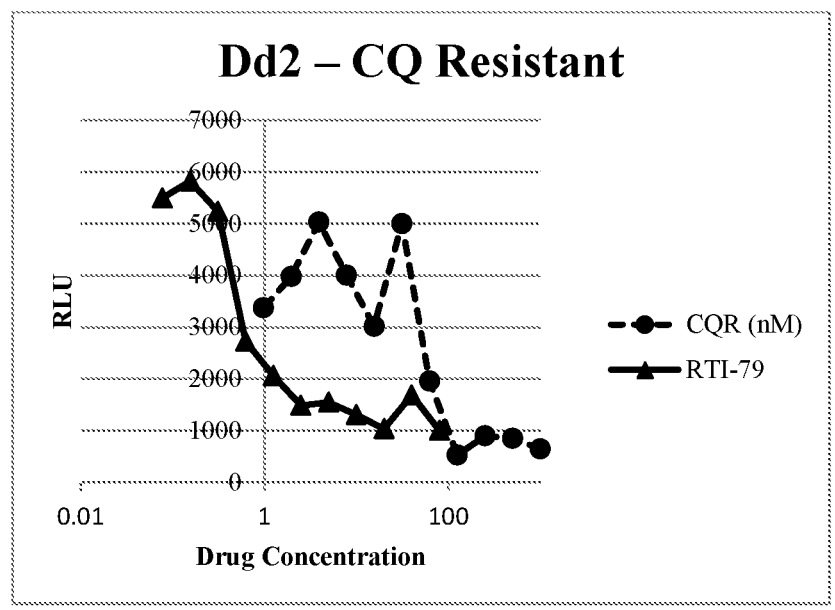
FIG. 1B is a graph of the dose response curves of chloroquine-resistant Dd2 P. falciparum to chloroquine (CQR) and RTI-79 according to an exemplary embodiment of the present disclosure.
Figure 1C:
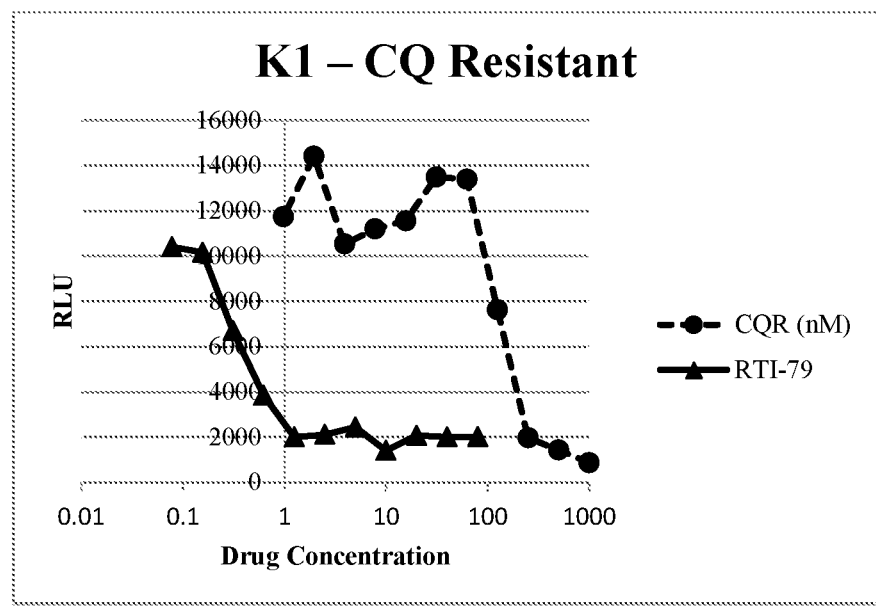
FIG. 1C is a graph of the dose response curves of chloroquine sensitive K1 P. falciparum to chloroquine (CQR) and RTI-79 according to an exemplary embodiment of the present disclosure.

Inhibition of the CD7, Dd2, and K1 variants of *P. Falciparum* by RTI-79 or chloroquine is shown in FIGS. 1A, 1B, and 1C, respectively. Decreased DAPI staining quantified as relative light units ("RLU"), is observed with parasite inhibition in the assays. Dose-dependent inhibition of all strains was observed for RTI-79, while the observed $IC_{50}$ values for chloroquine in the chloroquine-sensitive and -resistant strains generally corresponded to the previously reported values. RTI-79 was a potent inhibitor of chloroquine-sensitive and -resistant variants with an observed $IC_{50}$ of ~0.625 uM in all variants.

Figure 2A:
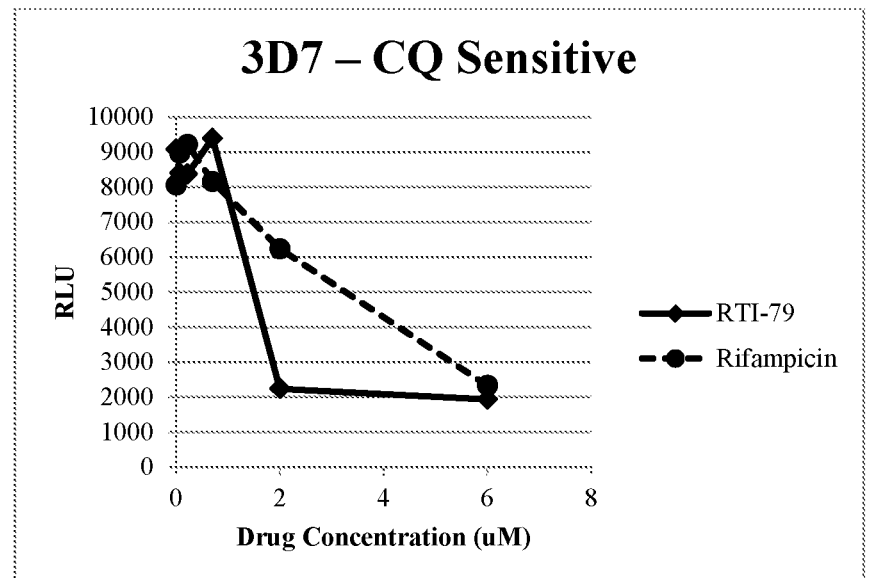
FIG. 2A is a graph of the dose response curves of chloroquine-sensitive 3D7 P. falciparum to RTI-79 and rifampicin according to an exemplary embodiment of the present disclosure.
Figure 2B:
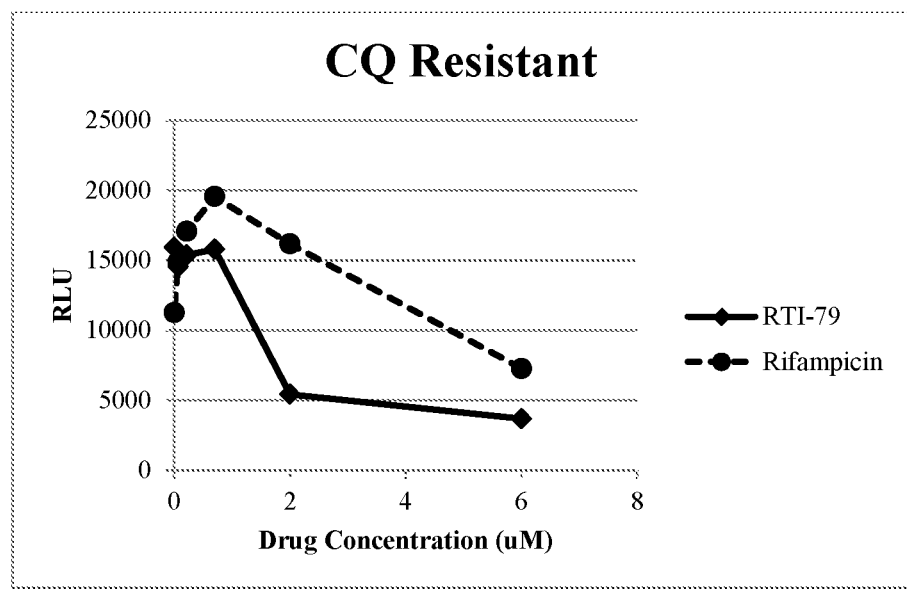
FIG. 2B is a graph of the dose response curves of chloroquine-resistant P. falciparum to RTI-79 and rifampicin according to an exemplary embodiment of the present disclosure.

Inhibition by RTI-79 or rifamycin in chloroquine-sensitive and -resistant *P. Falciparum* is shown in FIGS. 2A and 2B, respectively. RTI-79 was observed to be approximately three times more potent than rifamycin in both chloroquine-sensitive and -resistant *P. Falciparum* variants.

Example 4

Sensitization of Multidrug-resistant Nematode Parasites to Antiparasitic Drugs by Novel Rifamycin Derivatives Parasite sensitization to antiparasitic drug ivermectin by novel rifamycin derivatives RTI-79 and RTI-176 was evaluated in the multidrug (benzimidazole, levamisole, ivermectin, milbemycin) resistant *Haemonchus contortus* isolate UGA2004 in both larval motility and larval development assays.

In the larval motility assay, 96 well plates containing the UGA2004 *H. contortus* isolate larvae, ivermectin ("IVR"), and a pgp inhibitor (10 or 20 uM RTI-79 20 uM RTI-176, or 10 uM verapamil) or 1% dimethyl sulfoxide ("DMSO") control were prepared and incubated for 24 hours at room temperature in the dark. Each well contained a 300 uL solution containing approximately 75 L3 stage larvae, IVR, and pgp inhibitor or control. IVR was provided in serially diluted concentrations of 50, 25, 12.5, 6.25, 3.125, 1.56, 0.78 or 0.39 uM, to permit evaluation of the dose response to IVR in the presence of the pgp inhibitors. Inhibition of larval motility was determined by failure of the incubated larvea to move when stimulated by light exposure after incubation.

Figure 3A:
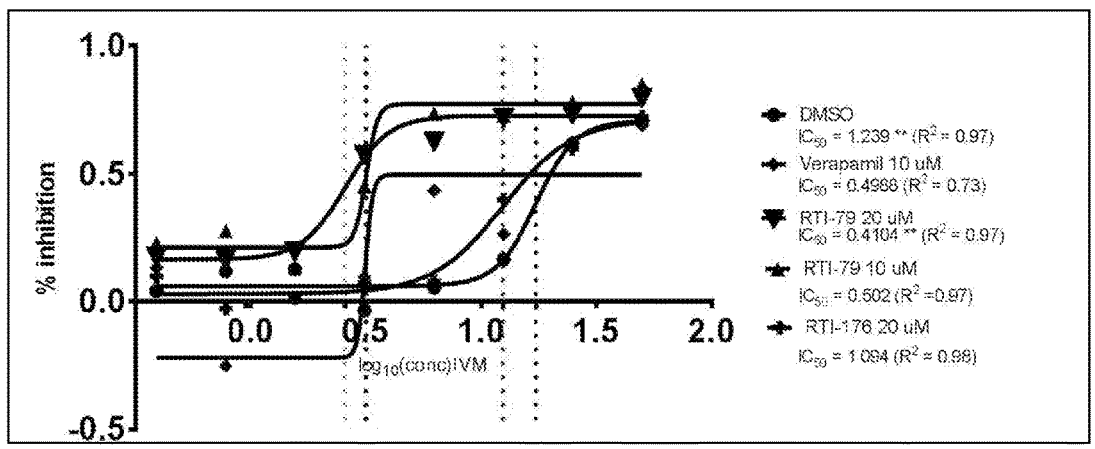
FIG. 3A is a graph of motility inhibition of multidrug-resistant H. contortus stage 3 larvae observed upon light exposure after 24 hour exposure to varying concentrations of ivermectin (IVM—x-axis) and novel rifamycin derivatives RTI-79, RTI-176, verapramil, or 1% DMSO according to an exemplary embodiment of the present disclosure.

The IVR dose response curves for each pgp inhibitor treatment and control are shown in FIG. 3A. As shown, both RTI-79 and RTI-176 shifted the IVR dose response curve to the left relative to the 1% DMSO control. 6.9-fold sensitization of the IVR-resistant *H. contortus* larvae to IVR was observed with RTI-79and more potent inhibition of larval motility was observed with both RTI-79 and RTI-176 than with verapamil, a known pgp inhibitor.

In the larval development assay, UGA2004 *H. contortus* isolate eggs were plated with nutritive media on agar containing thiabendazole ("TBZ") and a pgp inhibitor (RTI-79, RTI-176, or verapamil) or 1% DMSO control. TBZ was provided in a range of concentrations to permit evaluation of the dose response to TBZ in the presence of the pgp inhibitors. After incubation of the eggs for seven days, the number of stage 3 ("L3") larvae that developed with each treatment was counted.

Figure 3B:
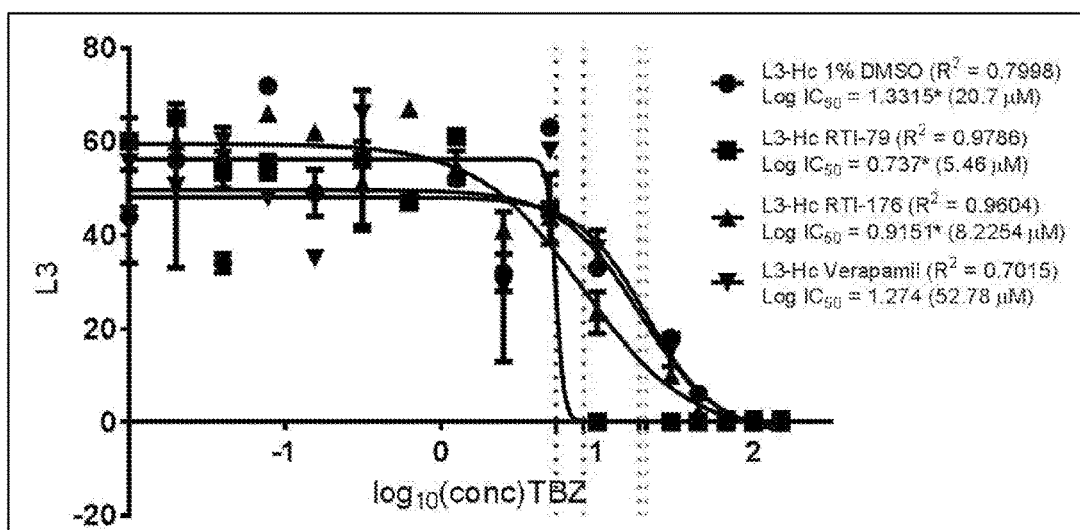
FIG. 3B is a graph of stage 3 (L3) larval population after 7-day incubation of multidrug-resistant H. contortus eggs with varying concentrations of thiabendazole (TBZ—x-axis) and novel rifamycin derivatives RTI-79, RTI-176, verapramil or 1% DMSO according to an exemplary embodiment of the present disclosure.

The TBZ dose response curves for each pgp inhibitor and control are shown in FIG. 3B. As shown, both RTI-79 and RTI-176 shifted the TBZ dose response curve to the left relative to both verapamil and to the 1% DMSO control. A 3.79-fold shift of the IC50 of TBZ was observed with RTI-79 and RI-176 treatment relative to control and verapamil.

Example 5

Example Rifabutin and Rifabutin Derivative Compositions and Methods of Administration to an Organism Susceptible Infection by or Infected by a Drug-Resistant Parasite Rifamycin and rifamycin derivative, such as rifabutin or rifabutin derivatives, rifampicin and rifampicin derivatives, and pharmaceutically acceptable salts, hydrates, and prodrugs thereof, or combinations thereof, can be prepared as described herein.

In particular, compositions can be formulated in tablets or capsules for oral use. These tablets or capsules can be extended release tablets or capsules to provide a more stable and continuous bioavailability to the recipient. Tablets or capsules can contain at least 10 mg, at least 50 mg, at least 100 mg, at least 150 mg, or at least 200 mg, of rifamycin or rifamycin derivative. Combination tablets or capsules with other antiparasitic drugs, such as chemotherapeutic or xenobiotic drugs, can be prepared, particularly if the recommended dosing schedule for those drugs is similar to that of the rifamycin, rifamycin derivative, rifampicin, rifampicin derivative, or pharmaceutically acceptable salt, hydrate, or prodrug thereof, or combination thereof. For example, the rifamycin, rifamycin derivative, rifampicin, rifampicin derivative, or pharmaceutically acceptable salt, hydrate, or prodrug thereof, or combination thereof can be combined with an avermectin, such as ivermectin.

Compositions can also be formulated for intravenous injection as well. In general the amount of rifamycin, rifamycin derivative, rifampicin, rifampicin derivative, or pharmaceutically acceptable salt, hydrate, or prodrug thereof, or combination thereof can be lower in a dose formulated for intravenous injection than in a dose formulated for oral administration because intravenous injection avoids the need for absorption through the intestines. Injectable doses can be provided in multi-use containers or in single-use containers. These containers can be compatible for use with standard intravenous needles and syringes as well as intravenous drip systems and more complex chemotherapeutic administration systems. Single-use containers can contain the entire amount administered to avoid the need for multiple injections of the drug. Alternatively, they can contain amounts appropriate for daily doses. Single-use containers can contain at least 1 mg, at least 5 mg, at least 10 mg, at least 50 mg, at least 100 mg, or at least 150 mg, of rifamycin, rifamycin derivative, rifampicin, rifampicin derivative, or pharmaceutically acceptable salt, hydrate, or prodrug thereof, or combination thereof\. Multi-use containers can be designed to allow administration of these same amounts of rifamycin, rifamycin derivative, rifampicin, rifampicin derivative, or pharmaceutically acceptable salt, hydrate, or prodrug thereof, or combination thereof. Injectable compositions can further contain other injectable antiparasitic drugs or other drugs commonly administered with treatment of parasitic infection.

Rifamycin and rifamycin derivative, such as rifabutin or rifabutin derivatives, rifampicin and rifampicin derivatives, and pharmaceutically acceptable salts, hydrates, and prodrugs thereof, or combinations thereof to recipients infected with or susceptible to infection by a parasite in the form of any compositions described in these examples or elsewhere herein or any other form. The recipients infected with or susceptible to infection by a parasite can be infected with or susceptible to infection by a parasite that is resistant to or which could develop resistance to one or more drugs. The recipients can additionally or alternatively benefit from administration of reduced amounts of one or more antiparasitic drugs, or can benefit from the administration of a particular drug to which the compositions disclosed herein sensitizes a parasite with which the recipient is infected or is susceptible to infection by.

In certain embodiments, the rifamycin, rifamycin derivative, rifampicin, rifampicin derivative, or pharmaceutically acceptable salt, hydrate, or prodrug thereof, or combination thereof, can be administered orally to organisms infected with a parasite. In particular, they can be administered in the form of tablets or capsules. The rifamycin or rifamycin derivative can be administered such that the recipient receives at least 50 mg/week, at least 100 mg/week, at least 150 mg/week, or at least 300 mg/week, or at least 600 mg/week, or at least 1 gram/week. Amounts can be reduced for children or young animals, and can be determined on the basis of the body weight of the recipient. For example, a human child under age 5 might receive one quarter or less of an adult human dose. A child age 5 to age 10 can receive one half to one quarter the adult human dose. A child age 10 or over can receive three quarters to one half the adult human dose. Depending on the species of the recipient, similar dosages can be determined based on the size or maturity of the developing recipient relative to that of a mature recipient of the same species. In certain embodiments, rifamycin, rifamycin derivative, rifampicin, rifampicin derivative, or pharmaceutically acceptable salt, hydrate, or prodrug thereof, or combination thereof, can be administered such that the recipient receives at least 0.5 mg/kg/week, at least 1 mg/kg/week, at least 2 mg/kg/week, at least 5 mg/kg/week, at least 10 mg/kg/week, at least 20 mg/kg/week, at least 30 mg/kg/week, at least 50 mg/kg/week, or at least 100 mg/kg/week.

The rifamycin, rifamycin derivative, rifampicin, rifampicin derivative, or pharmaceutically acceptable salt, hydrate, or prodrug thereof, or combination thereof, administered orally in this fashion can be administered weekly, daily, or multiple times per day. The dosing schedule can be adjusted so as to maintain minimal blood concentrations for a period of time particularly with extended release formulations.

Alternatively, maintenance of minimal blood concentrations is be necessary for some methods of treatment and dosing can instead be designed to achieve a total blood concentration for a shorter period of time such as for four hours or less. Although amounts are expressed as weekly totals, it will be understood that the compositions do not have to be administered for a full week. For example, a recipient can receive a single dose in connection with an antiparasitic treatment and not receive a further dose until much later, with another antiparasitic treatment, or not at all. Furthermore, it is possible to administer the weekly total through various combinations of doses on various days. For example, it can be possible to administer doses only every other day or every few days. Doses also need not be the same each day. For example, a patient can receive doses that increase or decrease over time, particularly due to the schedule for administration of chemotherapeutics. In certain embodiments, the recipient or their human caregiver can be provided with a pack of varying-dose tablets or capsules labeled by day (e.g. Day 1, Day 2, etc.) by portions of the day (e.g. Day 1 morning, Day 1 evening, etc.) or by week (e.g. Week 1, Week 2, etc.) and instructed to begin taking or administering the tablets or capsules at a specified time. In certain embodiments, this schedule can be dictated by the schedule for administration of an antiparasitic drug.

In general, the rifamycin, rifamycin derivative, rifampicin, rifampicin derivative, or pharmaceutically acceptable salt, hydrate, or prodrug thereof, or combination thereof, can be administered in connection with administration of an antiparasitic drug. In one example, it can be administered at least weekly or at least daily the entire time the patient is receiving a course of an antiparasitic drug, such as for several months. In certain embodiments it can be administered only to coincide with administration of an antiparasitic, such as for one day to one week each month coinciding with a once month antiparasitic drug administration.

In certain embodiments, the rifamycin, rifamycin derivative, rifampicin, rifampicin derivative, or pharmaceutically acceptable salt, hydrate, or prodrug thereof, or combination thereof, can be administered in the form of an edible or potable composition, such as a feed meal for livestock or a pre-packaged container of water, having a total pre-determined dosage.

In certain embodiments, the composition can be rifabutin or RTI-79 administered orally in one to three doses of rifabutin or RTI-79 in 100 mg to 300 mg amounts over a period of up to 48 hours beginning within 24 hours before or after the administration of an antiparasitic drug, such as chloroquine or ivermectin. A single oral dose of 300 mg rifabutin causes a mean (±SD) peak plasma concentration (Cmax) of 375 (±267) ng/mL (range 141 to 1033 ng/mL). The plasma elimination of rifabutin is biphasic with an initial half-life of approximately 4 hours, followed by a mean terminal half-life of 45 (±17) hours (range 16 to 69 hours). The rifabutin derivative RTI-79 is expected to present similar results. Accordingly, appropriate dosages for variations of these examples using intravenously injected rifabutin or RTI-79 rather than orally administered forms can be calculated.

In certain embodiments, the rifamycin, rifamycin derivative, rifampicin, rifampicin derivative, or pharmaceutically acceptable salt, hydrate, or prodrug thereof, or combination thereof, can be administered in a method that matches the pharmokinetics of the composition to that of the antiparasitic drug also administered to the recipient. For example, maximal ivermectin tissue absorption occurs within 3-5 hours after administration. Maximal RTI-79 plasma concentration is reached within 3 hours of administration. Accordingly, administering RTI-79 orally substantially simultaneously with or several hours after ivermectin administration can maximize efficacy.

Although only exemplary embodiments of the invention are specifically described above, it will be appreciated that modifications and variations of these examples are possible without departing from the spirit and intended scope of the invention. For example, various specific formulations including components not listed herein and specific methods of administering such formulations can be developed using the ordinary skill in the art. Numeric amounts expressed herein will be understood by one of ordinary skill in the art to include amounts that are approximately or about those expressed. Furthermore the term "or" as used herein is not intended to express exclusive options (either/or) unless the context specifically indicates that exclusivity is required; rather "or" is intended to be inclusive (and/or).

The invention claimed is:

1. A method of sensitizing a parasite to an antiparasitic drug comprising administering a composition having the following formula:

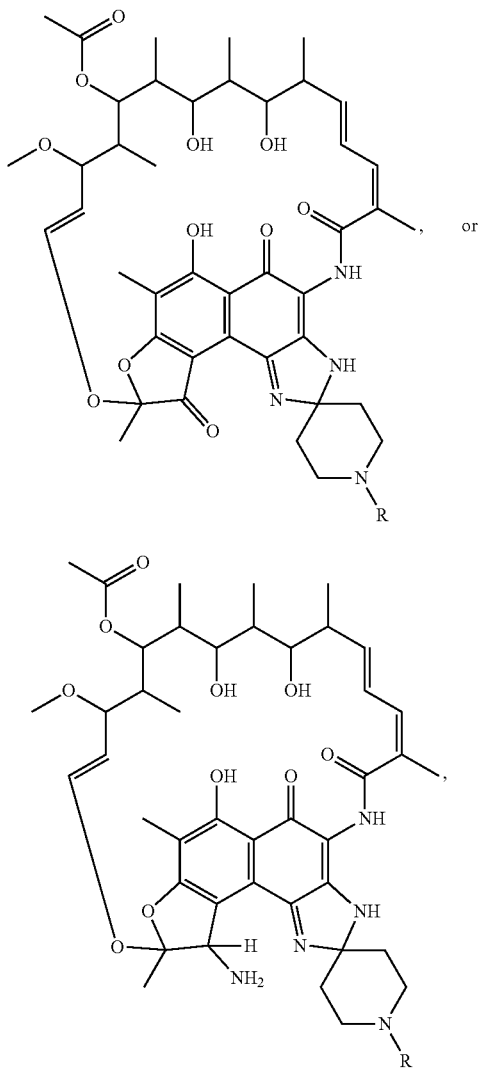

(II)

(III)

wherein R comprises one of the following structures:

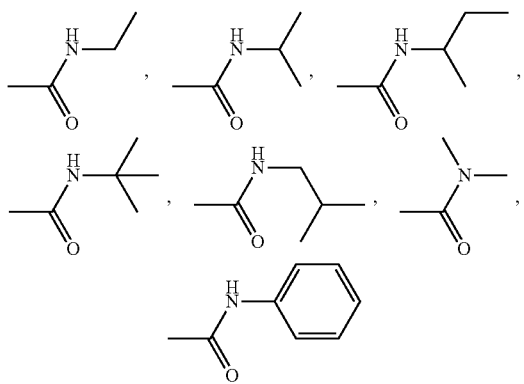

to the parasite that expresses a P-glycoprotein pump in an amount and for a time sufficient to sensitize the parasite to the antiparasitic drug by inhibiting the P-glycoprotein pump in the parasite and thereby reducing efflux of the antiparasitic drug from the parasite, wherein the antiparasitic drug is a macrocyclic lactone or a quinoline.

2. The method of claim 1, further comprising administering the composition to the parasite before administering the antiparasitic drug.

3. The method of claim 1, further comprising administering the composition to the parasite concurrently with the antiparasitic drug.

4. The method of claim 1, further comprising administering the composition to the parasite after administering the antiparasitic drug.

5. The method of claim 1, further comprising administering the composition to the parasite a second or greater time.

6. The method of claim 1, wherein administering the composition to the parasite in an amount and for a time sufficient to sensitize the parasite to the antiparasitic drug comprises rendering the parasite susceptible to the antiparasitic drug at a lower dose than in the absence of the composition.

7. The method of claim 1, wherein administering the composition to the parasite in an amount and for a time sufficient to sensitize the parasite to the antiparasitic drug comprises rendering the parasite susceptible to the antiparasitic drug that the parasite would not be susceptible to in the absence of the composition.

8. The method of claim 1, wherein administering the composition to the parasite in an amount and for a time sufficient to sensitize the parasite to the antiparasitic drug comprises rendering the parasite susceptible to death or a decrease in growth due to the antiparasitic drug.

9. The method of claim 1, wherein the parasite is a species of the genus *Plasmodium* or a species of the genus *Haemonchus*.

10. The method of claim 1, wherein the parasite is *Plasmodium falciparum*, *Plasmodium vivax*, *Plasmodium ovale*, or *Plasmodium malariea*.

11. The method of claim 1, wherein the composition is 4-deoxy-3,4[2-spiro-[1-(t-butyloxycarbonyl)-piperidin-4-yl]]-(1H)-imidazo-(2,5-dihydro)rifamycin S, 4-deoxy-3,4 [2-spiro-[1-ethyloxycarbonyl)-piperidin-4-yl]]-(1H)-imidazo-(2,5-dihydro)rifamycin S, 4-deoxy-3,4 [2-spiro-[1-(n-propyloxycarbonyl)-piperidin-4-yl]]-(1H)-imidazo-(2,5-dihydro)rifamycin S, 4-deoxy-3,4[2-spiro-[1-(isobutyloxycarbonyl)-piperidin-4-yl]]-(1H)-imidazo-(2,5-dihydro)rifamycin S, 4-deoxy-3,4[2-spiro-[1-(benzyloxycarbonyl)-piperidin-4-yl]]-(1H)-imidazo-(2,5-dihydro)rifamycin S, 4-deoxy-3,4[2-spiro-[1-(ethylaminocarbonyl)-piperidin-4-yl]]-(1H)-imidazo-(2,5-dihydro)rifamycin S, 4-deoxy-3,4[2-spiro-[1-(isopropyloxycarbonyl)-piperidin-4-yl]]-(1H)-imidazo-(2,5-dihydro)rifamycin S, 4-deoxy-3,4[2-spiro-[1-(phenylaminocarbonyl)-piperidin-4-yl]]-(1H)-imidazo-(2,5-dihydro)rifamycin S, 4-deoxy-3,4[2-spiro-[1-(acetyl)-piperidin-4-yl]]-(1H)-imidazo-(2,5-dihydro)rifamycin S, 4-deoxy-3,4[2-spiro-[1-(beRTIoyl)-piperdin-4-yl]]-(1H)-imidazo-(2,5-dihydro)rifamycin S, 4-deoxy-3,4[2-spiro-[1-(3,3-dimethylbutanoyl)-piperidin-4-yl]]-(1H)-imidazo-(2,5-dihydro)rifamycin S, 4-deoxy-3,4[2-spiro[1-(isobutylaminocarbonyl)-piperidin-4-yl]]-(1H)-imidazo-(2,5-dihydro)rifamycin S, 4-deoxy-3,4[2-spiro-[1-(isopropylaminocarbonyl)-piperidin-4-yl]]-(1H)-imidazo-(2,5-dihydro)rifamycin S, 4-deoxy-3,4[2-spiro-[1-((1-methylpropyl) aminocarbonyl)-piperidin-4-yl]]-(1H)-imidazo-(2,5-dihydro)rifamycin S, or 4-deoxy-3,4[2-spiro-[1-(t-butylaminocarbonyl)-piperidin-4-yl]]-(1H)-imidazo-(2,5-dihydro)rifamycin S,.

12. The method of claim 1, wherein the composition is 4-deoxy-3,4[2-spiro-[1-(isobutyloxycarbonyl)-piperidin-4-yl]]-(1H)-imidazo-(2,5-dihydro)rifamycin S.

13. The method of claim 1, wherein the parasite is *Haemonchus contortus*.

14. The method of claim 1, wherein the antiparasitic drug is ivermectin.

15. The method of claim 1, wherein the antiparasitic drug is iodoquinol.

16. The method of claim 1, wherein the antiparasitic drug is chloroquine, primaquine, mefloquine, quinine, or quinidine.

17. The method of claim 1, wherein the antiparasitic drug is praziquantel, or oxyminquine.

18. The method of claim 1, wherein the composition is 11-deoxy-11-amino-4-deoxy-3,4[2-spiro-[1-(isobutyloxycarbonyl)-piperidin-4-yl]]-(1H)-imidazo-(2,5-dihydro)rifamycin S.

* * * * *